(12) United States Patent
Tilbrook et al.

(10) Patent No.: US 9,914,738 B2
(45) Date of Patent: *Mar. 13, 2018

(54) SHORT-ACTING BENZODIAZEPINE SALTS AND THEIR POLYMORPHIC FORMS

(71) Applicant: Paion UK Limited, Cambridge Cambridgeshire (GB)

(72) Inventors: Gary Stuart Tilbrook, Huntington (GB); Louisa Jane Quegan, Cambridge (GB)

(73) Assignee: PAION UK LIMITED, Cambridge Cambridgeshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/703,945

(22) Filed: Sep. 13, 2017

(65) Prior Publication Data

US 2018/0002338 A1    Jan. 4, 2018

Related U.S. Application Data

(63) Continuation of application No. 14/948,889, filed on Nov. 23, 2015, now Pat. No. 9,777,007, which is a continuation of application No. 12/373,472, filed as application No. PCT/GB2007/002565 on Jul. 10, 2007, now Pat. No. 9,193,730.

(30) Foreign Application Priority Data

Jul. 10, 2006   (GB) .................................... 0613692.3
Jul. 10, 2006   (GB) .................................... 0613694.9

(51) Int. Cl.
*C07D 487/04*    (2006.01)
*C07C 309/29*    (2006.01)

(52) U.S. Cl.
CPC .......... *C07D 487/04* (2013.01); *C07C 309/29* (2013.01); *C07B 2200/07* (2013.01); *C07B 2200/13* (2013.01)

(58) Field of Classification Search
None
See application file for complete search history.

(56) References Cited

U.S. PATENT DOCUMENTS

| 3,520,877 A | 7/1970 | Fryer |
| 3,933,794 A | 1/1976 | Hester et al. |
| 5,019,583 A | 5/1991 | Feldman et al. |
| 5,665,718 A | 9/1997 | Godel et al. |
| 5,698,691 A | 12/1997 | Yukimasa et al. |
| 5,834,464 A | 11/1998 | Bock et al. |
| 6,916,923 B2 | 7/2005 | Ding et al. |
| 7,160,880 B1 | 1/2007 | Feldman et al. |
| 7,435,730 B2 | 10/2008 | Feldman et al. |
| 7,473,689 B2 | 1/2009 | Feldman et al. |
| 7,485,635 B2 | 2/2009 | Feldman et al. |
| 7,528,127 B2 | 5/2009 | Feldman et al. |
| 8,642,588 B2 | 2/2014 | Tilbrook et al. |
| 9,156,842 B2 | 10/2015 | Tilbrook et al. |
| 9,193,730 B2 | 11/2015 | Tilbrook et al. |
| 9,512,078 B2 | 12/2016 | Tilbrook et al. |
| 2006/0198896 A1 | 9/2006 | Liversidge et al. |
| 2010/0075955 A1 | 3/2010 | Tilbrook et al. |
| 2010/0081647 A1 | 4/2010 | Tilbrook et al. |
| 2011/0294843 A1 | 12/2011 | Soehngen et al. |
| 2012/0330007 A1 | 12/2012 | Tilbrook et al. |
| 2014/0080815 A1 | 3/2014 | Wilhelm-Ogunbiyi et al. |
| 2015/0148338 A1 | 5/2015 | Graham et al. |
| 2015/0224114 A1 | 8/2015 | Kondo et al. |
| 2015/0368199 A1 | 12/2015 | Tilbrook et al. |
| 2016/0009680 A1 | 1/2016 | Kawakami et al. |

FOREIGN PATENT DOCUMENTS

| CN | 1777613 | 5/2006 |
| EP | 0 166 356 A2 | 1/1986 |
| EP | 1 161 949 | 12/2001 |
| EP | 1 479 666 A1 | 11/2004 |
| EP | 1 718 665 A2 | 11/2006 |
| JP | 2002-544266 A | 12/2002 |

(Continued)

OTHER PUBLICATIONS

"Dose-Finding Safety Study Evaluating CNS 7056 in Patients Undergoing Diagnostic Upper GI Endoscopy", Clinical Trials.gov, Anonymous, Sep. 8, 2010, 1-4.
Baheti, A. et al., "Excipients used in lyophilization of small molecules," Journal of Excipients and Food Chem., 2010, vol. 1, 41-54.
Bauer M. et al, "Prolonged Sedation due to Accumulation of Conjugated Metabolites of Midazolam," The Lancet, 1995, 346, 145-147.
Chambon et al., "Ethyl Loflazepate: A Prodrug from the Benzodiazepine Series Designed to Dissociate Anxiolytic and Sedative Activities," Drug Res, 35 (II) Nr. 10, 1985, 1572-1577.
Crowley, et al., "Effects of excipients on the stability of medicinal products," Chemistry Today, 2010, vol. 28, VII-XIII.
Crowley, P., "Excipients as Stabilizers," Pharmaceutical Science and Technology Today, 1999, vol. 2, 237-243.
Dingemanse, J. et al., "Phannacokinetic-pharmacodynamlc modelling of the EEG effects of Ro 48-6791, a new short-acting benzodiazpine, in young and elderly subjects," British Journal of Anaesthesia, 1997, vol. 79, 567-574.

(Continued)

*Primary Examiner* — Noble E Jarrell
(74) *Attorney, Agent, or Firm* — Mintz Levin Cohn Ferris Glovsky and Popeo PC

(57) ABSTRACT

The invention relates to besylate salts of the compound of formula (I):

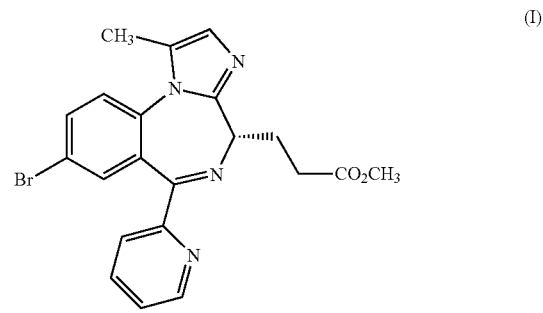

Methods of preparing the salts, and their use as medicaments, in particular for sedative or hypnotic, anxiolytic, muscle relaxant, or anticonvulsant purposes is also described.

12 Claims, 64 Drawing Sheets

(56) References Cited

FOREIGN PATENT DOCUMENTS

| | | |
|---|---|---|
| JP | 2008-515991 | 5/2008 |
| JP | 2008-526984 | 7/2008 |
| JP | 2009-542787 | 12/2009 |
| JP | 2011-153104 | 8/2011 |
| RU | 2249593 | 4/2005 |
| RU | 2004124370 A | 1/2006 |
| UZ | 02623 | 1/1997 |
| WO | WO-96/20941 A1 | 7/1996 |
| WO | WO-96/23790 A1 | 8/1996 |
| WO | WO-97/41896 | 11/1997 |
| WO | WO-00/69836 | 11/2000 |
| WO | WO-20051077072 | 8/2005 |
| WO | WO-2006/010620 A | 2/2006 |
| WO | WO-2006/044504 | 4/2006 |
| WO | WO-2006/078554 | 7/2006 |
| WO | WO-2008/007071 A1 | 1/2008 |
| WO | WO-2008/007081 A1 | 1/2008 |
| WO | WO-2008/147815 | 12/2008 |
| WO | WO-2009/145323 | 12/2009 |
| WO | WO-2010/116794 | 10/2010 |
| WO | WO-2011/032692 A1 | 3/2011 |
| WO | WO-2011/054845 | 5/2011 |
| WO | WO-2013/029431 | 3/2013 |
| WO | WO-2013/174883 | 11/2013 |

OTHER PUBLICATIONS

Dorwald, F. Zaragoza, "Side Reactions in Organic Synthesis: A Guide to Successful Synthesis Design," Weinheim: Wiley-VCH Verlag GmbH & Co. KGaA, Preface (2005).
Feldman et al., "Design, Synthesis, and Pharmacological Evaluation of Ultrashort-to Long-Acting Opioid Analgetics," J.Med.Chem., 1991, 34, 2202-2208.
Fryer, et al., "III. Conformational Shifts at the Benzodiazepine Receptor Related to the Binding of Agonists antagonists and Inverse Agonists," Life Sciences, vol. 39, Pergamon Journals Ltd., 1986, 1947-1957.
Fukuyama, L., et al., "t-Butyl (BOC) Carbamate" T.W.; Wuts, P.G.M.: "Protective Groups in Organic Synthesis" 1999, John Wiley & Sons Inc., New York, Chichester, Weinheim, Brisbane, Toronto, Singapore, XP002563125, ISBN:0471160199, p. 518.
Goodman et al., "The Pharmacological Basis of Therapeutics" Eighth Edition, 1990, 303-305, 346-358.
Greene, et al., "9-Fluorenylmethyl Carbamate," T.W.; Wuts, P.G.M.: "Protective Groups in Organic Synthesis" 1999, John Wiley & Sons Inc., New York, Chichester, Weinheim, Brisbane, Toronto, Singapore, XP002563125, ISBN: 0471160199, p. 506.
Hayashi M., et al., "Oxidative Conversion of Silyl Enol Ethers to alpha- beta-Unsaturated Ketones Employing Oxoammonium Salts," Organic Letters, vol. 14(1), pp. 154-157 (2012).
Hayashi, M. et al., "9-Azanoradamantane N-Oxyl (Nor-AZADO): A Highly Active Organocatalyst for Alcohol Oxidation," Chem. Pharm. Bull., vol. 59(12), pp. 1570-1573 (2011).
Hering W., et al., "Clinical Neurosciences," Anesthesiology, 1996, vol. 189, p. 85.
Hester, et al., "8-Chloro-1-methyl-6-phenyl-4H-s-triazolo [4,3-a] [1,4] benzodiazepines with Subslituents at C4," J. Med Chem., 1980, 23, 643-647.
Huali, W. et al., "Advances in the study of the stability of lyophilized formulations," Chinese Journal of Pharmaceutical Sciences, vol. 36(7)(Section 2):436-438 (Jul. 31, 2001). with English Translation (16 pages).

Jordan, V. C., "Tamoxifen: a most unlikely pioneering medicine," Nature Reviews: Drug Discovery, vol. 2 (3), pp. 205-213 (2003).
Kelly, A., et al: "Fentanyl Midazolam Combination for Endoscopy Sedation is Safe and Effective," Gastroenterology, vol. 114, Apr. 1998, p. A22, AGA Abstracts, Elsevier, Philadelphia, PA.
Khan, W.A., et al., "Organic Preparations and Procedures Int.," 1978, vol. 10(3), 105-111.
Kilpatrick et al., "A Novel Ultra-Short-acting Benzodiazepine", Anesthesiology, 2007. vol. 107, 60-66.
Lee, et al, "The Protective Effect of Lactose and Lyophilization of CNK-20402," AAPS Pharm Sci Tech., 2005, vol. 6. E42-E48.
Manghisi, et al., Synthesis and Central Nervous Effects of Some 3-Substituted-1, 4-Benzodiazepin-2-0nes, Boll. Chim. Farm ,1974, vol. 113, 642-644.
Ochs, et al., "Comparative Single-Dose Kinetics of Oxazolam, prazepam, and clorazepate: three precursors of desmethyldiazepam," J. Clin. Phannacol, 1984, vol. 24, 446-451.
Pace, V. et al., First General Route to Substituted a-Arylamino-a' -chloropropan-2-ones by Oxidation of N-Protected Aminohalohydrins: The Importance of Disrupting Hydrogen Bond Networks, Synthesis, vol. 20, pp. 3545-3555 (2010).
Pacofsky, G. et al., "Relating the Structure, Activity, and Physical Properties of Ultrashort-Acting Benzodiazepine Receptor Agonists," Bioorganic and Medicinal Chemistry Letters, 2002, vol. 12, 3219-3222.
Shafer, A., "Complications of Sedation with Midazolam in the Intensive Care Unit and a Comparison with other Sedative Regimens," Crit Care Med, 1998, 26, 947-956.
Shibuya M., et al., "Oxidation of nitroxyl radicals: electrochemical and computational studies," Tetrahedron Letters, vol. 53(16), pp. 2070-2073 (2012).
Shibuya, M. et al., "2-Azaadamantane N-Oxyl (AZADO): Highly efficient organocatalysts for oxidation of alcohols," Journal of the American Chemical Society, vol. 128, pp. 8412-8413 (2006).
Shibuya, M. et al., "Highly Efficient, Organocatalytic Aerobic Alcohol Oxidation," Journal of American Chemical Society, vol. 133, pp. 6497-6500 (2011).
Stafford et al., "Identification and Structure-Activity Studies of Novel Ultrashort-Acting Benzodiazepine Receptor Agonists," Bioorganic and Medicinal Chemistry Letters, 2002, vol. 12, 3215-3218.
Stahl, "Handbook of Pharmaceutical Salts," (2002), pp. 263-265, 272, 273, 280 and 281.
Stahl, et al., "Handbook of Pharmaceutical Salts: Properties, Selection. and Use," 2002, 164-167 and 272-273.
Teisuke Okano, Shin Yakuzaigaku Soron (revised 3rd Edit.), Nankodo Co., Ltd., Apr. 10, 1987, pp. 257-258, 226, 111, 256-225.
Thompson, Diane 0., "Cyclodextrins-Enabling Excipients: Their Present and Future Use in Pharmaceuticals," Critical Reviews in Therapeutic Drug Carrier Systems. 1997, vol. 14(1), 1-108.
Tsiakitzis, et al., "Novel Compounds Designed as Antistress Agents," Journal of Medicinal Chemistry, vol. 52, 2009, 7315-7318.
U.S. Non-Final Office Action dated Mar. 24, 2017 in U.S. Appl. No. 14/948,889.
U.S. Notice of Allowance on U.S. Appl. No. 14/948,889 dated Aug. 16, 2017.
Wermuth, C.G, (Publisher), Saishin Soyaku, second half volume, Technomics K.K., Sep. 25, 1999, pp. 347-365 and 452-453, (chapter by Anderson & Flora).
Wipf, P. "1. Basic Principles, ID Oxidation Reactions", Apr. 2, 2006, XP002563124; Retrieved from the Internet URL: ccc.chem. pitt.edu!wipf/Courses/2320_6-file; 2nd. Slide, pp. 1, 5, 7.
Zhao, M. et al. , "Oxidation of Primary Alcohols to Carboxylic Acids with Sodium Chlorite Catalyzed by TEMPO and Bleach," Journal of Organic Chemistry, vol. 64, pp. 2564-2566 (1999).

Light Polarised Microscopy: 100mg batch LJC-039-037-1

Data File L:\HPLC\HPLC2\DATA\PROJ_129\14-03-~1\PURITY06.D  Sample Name: LJC-039-081-1

| | | | |
|---|---|---|---|
| Injection Date | : 14/03/2005 16:48:47 PM | Seq. Line : | 3 |
| Sample Name | : LJC-039-081-1 | Location : | Vial 32 |
| Acq. Operator | : Colin Tiernan | Inj : | 2 |
| Acq. Instrument | : Instrument 2 | Inj Volume : | 5 μl |
| Acq. Method | : C:\HPCHEM\1\METHODS\P129_02.M | | |
| Last changed | : 14/03/2005 09:01:14 PM by Colin Tiernan | | |
| Analysis Method | : K:\HPCHEM\1\,METHODS\P129_02.M | | |
| Last changed | : 08/04/2005 14:03:14 PM | | |

Project 129 Analytical method

Mobile Phase A = 2mM ammonium hydrogen carbonate, pH 10 with ammonia solution
Mobile phase B = 100% Acetonitrile
Gradient:
10% B to 90% B in 25 mins
Hold for 5 minutes to re-equilibrate
Flow rate = 0.8 ml/min
Wavelength = 254nm

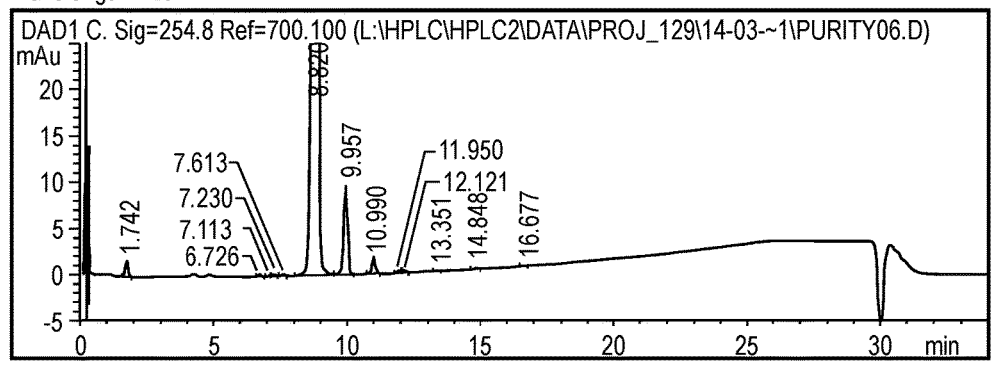

Area Percent Report

Sorted By       :  Retension Time
Multiplier      :  1.0000
Dilution        :  1.0000
Use Multiplier & Dilution Factor with ISTDs Signal 1: DAD1 C, Sig=254,8 Ref=700,100

| Peak # | Ret Time (min) | Sig | Type | Area (mAU's) | Height (mAU) | Area % |
|---|---|---|---|---|---|---|
| 1 | 1.742 | 1 | MM | 12.41115 | 1.57202 | 0.1930 |
| 2 | 6.726 | 1 | MM | 1.40011 | 1.77132e-1 | 0.0218 |
| 3 | 7.143 | 1 | MF | 9.49268e-1 | 1.38885e-1 | 0.0148 |
| 4 | 7.230 | 1 | FM | 1.48644 | 1.81698e-1 | 0.0231 |
| 5 | 7.613 | 1 | MM | 1.75318 | 1.90096e-1 | 0.0273 |
| 6 | 8.820 | 1 | MF | 6294.11816 | 666.39398 | 97.8578 |
| 7 | 9.957 | 1 | FM | 94.62333 | 9.52401 | 1.4712 |
| 8 | 10.990 | 1 | MM | 17.34299 | 1.72805 | 0.2696 |
| 9 | 11.950 | 1 | MF | 2.95212 | 3.17997e-1 | 0.0459 |
| 10 | 12.121 | 1 | FM | 2.33667 | 2.66796e-1 | 0.0363 |
| 11 | 13.351 | 1 | MM | 7.73216e-1 | 8.76126e-2 | 0.0120 |
| 12 | 14.848 | 1 | MM | 9.73962e-1 | 8.71620e-2 | 0.0151 |
| 13 | 16.677 | 1 | MM | 7.81046e-1 | 6.60149e-2 | 0.0121 |

Totals:                                   6431.90163    680.73246

Instrument 1  08/04/2005  14:04:22 PM
Results obtained with enhanced integrator

Figure 15C

Data File L:\HPLC\HPLC2\DATA\PROJ_129\21-03-~1\PURITY16.D
Sample Name: LJC-39-83-1

Injection Date     : 22/03/2005 02:44:02 PM         Seq. Line :  8
Sample Name        : LJC-39-83-1                    Location  : Vial 8
Acq. Operator      : Colin Tiernan                  Inj :  2
Acq. Instrument    : Instrument 2                   Inj Volume : 5 µl
Acq. Method        : C:\HPCHEM\1\METHODS\P129_02.M
Last changed       : 08/04/2005 14:54:50 PM
Analysis Method    : K:\HPCHEM\1\,METHODS\P129_02.M
Last changed       : 08/04/2005 14:54:50 PM
Project 129 Analytical method Mobile Phase A = 2mM ammonium hydrogen carbonate, pH 10 with ammonia solution
Mobile phase B = 100% Acetonitrile
Gradient:
10% B to 90% B in 25 mins
Hold for 5 minutes to re-equilibrate
Flow rate = 0.8 ml/min
Wavelength = 254nm

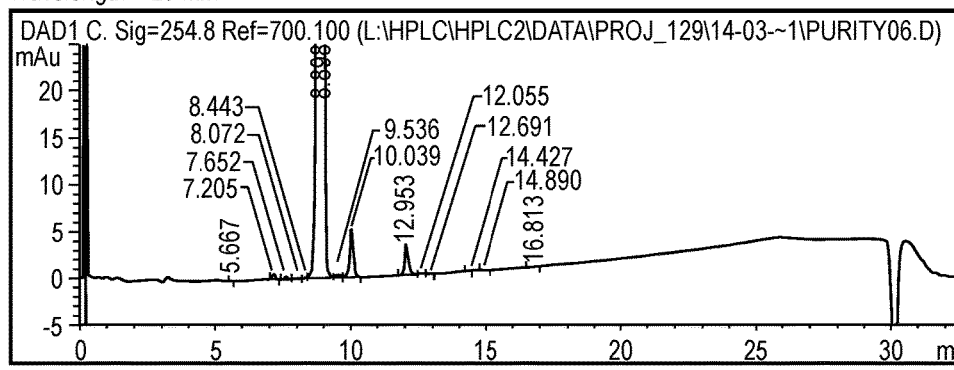

Area Percent Report

Sorted By      :  Retension Time
Multiplier     :  1.0000
Dilution       :  1.0000
Use Multiplier & Dilution Factor with ISTDs Signal 1: DAD1 C, Sig=254,8 Ref=700,100

| Peak # | Ret Time (min) | Sig | Type | Area (mAU's) | Height (mAU) | Area % |
|---|---|---|---|---|---|---|
| 1 | 5.667 | 1 | MM | 2.90224e-1 | 5.13708e-2 | 7.434e-3 |
| 2 | 7.205 | 1 | MM | 3.63391 | 4.65932e-1 | 0.0931 |
| 3 | 7.652 | 1 | MM | 1.82002 | 1.91653e-1 | 0.0466 |
| 4 | 8.072 | 1 | MM | 5.50713e-1 | 5.45034e-2 | 0.0141 |
| 5 | 8.433 | 1 | MF | 6.53709e-1 | 1.20260e-1 | 0.0167 |
| 6 | 8.898 | 1 | MF | 3811.41675 | 401.74905 | 97.6277 |
| 7 | 9.536 | 1 | MF | 2.24073 | 2.01594e-1 | 0.0574 |
| 8 | 10.039 | 1 | FM | 49.22905 | 5.02734 | 1.2610 |
| 9 | 12.055 | 1 | MM | 30.37308 | 3.10944 | 0.7780 |
| 10 | 12.691 | 1 | MF | 3.98861e-1 | 5.69501e-2 | 0.0102 |
| 11 | 12.953 | 1 | FM | 8.75666e-1 | 7.84943e-2 | 0.0224 |
| 12 | 14.427 | 1 | MM | 4.04565e-1 | 3.06551e-2 | 0.0104 |
| 13 | 14.890 | 1 | MM | 1.05645 | 1.08218e-1 | 0.0271 |
| 14 | 16.813 | 1 | MM | 1.08834 | 5.32132e-2 | 0.0279 |

Totals:                                   3904.03208     411.29868

Instrument 1  08/04/2005  14:55:54 PM
Results obtained with enhanced integrator

Figure 15D

Data File: c:\gilson\hplcme~1\c:22035a.002\c:22035a.gdt
Date acquired: Tue Mar 22 2005 12:47:04
Control Method: C:\GILSON\HPLCME~1\P129_01.GCT
Analysis Method: C:\GILSON\HPLCME~1\P129.GAN
Sample name: LJC-039-083-1 Injection Numer: 4 "Unknown"
Analyzed on Tue Apr 12 2005 15:12:38

Analysis Method Events
0.00   Disable Negative Peak Integration    Initial default
0.00   Peak Sensitivity 0.1
0.00   Peak Width 2.5                       Initial default
0.01   Inhibit Integration
7.00   Default Baseline                     Initial default
19.00  Enable Integration                   Initial default
30.00  Inhibit Integration
Channel Scales
<Auto range all channels>
data   -10.00 to 100.00 mV dt (0% o[cal]), Data rate: 20.00 (points/second)   <Analysis Channel>

Reporting
Area / Height Report (quanity by area)
Min area reported: 0
Include unnamed peaks
Include summary statistics for unknown group samples
Include individual values for unknown group samples
Include summary statistics for standard samples
Include individual values for standard samples Report Output
Save report to file
Save calibration summary
Save unknown summary
Print: <nothing>
Print Calibartion: <nothing>

Peak Analysis Error Conditions

Background Blank Removal
<None>

Track peak retention time

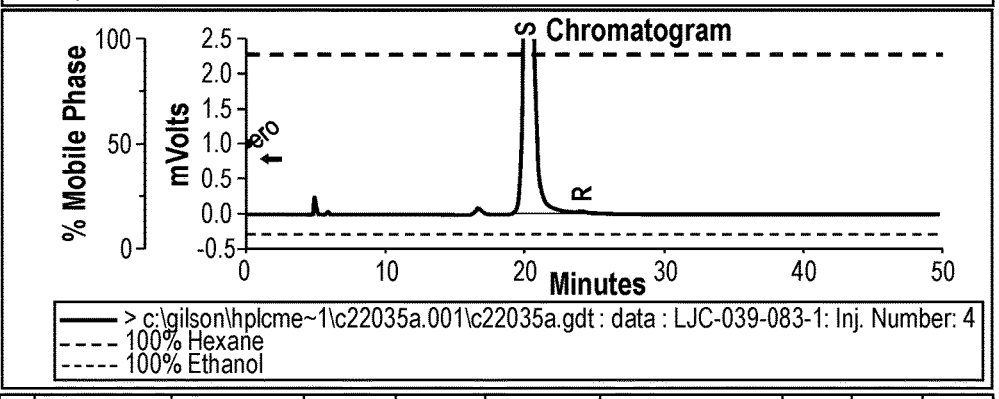

| | Inj. Number | Peak Name | R. Time | Area % | Area | Sample Descrip. | | | |
|---|---|---|---|---|---|---|---|---|---|
| 1 | 4.00 | S | 20.23 | 99.16 | 459828.81 | LJC-039-083-1 | | | |
| 2 | 4.00 | R | 23.71 | 0.84 | 3899.01 | LJC-039-083-1 | | | |

Figure 16D

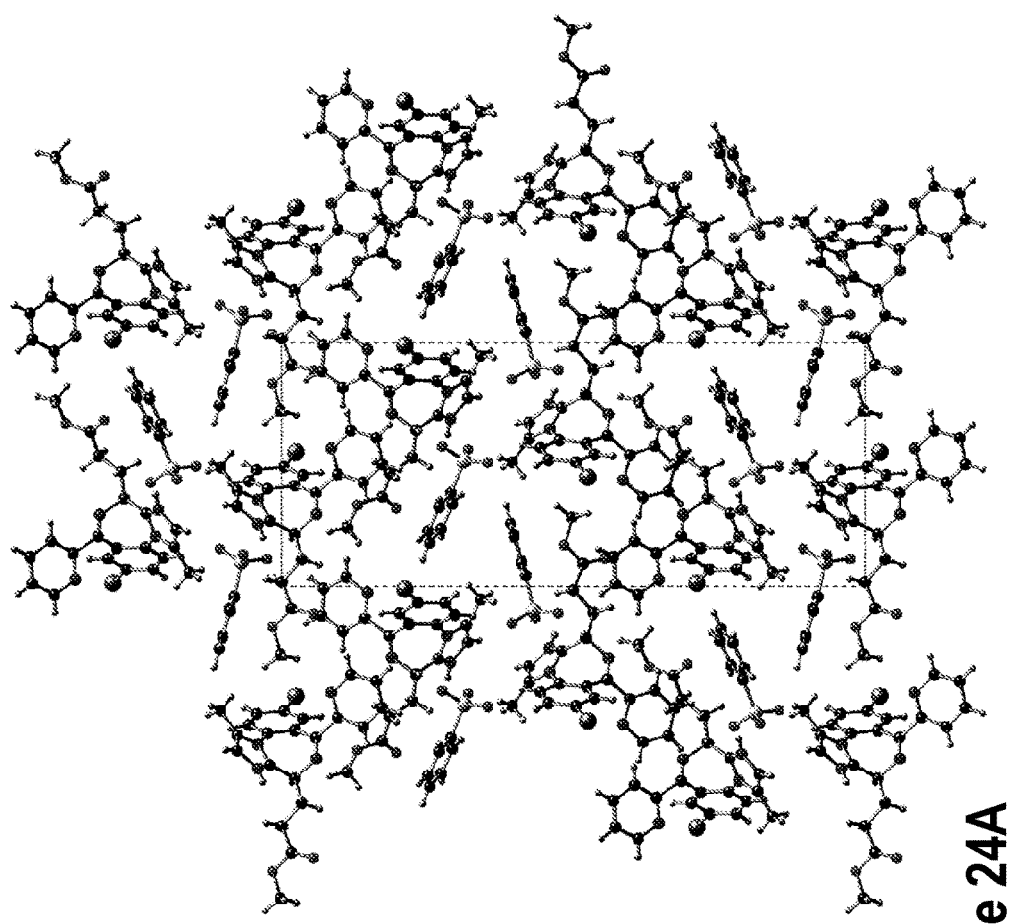
Figure 24A

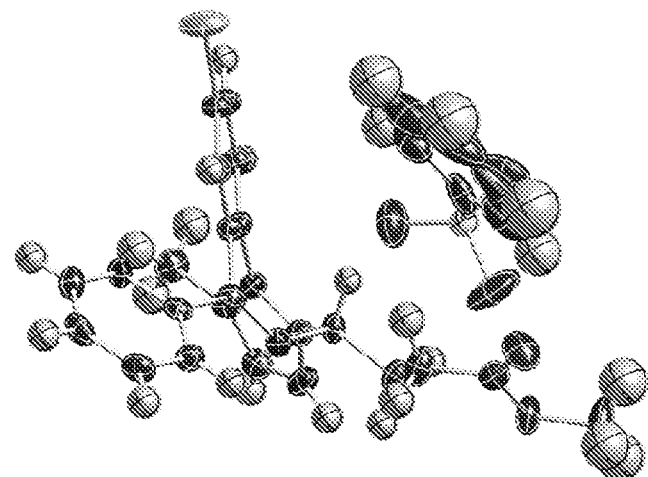
Figure 29
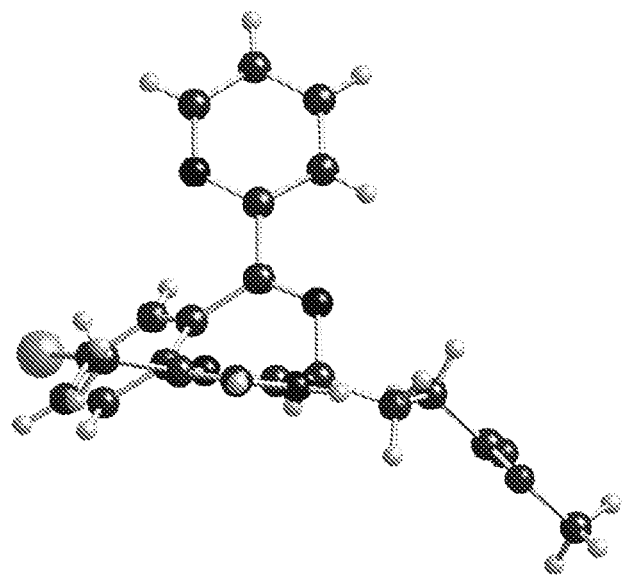
Figure 30

SHORT-ACTING BENZODIAZEPINE SALTS AND THEIR POLYMORPHIC FORMS

CROSS-REFERENCES TO RELATED APPLICATIONS

This application is a continuation of U.S. application Ser. No. 14/948,889, filed Nov. 23, 2015, now U.S. Pat. No. 9,777,007, which is a continuation of U.S. application Ser. No. 12/373,472, filed Nov. 2, 2009, now U.S. Pat. No. 9,193,730, which is the U.S. National Stage of International Application No. PCT/GB2007/002565, filed Jul. 10, 2007, which designated the United States and has been published as International Publication No. WO 2008/007071 and which claims the priority of Great Britain Patent Applications, Serial Nos.: 0613694.9 and 0613692.3 of Jul. 10, 2006, pursuant to 35 U.S.C. 119(a)-(d). The contents of the aforementioned applications are hereby incorporated by reference.

BACKGROUND OF THE INVENTION

This invention relates to salts of a short acting benzodiazepine, and to use of the salts as medicaments, in particular for sedative or hypnotic, anxiolytic, muscle relaxant, or anticonvulsant purposes.

European Patent No. 1,183,243 describes short-acting benzodiazepines that include a carboxylic acid ester moiety and are inactivated by non-specific tissue esterases. An organ-independent elimination mechanism is predicted to be characteristic of these benzodiazepines, providing a more predictable and reproducible pharmacodynamic profile. The compounds are suitable for therapeutic purposes, including sedative-hypnotic, anxiolytic, muscle relaxant and anticonvulsant purposes. The compounds are short-acting CNS depressants that are useful to be administered intravenously in the following clinical settings: preoperative sedation, anxiolysis, and amnestic use for perioperative events; conscious sedation during short diagnostic, operative or endoscopic procedures; as a component for the induction and maintenance of general anesthesia, prior and/or concomitant to the administration of other anaesthetic or analgesic agents; ICU sedation.

One of the compounds disclosed in EP 1,183,243 (in Example Ic-8, page 36) is Methyl 3-[(4S)-8-bromo-1-methyl-6-(2-pyridinyl)-4H-imidazol [1,2-a][1,4]benzodiazepin-4-yl] propanoate, as shown in formula (I) below:

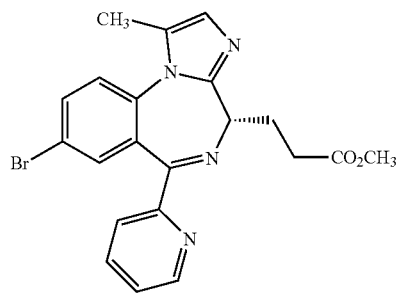

(I)

Whilst the free base of formula (I) is stable when stored at 5° C., samples stored at 40° C./75% relative humidity (open) are observed to deliquesce, become yellow to orange in colour, and show notable decreases in content relative to initial (see Example 1 below).

It has now surprisingly been found that the compound of formula (I) forms highly crystalline mono (benzenesulfonic acid) besylate salts that are easily isolated from a range of pharmaceutically acceptable solvents and show good thermal stability, low hygroscopicity and high aqueous solubility.

SUMMARY OF THE INVENTION

According to the invention there is provided a besylate salt of a compound of formula (I). Preferably the salt is a crystalline salt. Preferably the crystalline salt has a stoichiometry of 1:1 compound of formula (I):besylate. Preparation and characterisation of polymorphic forms of besylate salts is described in the Examples below.

According to the invention there is provided a crystalline polymorph of a besylate salt of a compound of formula (I) (herein designated besylate Form 1), that exhibits an X-ray powder diffraction (XRPD) pattern which comprises a characteristic peak at about 7.3, 7.8, 9.4, 12.1, 14.1, 14.4, 14.7, or 15.6 degrees two-theta.

Preferably the besylate Form 1 crystalline polymorph exhibits an XRPD pattern which comprises characteristic peaks at about 7.3, 7.8, 9.4, 12.1, 14.1, 14.4, 14.7, and 15.6 degrees two-theta.

More preferably the besylate Form 1 crystalline polymorph exhibits an XRPD pattern which comprises characteristic peaks at: 7.25 (10.60), 7.84 (72.60), 9.36 (12.10), 12.13 (32.50), 14.06 (48.50), 14.41 (74.30), 14.70 (50.70), 15.60 (26.90) [angle two-theta degrees (percentage relative intensity)].

Preferably the besylate Form 1 crystalline polymorph has a differential scanning calorimetry (DSC) onset melting temperature in the range 187-204° C., preferably about 191-192° C.

A crystal structure of Form 1 has been resolved at 190K (R factor of 6.3). Form I has a stoichiometry of 1:1 compound:besylate. Its crystallographic asymmetric unit contains two independent compound molecules and two besylate molecules. The two independent compound molecules are singly protonated on the imidazole ring. The crystal structure has unit cell dimensions of a=7.6868 Å, b=29.2607 Å, c=12.3756 Å, α=90°, β=97.7880°, γ=90°, and a space group of P2$_1$. The crystal structure is described in more detail in Example 9, and crystallographic coordinates are given in Table 17. Bond lengths and angles for Form 1 are given in Tables 19 and 20, respectively.

According to the invention there is provided a besylate salt of a compound of formula (I) which is a crystalline polymorph comprising a crystal with unit cell dimensions of a=7.6868 Å, b=29.2607 Å, c=12.3756 Å, α=90°, β=97.7880°, γ=90°.

There is also provided according to the invention a besylate salt of a compound of formula (I) which is a crystalline polymorph having a crystal structure defined by the structural coordinates as shown in Table 17.

There is further provided according to the invention a besylate salt of a compound of formula (I) with bond lengths and angles as shown in Tables 19 and 20, respectively.

There is further provided according to the invention a crystalline polymorph of a besylate salt of a compound of formula (I) (herein designated besylate Form 2), that exhibits an XRPD pattern which comprises a characteristic peak at about 8.6, 10.5, 12.0, 13.1, 14.4, or 15.9 degrees two-theta.

Preferably the besylate Form 2 crystalline polymorph exhibits an XRPD pattern which comprises characteristic peaks at about 8.6, 10.5, 12.0, 13.1, 14.4, and 15.9 degrees two-theta.

More preferably the besylate Form 2 crystalline polymorph exhibits an XRPD pattern which comprises characteristic peaks at: 8.64 (17.60), 10.46 (21.00), 12.03 (22.80), 13.14 (27.70), 14.42 (11.20), 15.91 (100.00) [angle two-theta degrees (percentage relative intensity)].

Preferably the besylate Form 2 crystalline polymorph has a differential scanning calorimetry (DSC) onset melting temperature in the range 170-200° C., preferably about 180° C.

A crystal structure of Form 2 has been resolved at 190K (R factor of 3.8). Form 2 has stoichiometry of 1:1 compound:besylate. Its crystallographic asymmetric unit contains one compound molecule and one besylate molecule. The compound molecule is singly protonated on the imidazole ring. The crystal structure has unit cell dimensions of a=8.92130 Å, b=11.1536 Å, c=25.8345 Å, $\alpha$=90°, $\beta$=90°, $\gamma$=90°, and a space group of $P2_12_12_1$. The crystal structure is described in more detail in Example 10, and crystallographic coordinates are given in Table 18. Bond lengths and angles for Form 2 are given in Tables 21 and 22, respectively.

According to the invention there is provided a besylate salt of a compound of formula (I) which is a crystalline polymorph comprising a crystal with unit cell dimensions of a=8.92130 Å, b=11.1536 Å, c=25.8345 Å, $\alpha$=90°, $\beta$=90°, $\gamma$=90°.

There is also provided according to the invention a besylate salt of a compound of formula (I) which is a crystalline polymorph having a crystal structure defined by the structural coordinates as shown in Table 18.

There is further provided according to the invention a besylate salt of a compound of formula (I) with bond lengths and angles as shown in Tables 21 and 22, respectively.

There is further provided according to the invention a crystalline polymorph of a besylate salt of a compound of formula (I) (herein designated besylate Form 3), that exhibits an X-ray powder diffraction (XRPD) pattern which comprises a characteristic peak at about 7.6, 11.2, 12.4, 14.6, 15.2, 16.4, or 17.7 degrees two-theta.

Preferably the besylate Form 3 crystalline polymorph exhibits an XRPD pattern which comprises characteristic peaks at about: 7.6, 11.2, 12.4, 14.6, 15.2, 16.4, and 17.7 degrees two-theta.

More preferably the besylate Form 3 crystalline polymorph exhibits an XRPD pattern which comprises characteristic peaks at: 7.61 (65.70), 11.19 (33.20), 12.38 (48.70), 14.63 (30.60), 15.18 (33.20), 16.40 (29.60), 17.68 (51.30) [angle 2θ° (percentage relative intensity)].

Preferably the besylate Form 3 crystalline polymorph has a differential scanning calorimetry (DSC) onset melting temperature in the range 195-205° C., preferably about 200-201° C.

There is further provided according to the invention a crystalline polymorph of a besylate salt of a compound of formula (I) (herein designated besylate Form 4), that exhibits an XRPD pattern which comprises a characteristic peak at about 7.6, 10.8, 15.2, 15.9, or 22.0 degrees two-theta.

Preferably the besylate Form 4 crystalline polymorph exhibits an XRPD pattern which comprises characteristic peaks at about: 7.6, 10.8, 15.2, 15.9, and 22.0 degrees two-theta.

Preferably the besylate Form 4 crystalline polymorph exhibits an XRPD pattern which comprises characteristic peaks at: 7.62 (83.50), 10.75 (14.70), 15.17 (37.80), 15.85 (28.70), 22.03 (100) [angle 2θ° (percentage relative intensity)].

Preferably the besylate Form 4 crystalline polymorph has a differential scanning calorimetry (DSC) onset melting temperature in the range 180-185° C., preferably about 182° C.

A preferred salt is the besylate Form 1 based on the robustness of formation, yield, purity and chemical and solid form stability.

There is also provided according to the invention a method of making a besylate salt of a compound of formula (I), which comprises reacting a free base of a compound of formula (I) with benzene sulfonic acid.

Also according to the invention there is provided a method of making a salt of the invention, which comprises contacting a free base of a compound of formula (I) with benzene sulfonic acid in solution to cause formation of a precipitate of the besylate salt. Preferably the method further comprises isolating the precipitate.

Preferably the free base is dissolved in toluene, ethanol, ethyl acetate, MtBE, dichloromethane (DCM), isopropyl acetate, ethyl formate, methanol, or acetone. More preferably the free base is dissolved in toluene or ethyl acetate. Preferably the benzene sulfonic acid is dissolved in ethanol.

The besylate Form 1 may be prepared by contacting a solution of a free base of a compound of formula (I) in toluene, ethyl acetate, acetone, isopropyl acetate, or ethyl formate with a solution of benzene sulfonic acid in ethanol to cause formation of a precipitate of the salt.

There is also provided according to the invention a besylate salt of a compound of formula (I) which is obtainable by the above method.

The besylate Form 2 may be prepared by contacting a solution of a free base of a compound of formula (I) in methanol with a solution of benzene sulfonic acid in ethanol to cause formation of a precipitate of the salt. Preferably the mixture is cooled below ambient temperature (for example 4° C.).

There is also provided according to the invention a besylate salt of a compound of formula (I) which is obtainable by the above method.

The besylate Form 3 may be prepared by seeding liquor resulting from crystallisation of Form 1 from ethyl acetate/ethanol with Form 1. Preferably the liquor is cooled below ambient temperature (for example 4° C.).

In one embodiment the besylate Form 3 may be prepared by seeding, with a besylate Form 1 crystalline salt of a compound of formula (I), a filtrate solution separated from the precipitate formed by contacting a solution of a compound of formula (I) in ethyl acetate with a solution of benzene sulfonic acid in ethanol, to produce the besylate Form 3 crystalline polymorph.

There is also provided according to the invention a besylate salt of a compound of formula (I) which is obtainable by any of the above methods.

The besylate Form 4 may be prepared by re-crystallising besylate Form 1 from isopropyl acetate/ethanol, preferably 40% isopropyl acetate/ethanol.

There is also provided according to the invention a besylate salt of a compound of formula (I) which is obtainable by the above method.

Salts of the invention may also be prepared by crystallising compound of formula (I) besylate from a suitable solvent, or from a suitable solvent/anti-solvent or solvent/co-solvent mixture. The solution or mixture may be cooled and/or evaporated to achieve crystallisation if appropriate.

We have found that crystallisation of Form 2 is observed in conditions where there are extremes of either polarity (for example acetonitrile:water) or lipophilicity (n-nonane), or both (dimethyl sulfoxide:1,2-dichlorobenzene).

Examples of solvents for crystallisation of Form 2 are: nonane; methanol.

Examples of solvent/anti-solvent mixtures for crystallisation of Form 1 are: di methylacetamide/methyl isobutyl ketone; dimethylacetamide/tetrachloroethylene; acetonitrile/3-methylbutan-1-ol; acetonitrile/1,2-dichlorobenzene; acetonitrile/pentylacetate; methanol/3-methylbutan-1-ol; methanol/methyl isobutyl ketone; 2,2,2-trifluoroethanol/1,4-dimethylbenzene; ethanol/methyl isobutyl ketone; ethanol/1,4-dimethylbenzene; propan-1-ol/1,2-dichlorobenzene; propan-1-ol/tetrachloroethylene; propan-2-ol/1,2-dichlorobenzene; propan-2-ol/n-nonane; 2-methoxy ethanol/water; 2-methoxy ethanol/pentyl acetate; 2-methoxy ethanol/1,4-dimethylbenzene; tetrahydrofuran/water; tetrahydrofuran/3-methylbutan-1-ol; tetrahydrofuran/1,2-dichlorobenzene; tetrahydrofuran/ethyl acetate; tetrahydrofuran/1,3-dimethylbenzene.

Examples of solvent/anti-solvent mixtures for crystallisation of Form 2 are: ethanol/ethyl acetate; ethanol/methyl isobutyl ketone; ethanol/p-cymene; dimethylsulfoxide/1,2-dichlorobenzene; acetonitrile/water; ethano/1,2-dichlorobenzene; ethanol/tetrachloroethylene; tetrahydrofuran/1,2-dichlorobenzene; tetrahydrofuran/ethyl acetate.

According to a preferred embodiment, Form 1 is crystallised from 2-methoxyethanol/pentyl acetate.

According to a preferred embodiment, Form 2 is crystallised from ethanol/ethyl acetate.

According to a preferred embodiment, Form 2 is crystallised from methanol/ethanol (preferably by cooling a solution of compound of formula (I) besylate in methanol/ethanol below ambient temperature, for example 4° C.).

According to a preferred embodiment, Form 3 is crystallised from ethanol/ethyl acetate (suitably by cooling the mixture below ambient temperature, for example 4° C.).

According to a preferred embodiment, Form 4 is crystallised from isopropyl acetate/ethanol (preferably by cooling a solution of compound of formula (I) besylate in isopropyl acetate/ethanol to ambient temperature).

There is also provided according to the invention a besylate salt of a compound of formula (I) obtainable by any of the above methods.

Methods of preparing salts of the invention are described in detail in the Examples below.

A salt of the invention may be used as a medicament, in particular for sedative or hypnotic, anxiolytic, muscle relaxant, or anticonvulsant purposes.

While it is possible for a salt of the invention to be administered as a bulk active chemical, it is preferably provided with a pharmaceutically acceptable carrier, excipient, or diluent in the form a pharmaceutical composition. The carrier, excipient, or diluent must, of course, be acceptable in the sense of being compatible with the other ingredients of the composition and must not be deleterious to the recipient.

Accordingly, the present invention provides a pharmaceutical composition comprising a salt of the invention and a pharmaceutically acceptable carrier, excipient, or diluent.

Pharmaceutical compositions of the invention include those suitable for oral, rectal, topical, buccal (e.g. sublingual) and parenteral (e.g. subcutaneous, intramuscular, intradermal or intravenous) administration.

Preferably a salt of the invention is provided in the form of a pharmaceutical composition for parenteral administration, for example, by intravenous or intramuscular injection of a solution. Where the pharmaceutical composition is for parenteral administration, the composition may be an aqueous or non-aqueous solution or a mixture of liquids, which may include bacteriostatic agents, antioxidants, buffers or other pharmaceutically acceptable additives.

A preferred formulation of a salt of the invention is in an aqueous acidic medium of pH 2-4 or in an aqueous solution of a cyclodextrin (CD). Cyclodextrins that can be used for these formulations are either the anionically charged sulfobutylether (SBE) derivatives of β-CD, specifically SBE7-β-CD, marketed under the tradename Captisol by CyDex, Inc. (Critical Reviews in Therapeutic Drug Carrier Systems, 14 (1), 1-104 (1997)), or the hydroxypropyl CD's.

A further preferred formulation of a salt of the invention is a lyophilised formulation comprising, in addition to the salt, at least one of the following agents: ascorbic acid, citric acid, maleic acid, phosphoric acid, glycine, glycine hydrochloride, succinic acid or tartaric acid. These agents are believed to be useful as buffering, caking or vizualisation agents. In some cases it may be beneficial to include sodium chloride, mannitol, polyvinylpyrrolidone, or other ingredients in the formulation.

The preferred method of formulation (i.e., acid buffer or CD-based) may depend on the physicochemical properties (e.g., aqueous solubility, pKa, etc.) of a particular salt. Alternatively the salt may be presented as a lyophilized solid for reconstitution with water (for injection) or a dextrose or saline solution. Such formulations are normally presented in unit dosage forms such as ampoules or disposable injection devices. They may also be presented in multi-dose forms such as a bottle from which the appropriate dose may be withdrawn. All such formulations should be sterile.

According to the invention there is provided a method for producing sedation or hypnosis in a subject, which comprises administering an effective sedative or hypnotic amount of a salt of the invention to the subject.

There is also provided according to the invention a method for inducing anxiolysis in a subject, which comprises administering an effective anxiolytic amount of a salt of the invention to the subject.

There is further provided according to the invention a method for inducing muscle relaxation in a subject, which comprises administering an effective muscle relaxant amount of a salt of the invention to the subject.

There is further provided according to the invention a method for treating convulsions in a subject, which comprises administering an effective anticonvulsant amount of a salt of the invention to the subject.

According to the invention there is also provided use of a sedative or hypnotic amount of a salt of the invention in the manufacture of a medicament for producing sedation or hypnosis in a subject.

According to the invention there is also provided a salt of the invention for producing sedation or hypnosis in a subject.

There is also provided according to the invention use of an anxiolytic amount of a salt of the invention in the manufacture of a medicament for producing anxiolysis in a subject.

There is also provided according to the invention a salt of the invention for producing anxiolysis in a subject.

There is further provided according to the invention use of a muscle relaxant amount of a salt of the invention in the manufacture of a medicament for producing muscle relaxation in a subject.

There is further provided according to the invention a salt of the invention for producing muscle relaxation in a subject.

There is further provided according to the invention use of an anticonvulsant amount of a salt of the invention in the manufacture of a medicament for treating convulsions in a subject.

There is further provided according to the invention a salt of the invention for treating convulsions in a subject.

The subject is suitably a mammal, preferably a human.

A suitable pharmaceutical parenteral preparation for administration to humans will preferably contain 0.1 to 20 mg/ml of a salt of the invention in solution or multiples thereof for multi-dose vials.

Intravenous administration can take the form of bolus injection or, more appropriately, continuous infusion. The dosage for each subject may vary, however, a suitable intravenous amount or dosage of a salt of the invention to obtain sedation or hypnosis in a mammal would be 0.01 to 5.0 mg/kg of body weight, and more particularly, 0.02 to 0.5 mg/kg of body weight, the above being based on the weight of the salt which is the active ingredient. A suitable intravenous amount or dosage of a salt of the invention to obtain anxiolysis in a mammal would be 0.01 to 5.0 mg/kg of body weight, and more particularly, 0.02 to 0.5 mg/kg of body weight, the above being based on the weight of the salt which is the active ingredient. A suitable intravenous amount or dosage of a salt of the invention to obtain muscle relaxation in a mammal would be 0.01 to 5.0 mg/kg of body weight, and more particularly, 0.02 to 0.5 mg/kg of body weight, the above being based on the weight of the salt which is the active ingredient. A suitable intravenous amount or dosage of a salt of the invention to treat convulsions in a mammal would be 0.01 to 5.0 mg/kg of body weight, and more particularly, 0.02 to 0.5 mg/kg of body weight, the above being based on the weight of the salt which is the active ingredient.

Salts of the invention are short-acting CNS depressants that are useful to be administered intravenously in the following clinical settings: preoperative sedation, anxiolysis, and amnestic use for perioperative events; conscious sedation during short diagnostic, operative or endoscopic procedures; as a component for the induction and maintenance of general anaesthesia, prior and/or concomitant to the administration of other anaesthetic or analgesic agents; ICU sedation.

BRIEF DESCRIPTION OF THE DRAWINGS

Preferred embodiments of the invention are described in the following Examples with reference to the accompanying drawings in which:

FIG. 11A) XRPD for 100 mg batch LJC-039-037-1; FIG. 11B) DSC for 100 mg batch LJC-039-037-1; FIG. 11C) TGA for 100 mg batch LJC-039-037-1; FIG. 11D) 1H NMR for 100 mg batch LJC-039-037-1; FIG. 11E) GVS for 100 mg batch LJC-039-037-1; FIG. 11F) XRPD post GVS for 100 mg batch LJC-039-037-1; FIG. 11G) XRPD post stability at 40° C./75% RH for 100 mg batch LJC-039-037-1; FIG. 11H) VT XRPD for 100 mg batch LJC-039-037-1; FIG. 11I) light polarised microscopy for 100 mg batch LJC-039-037-1;

FIG. 12A) XRPD for 100 mg batch LJC-039-067-8; FIG. 12B) DSC for 100 mg batch LJC-039-067-8; FIG. 12C) DSC with ramp rate of 2° C./min; FIG. 12D) $^1$H NMR for LJC-039-067-8;

FIG. 13A) XRPD for LJC-039-081-2 ($2^{nd}$ crop from liquors of LJC-039-081-1); FIG. 13B) DSC for LJC-039-081-2; FIG. 13C) DSC for LJC-039-081-2 (2° C./min ramp rate); FIG. 13D) TGA for LJC-039-081-2; FIG. 13E) $^1$H NMR for LJC-039-081-2; FIG. 13F) GVS for LJC-039-081-2; FIG. 13G) XRPD post GVS for LJC-039-081-2;

FIG. 14A) XRPD for LJC-039-086-1; FIG. 14B) DSC for LJC-039-086-1; FIG. 14C) $^1$H NMR for LJC-039-086-1;

FIGS. 16A-16D show chiral chromatography for LJC-039-081-1, and LJC-039-083-1;

FIG. 24A-24C show crystal structure, determined by single-crystal X-ray diffraction of a crystal of compound of formula (I) besylate grown from 2-methoxyethanol:pentyl acetate solution, viewed along the crystallographic a axis (FIG. 24A), b axis (FIG. 24B), and c axis (FIG. 24C);

FIG. 29 shows molecular structure as determined by single-crystal X-ray diffraction of a crystal of compound of formula (I) besylate Form 2 with atoms represented by thermal ellipsoids. Only Hydrogens specifically located in the crystal structure are depicted;

FIG. 30 shows conformation adopted by the independent molecule in Form 2;

DETAILED DESCRIPTION OF PREFERRED EMBODIMENTS

Example 1

Solid-State Stability Study of Compound of Formula (I)
Method/Technique.

2 mg samples of compound of formula (I), accurately weighed, were placed in 4-mL clear glass screw-cap vials. Samples were tested at initial and after 34 days stored at 5° C./Ambient Relative Humidity (AMRH) Closed, 30° C./60% RH Closed, 40° C./75% RH Open and 60° C./AMRH Closed.

TABLE 1

| HPLC Method Condition | |
|---|---|
| Column: | |
| Phase = | Phenomenex Luna C18(2) |
| Length × i.d = | 100 × 4.6 mm |
| Particle size = | 3 μm |
| Mobile phase: | A = 1000:1 Water/Trifluoroacetic Acid |
| | B = 1000:0.5 Acetonitrile/Trifluoroacetic Acid |
| Flow rate: | 1.0 mL/min |
| Column Temperature: | 40° C. |
| Gradient | Time (min) | % A | % B |
| | 0.0 | 80 | 20 |
| | 20.0 | 20 | 60 |
| | 25.0 | 20 | 60 |
| | 25.1 | 80 | 20 |
| | 30.0 | 80 | 20 |
| Detection Wavelength: | 230 nm |
| Sample Mass Injected | μg, typically 1 μL injection of 1.0 mg compound of formula (I)/mL in 60:40 Water/Acetonitrile |
| Retention Times | Compound of formula (I) elutes at approximately 7.64 min |

Results
Appearance.
Table 2 lists the appearance results.

TABLE 2

Summary of Compound of Formula (I) Appearance Data

| Storage Condition | Timepoint days | Appearance |
|---|---|---|
| RT | initial | Cream to light yellow powder |
| 5 C./AMRH Closed | 34 | Cream to light yellow powder |
| 30 C./60% RH Closed | 34 | Cream to light yellow powder |
| 40 C./75% RH Open | 34 | Deliquesced yellow mass on bottom of vial |
| 60 C./AMRH Closed | 34 | Deliquesced dark yellow to orange mass on bottom of vial |

Compound of Formula (I) Content (% w/w).

The % w/w content values (see Table 3) show too much variability to detect differences between the initial value and those measured after 34 days at 5° C./AMRH Closed, 30° C./60% RH Closed or 40° C./75% RH Open. The average % w/w measured for the samples stored 34 days at 60° C./AMRH Closed show a 10% w/w decrease from the initial value.

Compound of Formula (I) Content (% Area).

Figure 1:
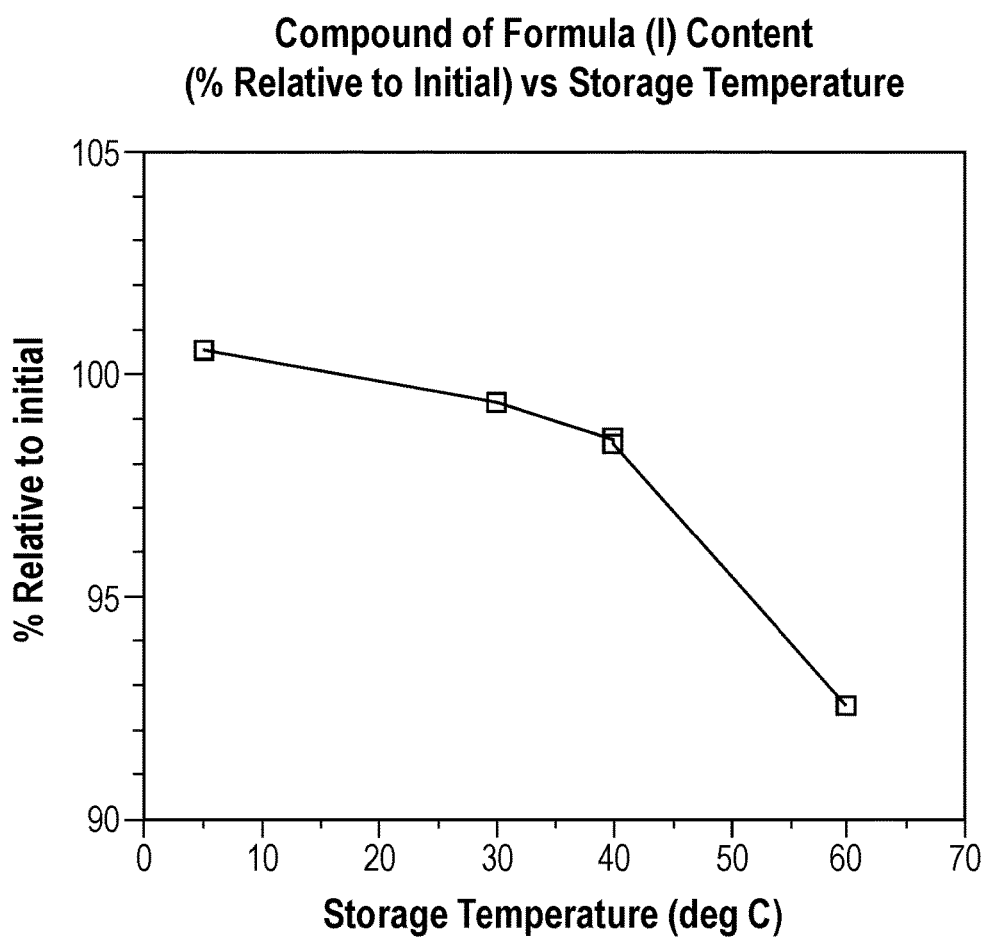
FIG. 1 shows a graph of compound of formula (I) content (% relative to initial) vs storage temperature.

The compound of formula (I) % area content (see Table 3 and FIG. 1) shows no significant change after 34 days stored at 5° C./AMRH Closed, but decreases steadily with increasing storage temperature for samples at 30° C./60% RH Closed, 40° C./75% RH Open or 60° C./AMRH Closed. Major degradation peaks are observed at RRT 0.68, 0.87 and RRT 0.90, but the chromatograms, which are relatively complex even at initial (23 peaks), also show many new small degradent peaks (e.g. 7 peaks at 30° C./60% RH Closed; 13-20 peaks at 60° C./AMRH Closed). These observations suggest multiple degradation pathways. The degradent at RRT 0.68 is tentatively identified as the ester hydrolysis product (the free acid of compound of formula (I)). It is most prevalent in the 40° C./75% RH Open samples, as would be expected for a hydrolysis product.

TABLE 3

Summary of Compound of Formula (I) HPLC Data

| | Timepoint | Compound of Formula (I) Content | | % Relative to Avg. Initial % |
|---|---|---|---|---|
| Storage Condition | Days | % w/w | % area | area |
| RT | initial | 100.5 | 95.14 | Avg = 94.81 |
| RT | initial | 104.1 | 94.47 | |
| 5 C./AMRH Closed#1[1] | 34 | 102.6 | 95.30 | 100.52 |
| 30 C./60% RH Closed #1[1] | 34 | 94.7 | 94.20 | 99.36 |
| 40 C./75% RH Open #1 | 34 | 105.4 | 93.45 | 98.57 |
| 40 C./75% RH Open #2 | 34 | 100.3 | 93.39 | 98.50 |
| 60 C./AMRH Closed #1 | 34 | 93.4 | 87.77 | 92.57 |
| 60 C./AMRH Closed #2 | 34 | 91.1 | 87.77 | 92.57 |

Notes
Only one sample was tested due to an autosampler sequencer error.

Conclusions

Compound of formula (I) is stable with respect to appearance and content for at least 34 days stored at 5° C./AMRH Closed. No change in appearance was noted at 30° C./60%

RH Closed, but an approximately 0.6% drop in compound of formula (I) content relative to the initial % area was observed. Samples stored at 40° C./75% RH Open or 60° C./AMRH Closed deliquesced, became yellow to orange in colour and showed notable decreases (1.5 to 8%) in compound of formula (I) content relative to initial. Major degradation peaks at RRT 0.68, 0.87 and RRT 0.90 are observed along with numerous smaller peaks, suggesting multiple degradation pathways. The degradent at RRT 0.68 is tentatively identified as the ester hydrolysis product. These results indicate that compound of formula (I) should be stored refrigerated for long term storage.

Example 2

The solubility of the compound of formula (I) was determined in a wide range of organic solvents. The solubility data is shown in Table 4 below.

TABLE 4

| Solvent | Min solvent required/mg/ml |
|---|---|
| Methanol | 446 |
| Ethanol | 324 |
| Propan-2-ol | 454 |
| Acetone | 214 |
| Toluene | 460 |
| Ethyl acetate | 218 |
| Tetrahydrofuran | 311 |
| Acetonitrile | 362 |

The data clearly shows that the compound of formula (I) has high solubility in common organic solvents. The preferred solvents are ethanol and toluene.

Two basic centres of the free base of the compound were measured for pKa. However, the basic centre of the pyridine ring had a pKa of 1.99. The pKa of the basic centre of the imidazole ring was measured to be 4.53.

Benzene sulfonic acid was used to produce a besylate salt of the compound of formula (I). Experiments were conducted on a 20 mg scale using 6 volumes of solvent. All reactions were carried out at ambient temperature with acids charged as stock solutions in ethanol (1M) or as solids depending on solubility.

Solids isolated showed significant peak shifts in $^1$H NMR to confirm salt formation. X-Ray Powder Diffraction (XRPD) showed that the salt had crystalline indication. Table 5 summarises the isolated salt form.

TABLE 5

| Entry | Salt | Solvent | ID |
|---|---|---|---|
| 1 | besylate | toluene | LJC-039-009-7 |

The salt was subsequently stored at 40° C./75% RH for two weeks then re-analysed by XRPD and HPLC for chemical purity to assess stability of the materials. The salt retained the same powder pattern after exposure to the humidity conditions, and also retained high chemical purity supporting improved stability.

It can be seen from the $T^1$ purity results of the isolated salt (Table 6 below) that the besylate salt from toluene showed high purity values before and after the stability study.

TABLE 6

Summary of purity before and after 40° C./75% RH for 1 week

| Entry | Salt | ID | Purity $T^0$/% | Purity $T^1$/% |
|---|---|---|---|---|
| 1 | besylate | LJC-039-009-7 | 95.9 | 95.9 |

The results above show that the besylate salt form showed high purity and favourable stability results.

Example 3

Scale up of the besylate salt to 100 mg was performed based on data in Example 2. Toluene was found to be the preferred solvent for isolating besylate salts.

Besylate Salt of Compound of Formula (I)

A scale up to 50 mg of input material was carried out in order to confirm whether or not the process would scale up, and to confirm that the material isolated was of the same crystalline form (Form 1) seen from the previous smaller scale experiment. Once the analysis confirmed the salt to be Form 1 and that the properties were in keeping with what was expected, another scale up was carried out with 100 mg of input material in order to carry out full characterisation and submit the sample for a 4 week stability study at 40° C./75% RH. Both the scaled up reactions were carried out in toluene with benzene sulfonic acid added as a solution in ethanol (1M).

Besylate Experimental Procedure

Compound of formula (I) free base (100 mg, batch 704-17) was charged to a vial and toluene (600 µl) was added at ambient temperature. To the solution benzene sulfonic acid (250 µl, 1M in ethanol) was added and the reaction mixture stirred for fifteen minutes, after which time a solid had precipitated from the solution which was filtered, washed with toluene and oven dried at 40° C. under vacuum. Analysis by XRPD showed the solid to be of identical powder pattern as other besylates generated, and the $^1$H NMR confirmed salt formation due to significant peak shifts.

TABLE 7

| Entry | ID | salt | GVS uptake/% | Onset melt/° C. | TGA weight loss/% | Solubility mg/ml | Chemical purity/% | Chiral purity/% e.e |
|---|---|---|---|---|---|---|---|---|
| 1 | LJC-039-037-1 | besylate | 2.0 | 201.3 | 4.9 | 8.3 | 97.1 | 94.4 |

The enantiomeric excess for LJC-039-037-1 was only 94.4 therefore the result was compared to another batch of besylate (LJC-039-081-1) that was isolated under identical conditions. The enantiomeric excess of this batch was 99.1%.

Process Optimisation

To improve further yields of besylate salt (Form 1) four solvents were screened (isopropyl acetate, ethyl formate, methanol and acetone). In total eight 100 mg scale reactions were conducted in these solvents with the relevant acid added as stock solution in ethanol for comparison to previous experiments.

Compound of formula (I) (batch 704-38, 100 mg) dissolved in solvent (600 µl) at ambient. Acid (250 µl, 1M stock solution in ethanol) added and all reaction mixtures stood for 48 hours at ambient. The results are summarised in Table 8.

TABLE 8

Results of process optimisation experiments

| Table entry | Lab book reference | Salt | Solvent | XRPD | Yield/% | Purity/% area | Purity post 40° C./75% RH for 4 weeks |
|---|---|---|---|---|---|---|---|
| 1 | LJC-039-067-2 | besylate | acetone | Form 1 | 38 | 98.4 | 98.1 |
| 2 | LJC-039-067-4 | besylate | iPrOAc | Form 1 | 79 | 97.7 | 95.9 |
| 3 | LJC-039-067-6 | besylate | Ethyl formate | Form 1 | 40 | 98.6 | 98.3 |
| 4 | LJC-039-067-8 | besylate | MeOH | Single crystals, Form 2 | Not recorded | 98.1 | Not recorded |

All reactions except that of besylate formation in methanol showed Form 1. The methanol reaction was stored at 4° C. The data obtained confirmed anhydrous besylate 1:1, and a powder pattern of the material confirmed the existence of a new form (Form 2).

It was concluded from the study that solvents such as isopropyl acetate increased the purity of the salts, however reduced the recovery. Because the previous choice of solvent (ethyl acetate) gave high yielding salts with high purity values, it was decided to use ethyl acetate for the final scale up experiments.

Besylate (Form 1) 1 g Scale-Up

Figure 3:
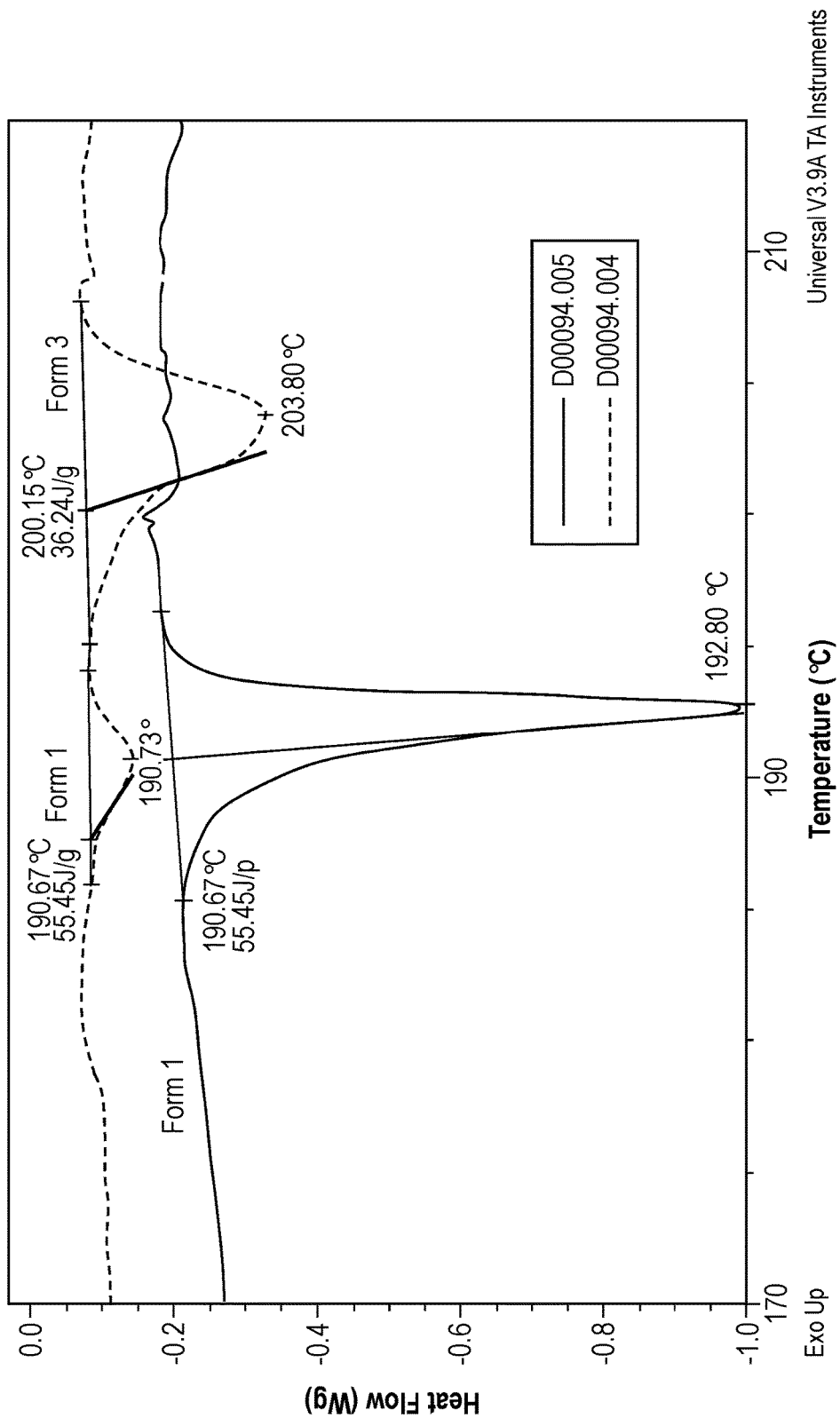
FIG. 3 shows DSC of LJC-039-081-1 (solid) overlaid with LJC-039-081-2 (dotted)

A 1 g formation of the besylate salt was carried out. This successfully produced 950 mg (70% yield) of Form 1. The liquors were highly coloured (yellow) and therefore seeded with a small amount of Form 1, to assist recovery. The liquors were stored at 4° C. for 16 hours. The solid obtained displayed a new powder pattern (Form 3). The solid was analysed by thermal analysis and variable temperature XRPD to confirm whether or not it was a true polymorph or a solvate. Interpretation of the analysis concluded it not to be a solvate from the $^1$H NMR evidence, and the DSC showed two endothermic events confirmed by hostage microscopy (FIG. 3). It was interpreted that the seeds of Form 1 melted at 187° C., with Form 3 melting at 200° C. The reason that Form 1 was not identified by XRPD is that this is a less sensitive technique than microscopy.

Form 3 precipitates at a lower temperature to Form 1.

Characterisation was carried out on the polymorphs to propose the relationship between them.

TABLE 9

Thermal data of besylate forms

| Entry | ID | Form | Onset of Melt/° C. | ΔH/Jg$^{-1}$ |
|---|---|---|---|---|
| 1 | LJC-039-081-1 | 1 | 201 | 56 |
| 2 | LJC-039-067-8 | 2 | 180 | 73 |
| 3 | LJC-039-081-2 | 1, 3 | 187, 200 | 7.6, 37 |

The lower melting point of the small amount of Form 1 present in LJC-039-081-2 can be potentially attributed to lower purity (97.2% compared with 97.9% in LJC-039-081-1).

Figure 4:
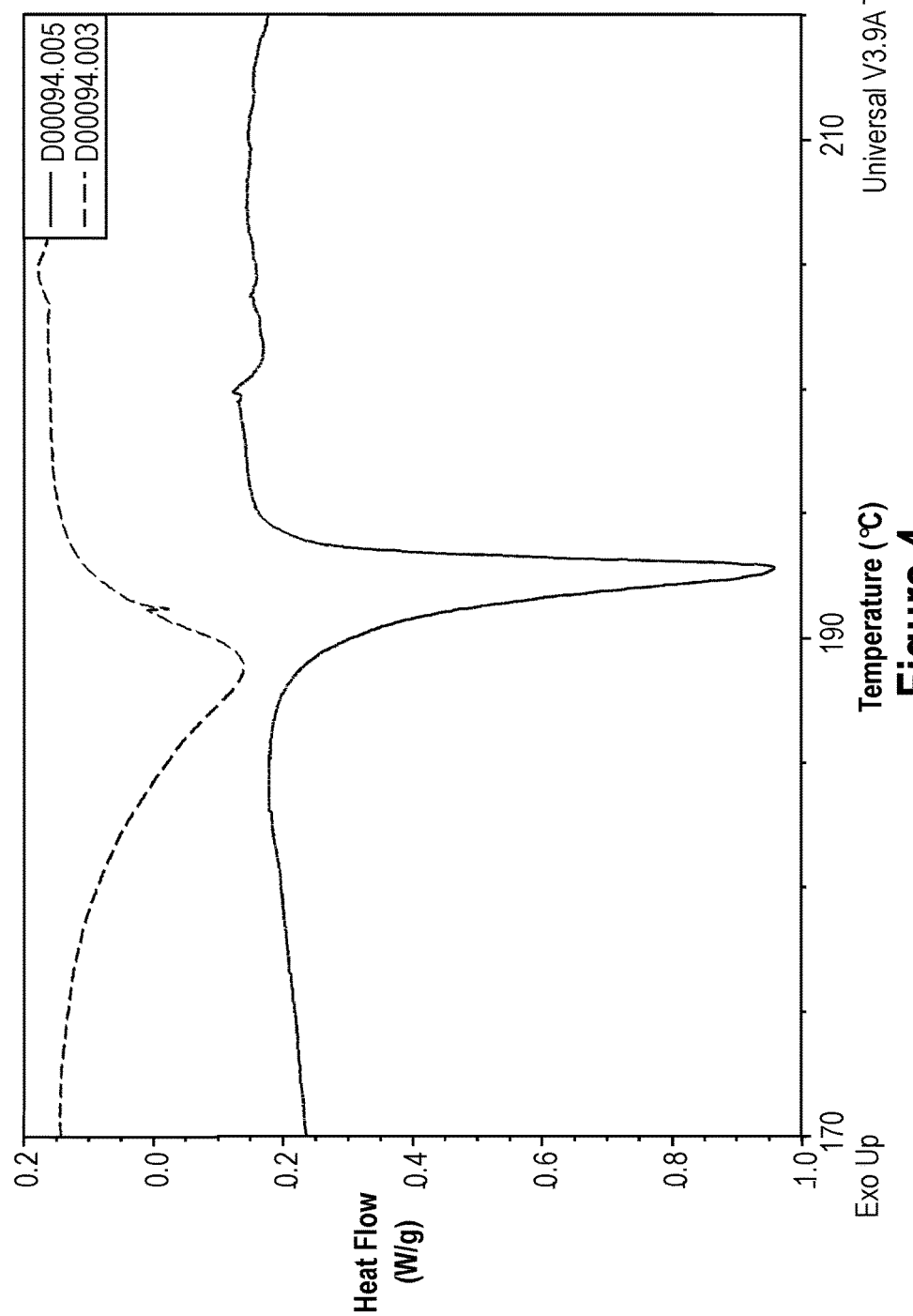
FIG. 4 shows DSC of besylate forms (Form 1 solid, Form 2 dashed)

FIG. 4 shows the DSC of besylate forms 1 (solid) and 2 (dashed).

Figure 5:
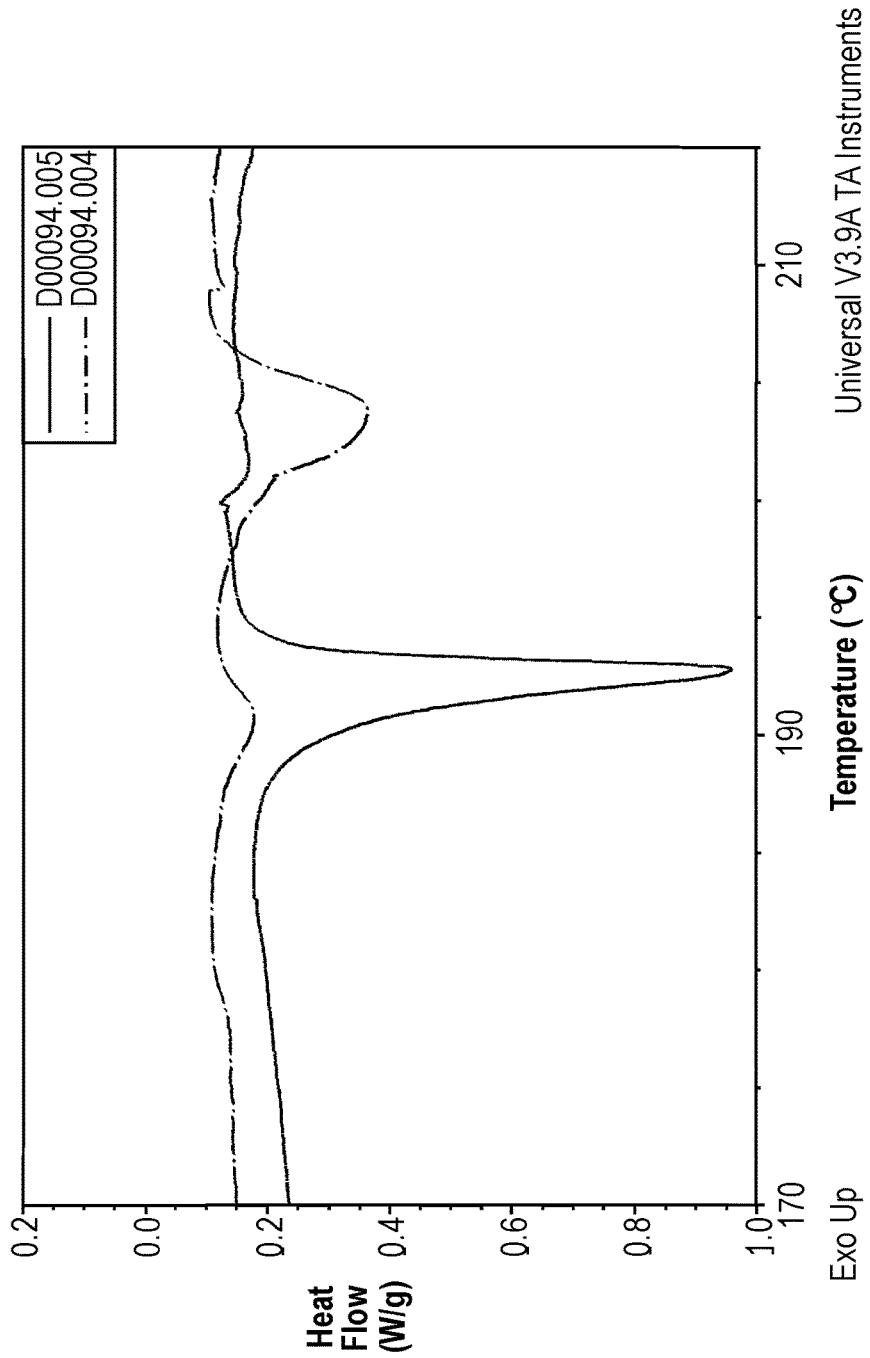
FIG. 5 shows DSC of besylate forms (Form 1 solid, Form 3 dotted and dashed)

FIG. 5 shows the DSC of besylate forms 1 (solid) and 3 (dotted and dashed).

Example 4

Salt Stability Studies

TABLE 10

Summary Table of salt purities after 4 week stability study

| Sample ID | salt | T$^0$ | T$^1$ | T$^2$ | T$^3$ | T$^4$ |
|---|---|---|---|---|---|---|
| LJC-039-037-1 | besylate | 97.1 | 97.3 | 97.4 | 96.7 | 96.7 |

Crystalline samples of besylate were stored at 40° C./75% RH for a total of four weeks and samples were taken for HPLC every seven days. The besylate hplc purity remained consistent up until T$^3$ when it reached 96.7%. This value did however remain consistent to T$^4$.

Figure 6A:
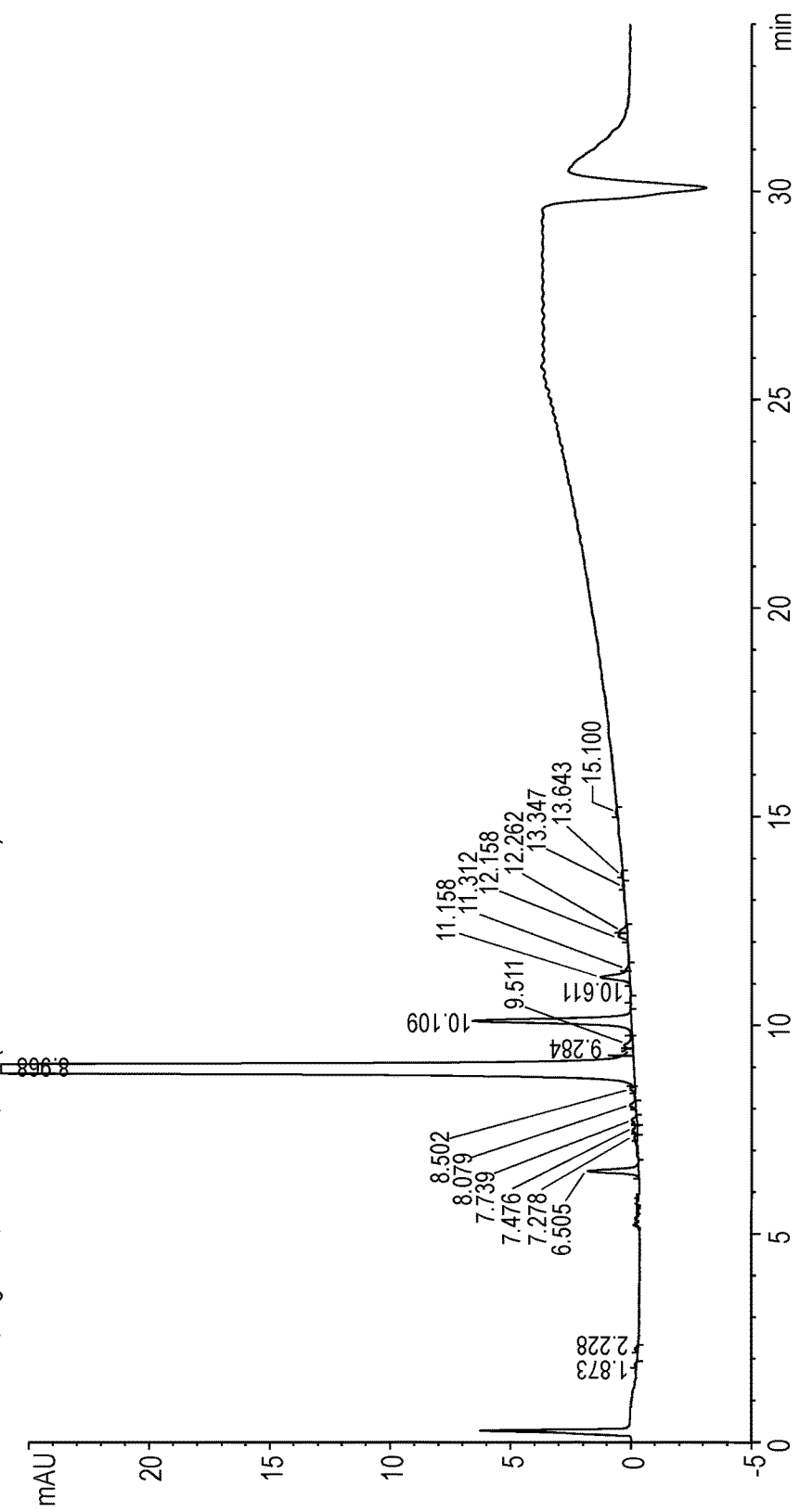
FIG. 6A and FIG. 6B shows chromatographs of LJC-039-037-1 at $T^o$ and $T^4$ (and relate to the results in Table 10)
Figure 6B:
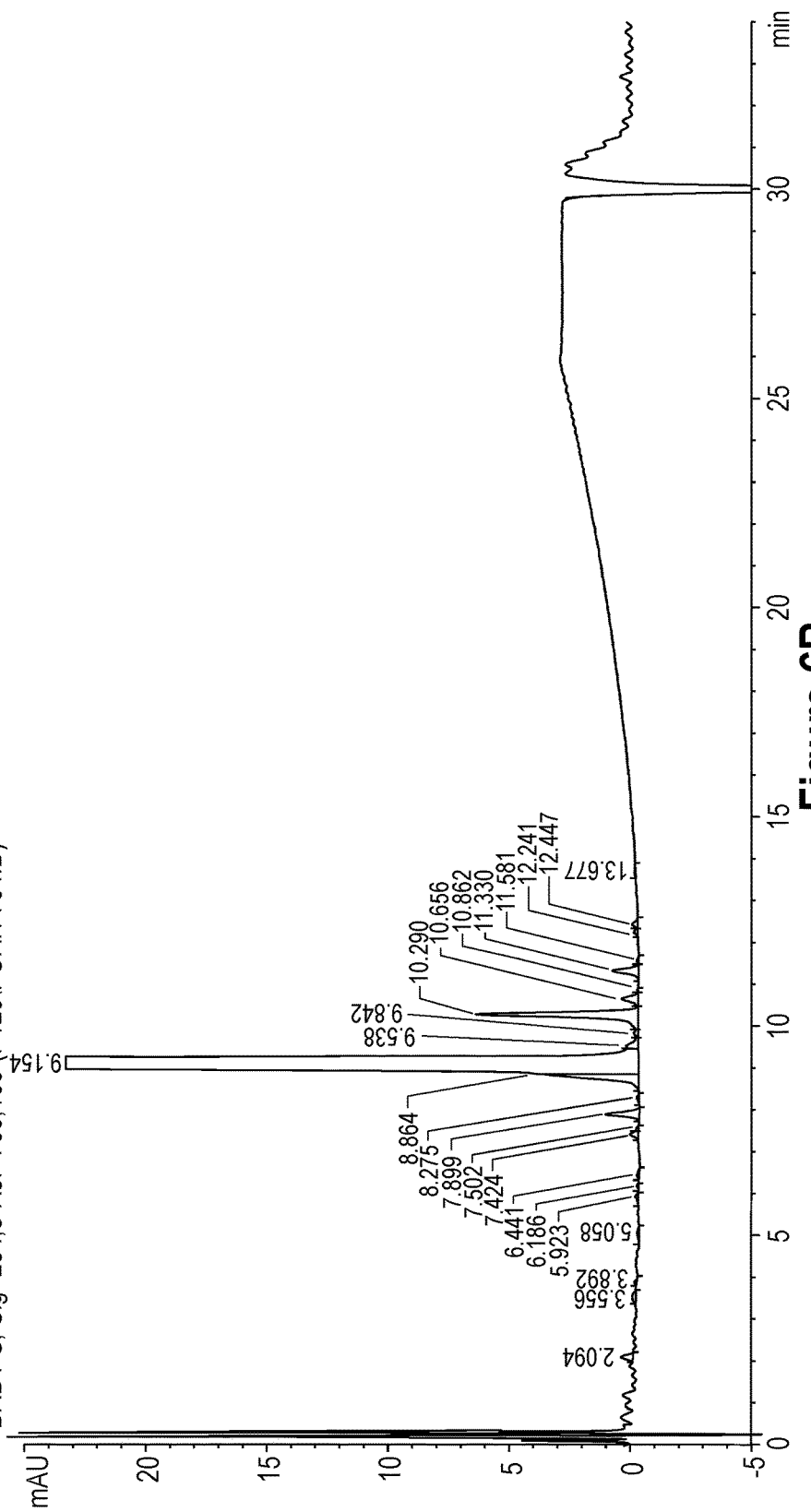

The hplc chromatographs for the besylate salt form are shown in FIG. 6 for time points week zero and week four.

It is suspected that the dominant peak prior to that of the parent is from contamination as the $\lambda_{max}$ does not match the $\lambda_{max}$ of the parent peak. It is also absent from the impurity profile of T$^1$, T$^2$, T$^3$ and T$^4$.

It can be seen from the powder patterns of the salts pre and post humidity studies that there are no changes in form.

Figure 7:
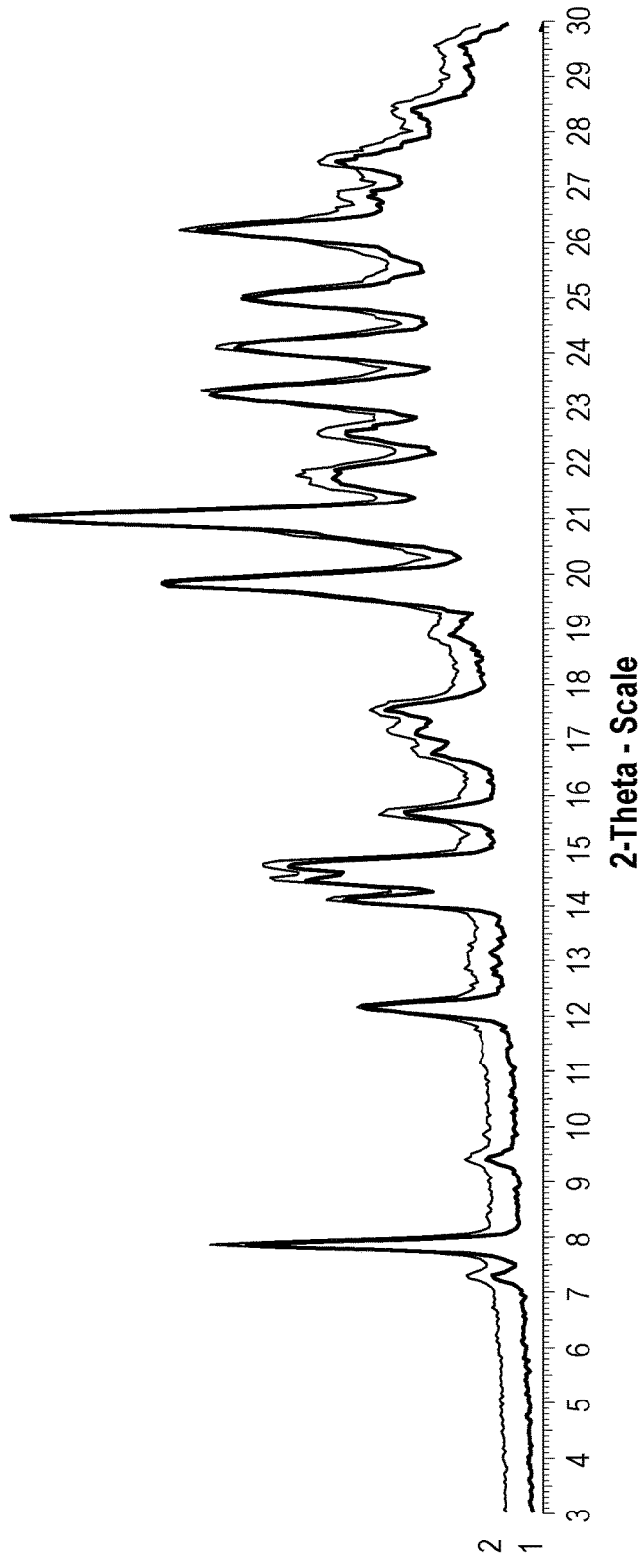
FIG. 7 shows XRPD comparing LJC-039-037-1 (besylate salt) pre and post 4 week stability study.

FIG. 7 shows XRPD comparing LJC-039-037-1 (besylate salt) pre and post 4 week stability study.

Example 5

Polymorphism Investigation

In order to determine the propensity of besylate salts to exhibit polymorphism, a maturation experiment was set up using thirty solvents (fifteen neat plus their 2.5% aqueous counterparts). The solid was slurried in various solvents (see Table 11) for one week on a heat/cool cycle from ambient to 60° C. After one week the slurries were evaporated and the solids analysed by XRPD and HPLC.

TABLE 11

Results of polymorphism investigation for besylate (LJC-039-058-2) starting hplc purity 97.7%

| Entry | solvent | XRPD post 1 week | HPLC purity/% area |
|---|---|---|---|
| 1 | acetone | Form 1 | 97.5 |
| 2 | THF | Form 1 | 97.6 |
| 3 | IPA | amorphous | 97.1 |
| 4 | MtBE | Form 1 | 97.7 |
| 5 | DCM | amorphous | 97.4 |
| 6 | EtOH | oil | not analysed |
| 7 | MEK | Form 1 | 97.2 |
| 8 | 1,4-Dioxane | Form 1 | 97.2 |
| 9 | iPrOAc | Form 1 | 97.5 |
| 10 | DMF | oil | not analysed |
| 11 | MeCN | Form 1 | 94.3 |
| 12 | nBuOH | oil | not analysed |
| 13 | nPrOH | oil | not analysed |
| 14 | MIBK | Form 1 | 97.7 |
| 15 | MeOH | oil | not analysed |
| 16 | 2.5% aq acetone | Form 1 | 96.8 |
| 17 | 2.5% aq THF | amorphous | 93.3 |
| 18 | 2.5% aq IPA | Form 1 | 76.1 |
| 19 | 2.5% aq MtBE | oil | not analysed |
| 20 | 2.5% aq DCM | Form 1 | 97.4 |
| 21 | 2.5% aq EtOH | oil | not analysed |
| 22 | 2.5% aq MEK | Form 1 | 93.9 |
| 23 | 2.5% aq 1,4-Dioxane | Form 1 | 86 |
| 24 | 2.5% aq iPrOAc | oil | not analysed |
| 25 | 2.5% aq DMF | oil | not analysed |
| 26 | 2.5% aq MeCN | Form 1 | 93.3 |
| 27 | 2.5% aq nBuOH | oil | not analysed |
| 28 | 2.5% aq nPrOH | oil | not analysed |
| 29 | 2.5% aq MIBK | Form 1 | 97.3 |
| 30 | 2.5% aq MeOH | oil | not analysed |

The maturation study using the besylate salt revealed no new forms. The purity results post maturation show that those slurried in acetonitrile, aqueous THF, aqueous IPA aqueous MEK, aqueous dioxane and aqueous acetonitrile degraded. This suggests that the besylate salt (Form 1) has good solution stability in neat organic solvents at high temperature.

Investigating New Forms of Besylate

Although no new forms of the besylate salt were seen from the maturation study, a new form was seen when crystals were grown in methanol. The single crystals obtained from methanol were ground in order to obtain a powder pattern. This pattern turned out to be different from Form 1. A repeat experiment was carried out in order to obtain a further supply of Form 2. It was only possible to isolate Form 2 from precipitation over 16 hours from the liquors, opposed to allowing the solvent to evaporate, this gave Form 1. Interestingly two habits were present; needles and blocks. Both showed the same powder pattern as the needle habit that was used for single crystal structure determination.

Full analysis was carried out on Form 2. It had been concluded that it was a true polymorph as the single crystal data confirmed anhydrous besylate 1:1.

Figure 8A:
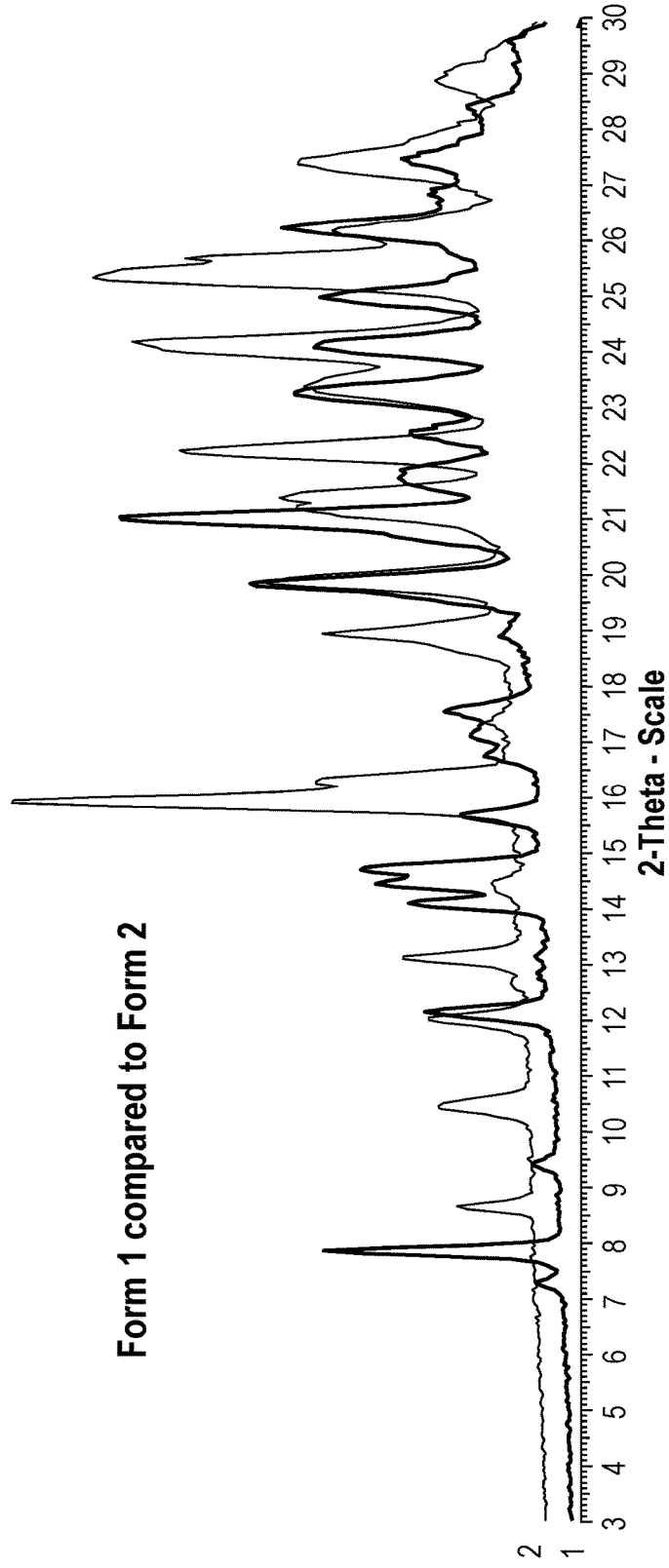
FIG. 8A shows an XRPD comparison of besylate Form 1 and 2.

FIG. 8A shows an XRPD comparison of besylate Form 1 and 2. There is an obvious difference between Form 1 (trace 1) and Form 2 (trace 2). As can be seen from the two powder patterns, both forms are very different. Thermal analysis was carried out to compare the melting points of the two forms and also thermodynamic solubility measurements recorded.

Figure 8B:
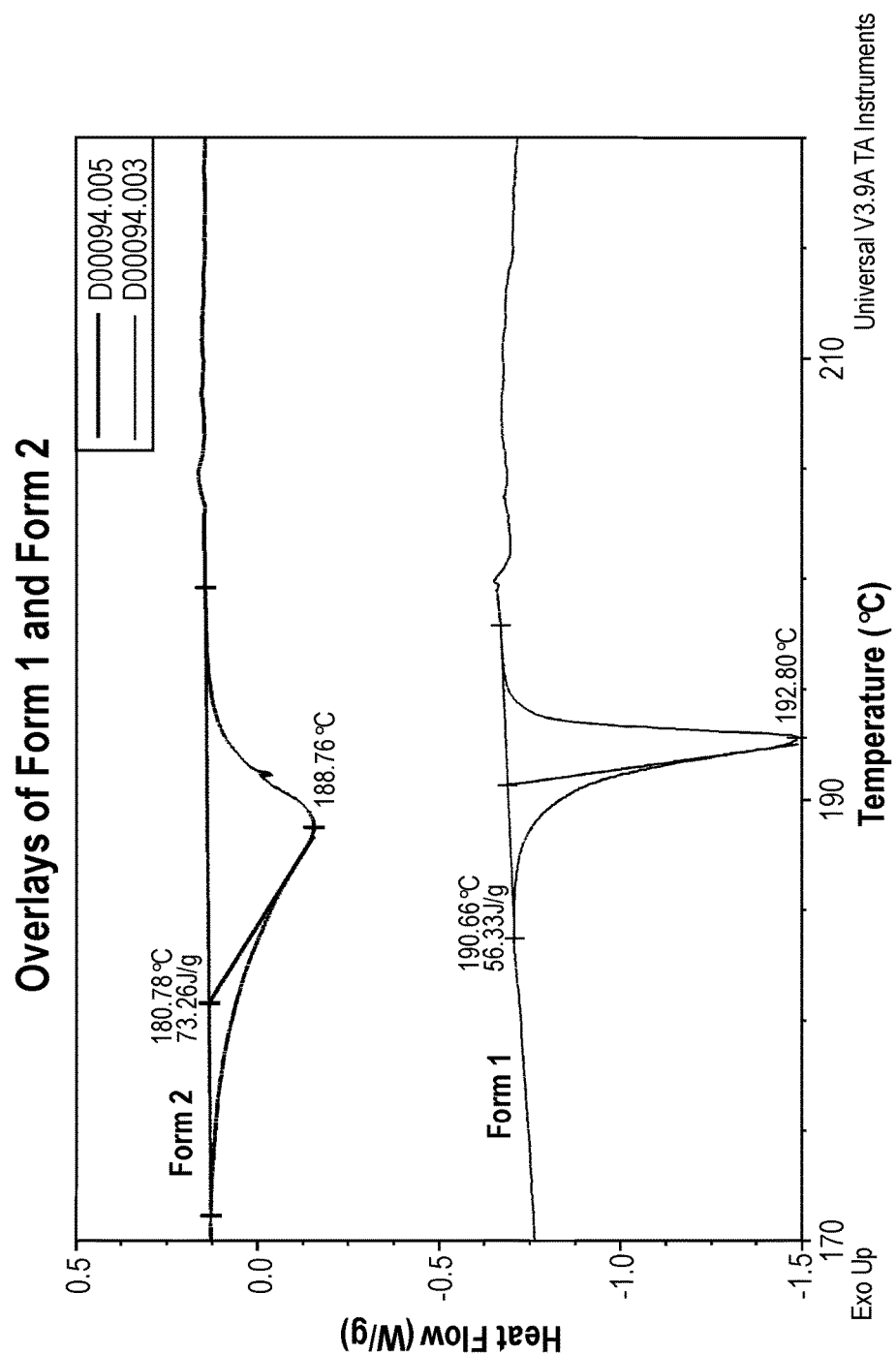
FIG. 8B shows Differential Scanning calorimetry (DSC) overlays of Form 1 and 2.

FIG. 8B shows overlays of Form 1 and 2. Form 1 and 2 show one endothermic event (melting).

Form 3 was identified when a second crop was isolated from the liquors of LJC-039-081-1 (the 1 g scale-up reaction). Analysis was carried out in order to determine whether or not it was a solvate and how the forms interconvert.

Figure 9A:
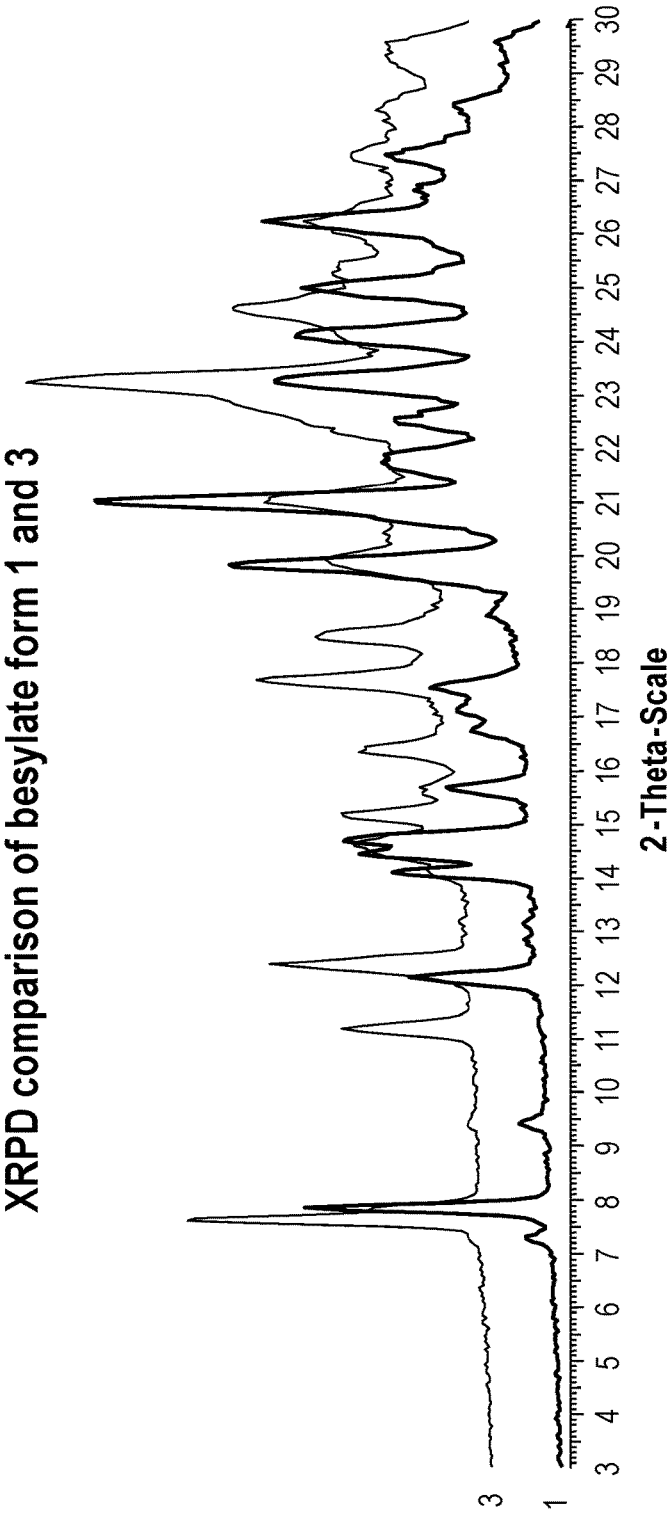
FIG. 9A shows an XRPD comparison of besylate Form 1 and 3.
Figure 9B:
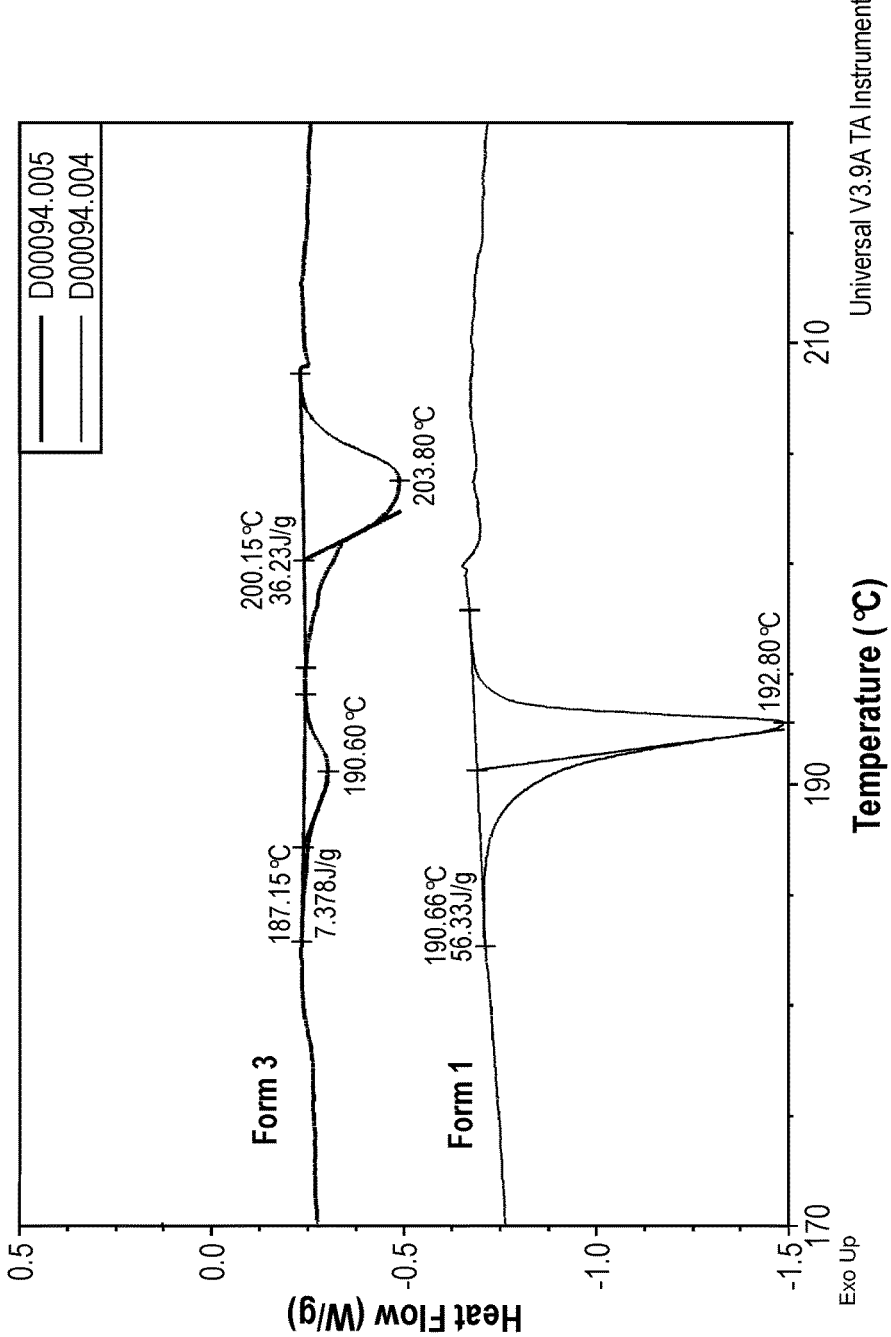
FIG. 9B shows overlays of Form 1 and 3.

FIG. 9A shows an XRPD comparison of besylate Form 1 and 3. FIG. 9B shows overlays of Form 1, and 3.

Form 1 shows one endothermic event (melting), whereas Form 3 shows two events. Hostage microscopy on Form 3 clearly shows two melts within 20° C. of each other. It is postulated that a small amount of the lower melting polymorph is present as it was not picked up in variable temperature XRPD, which is a less sensitive technique. It is quite possible that the first endothermic event represents Form 1 as it was used to seed the liquors that Form 3 was isolated from.

The solubility data shows that all three forms have very similar aqueous solubilities of 7.8 to 8.3 mg/ml at pH 3.

Besylate Salt Form 4

The release batch of besylate salt Form 1 (LJC-039-083-1) was of high purity (97.6%), but contained a small amount of impurity carried through from the free base (0.78%, 11.9 min RT). This impurity was observed in the DSC experiment showing an endothermic transition (onset at 130° C.). The peak was confirmed as having an unrelated λmax to that of the parent peak.

Figure 10:
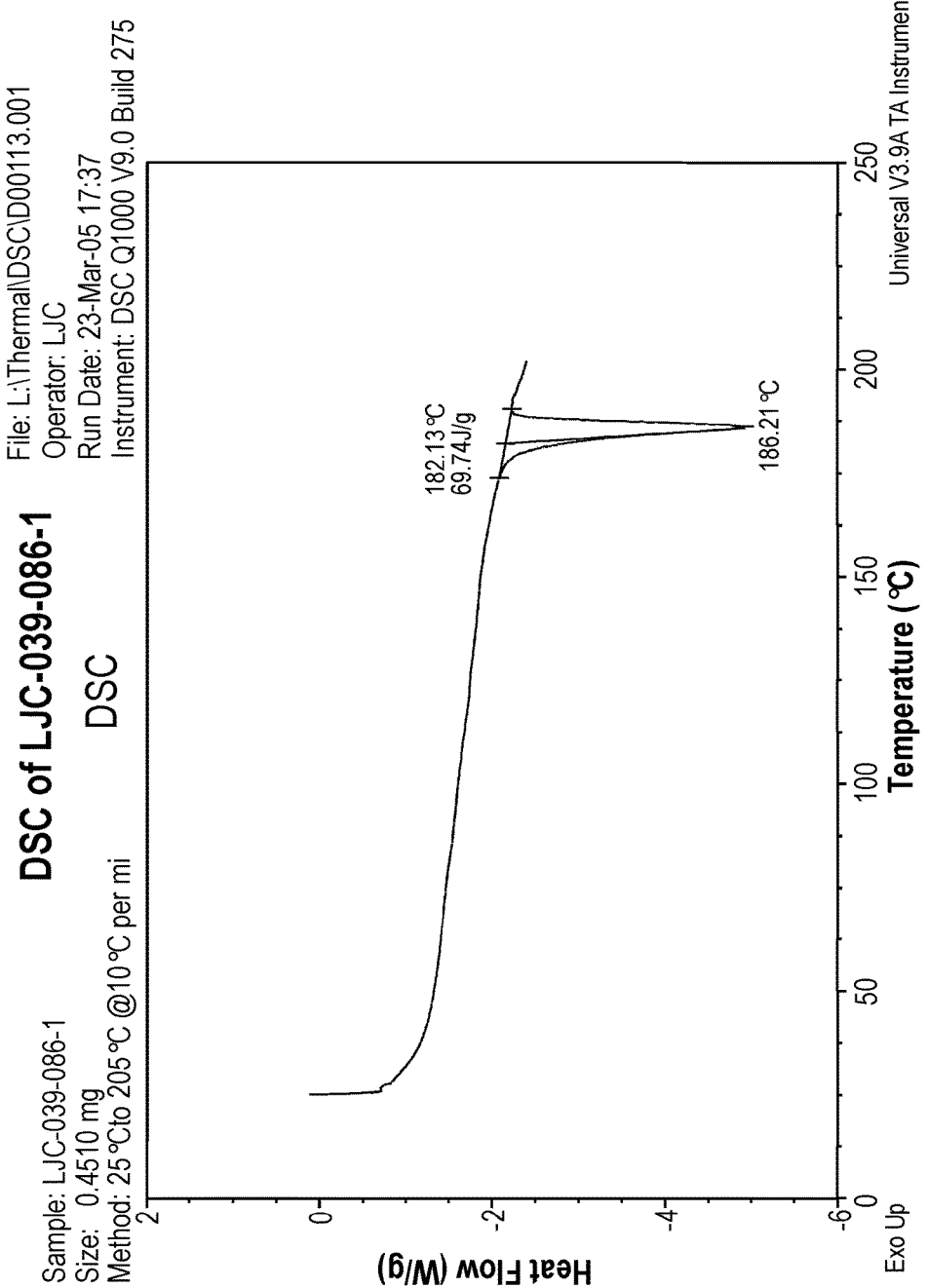
FIG. 10 shows DSC of LJC-039-086-1 (besylate Form 4)
Figure 11A:
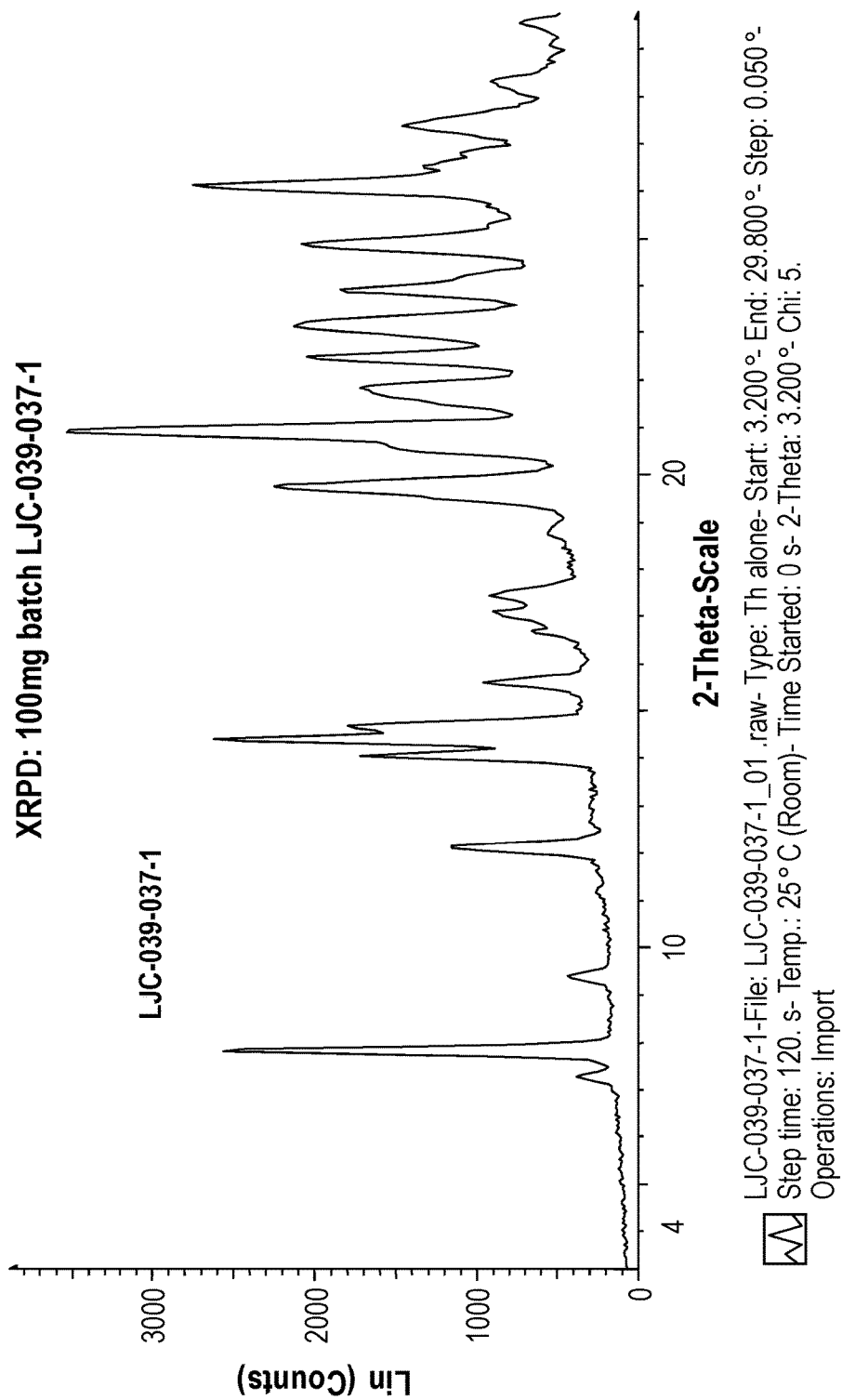
FIGS. 11A-11I show results for besylate Form 1.
Figure 11B:
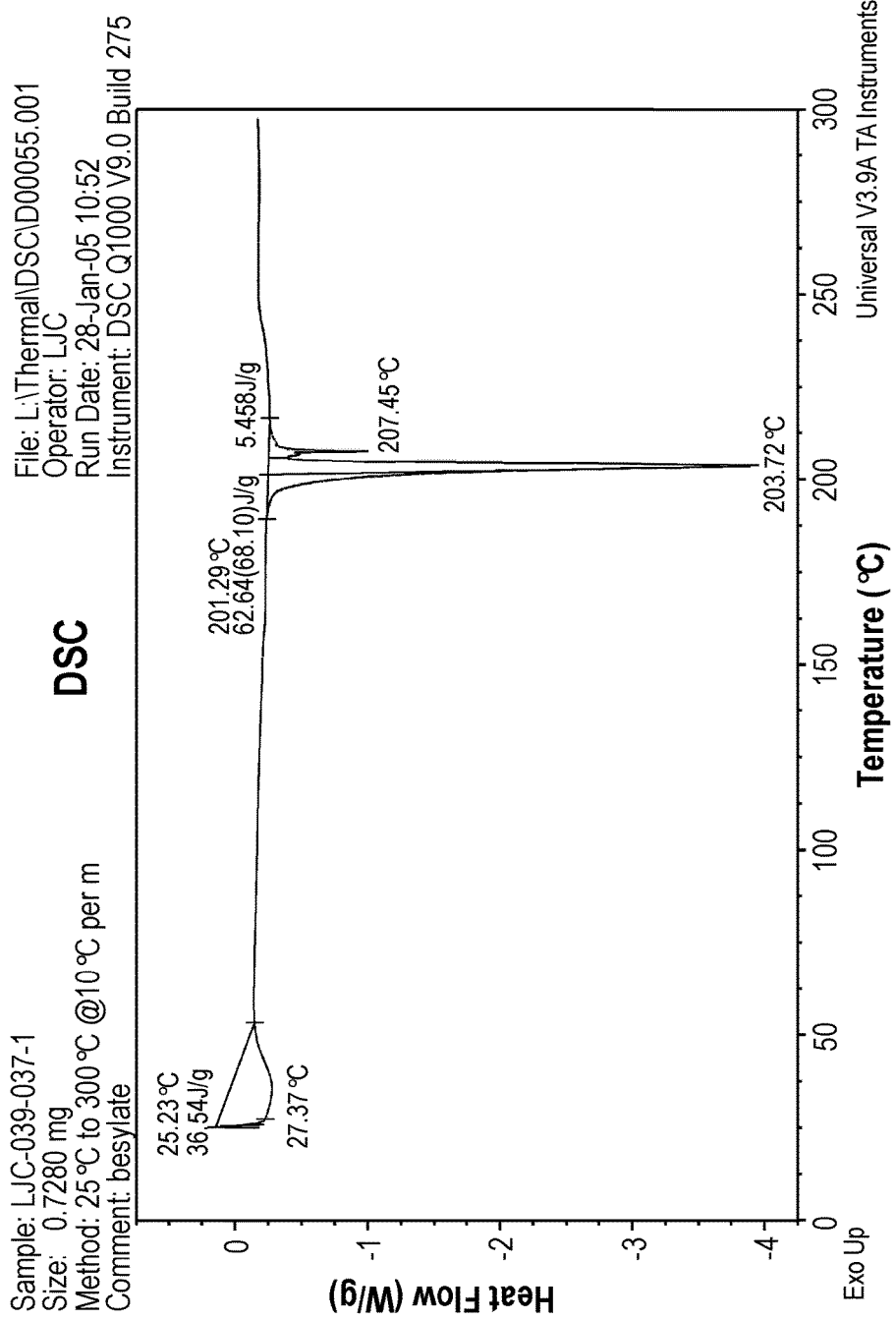
Figure 11C:
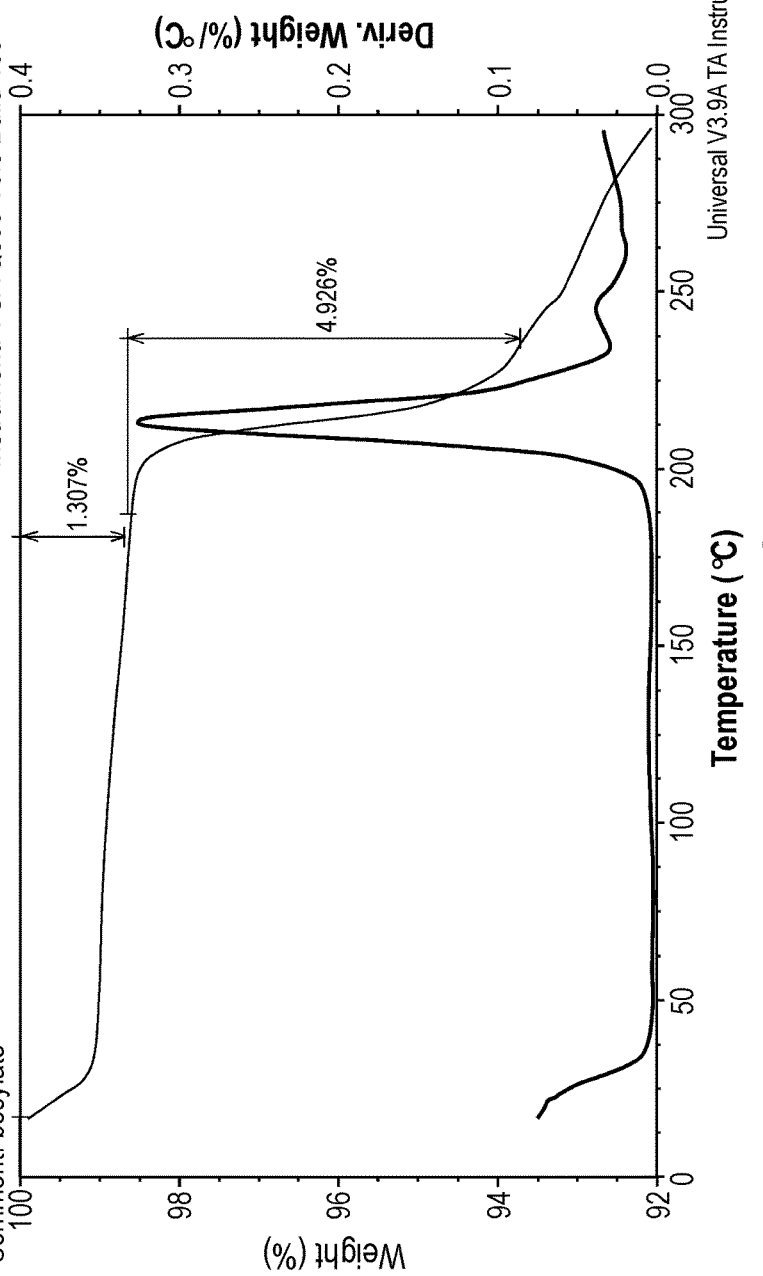
Figure 11D:
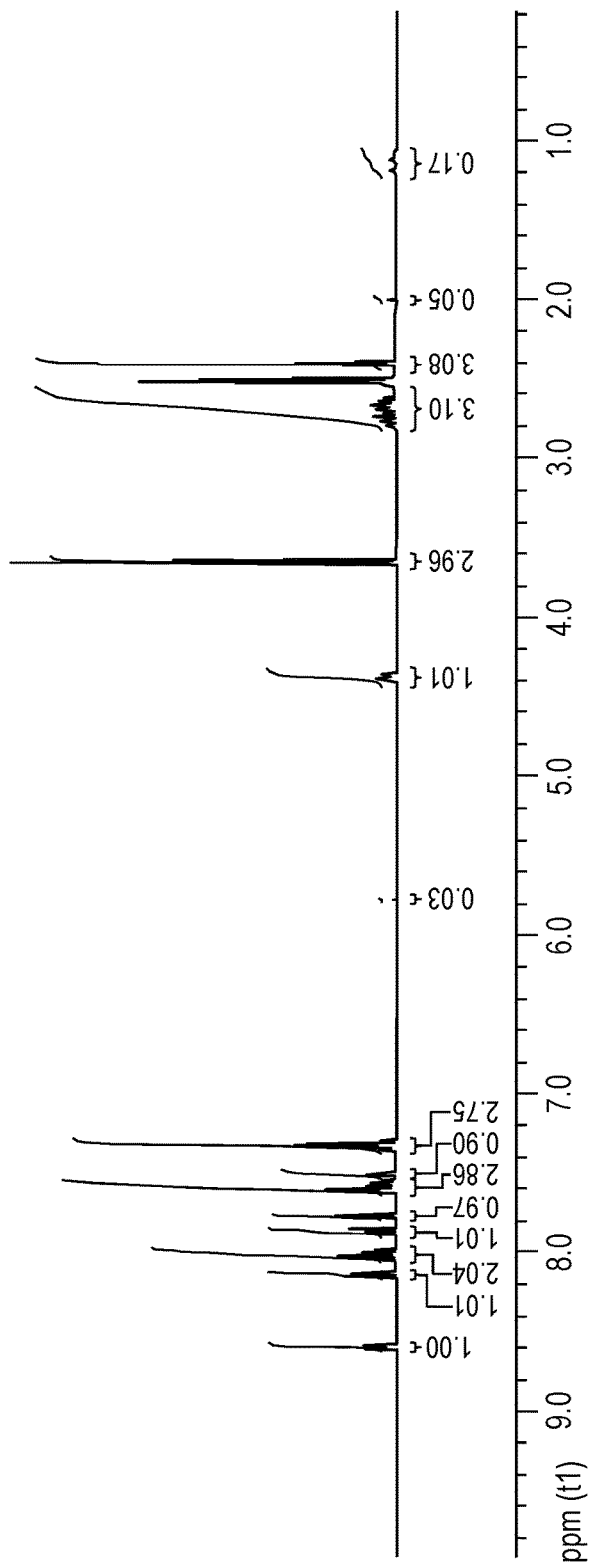
Figure 11E:
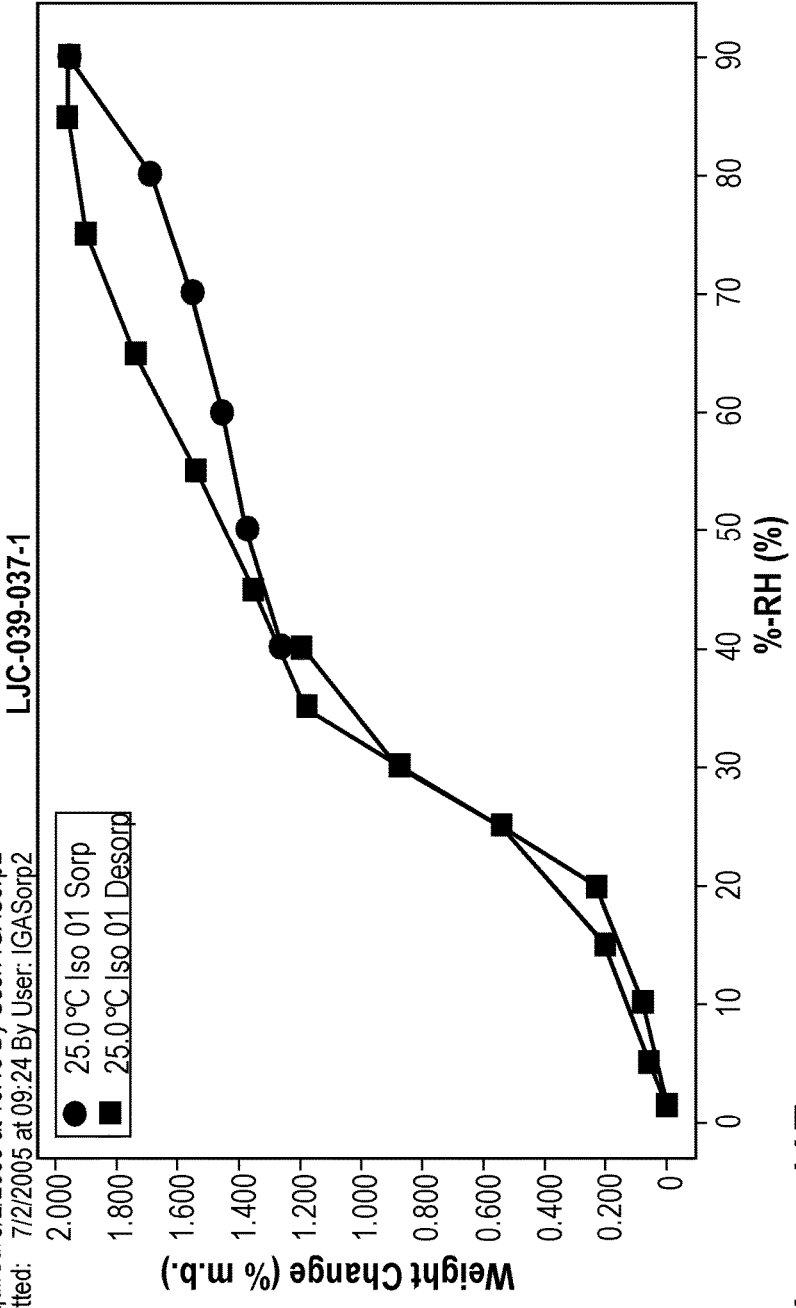
Figure 11F:
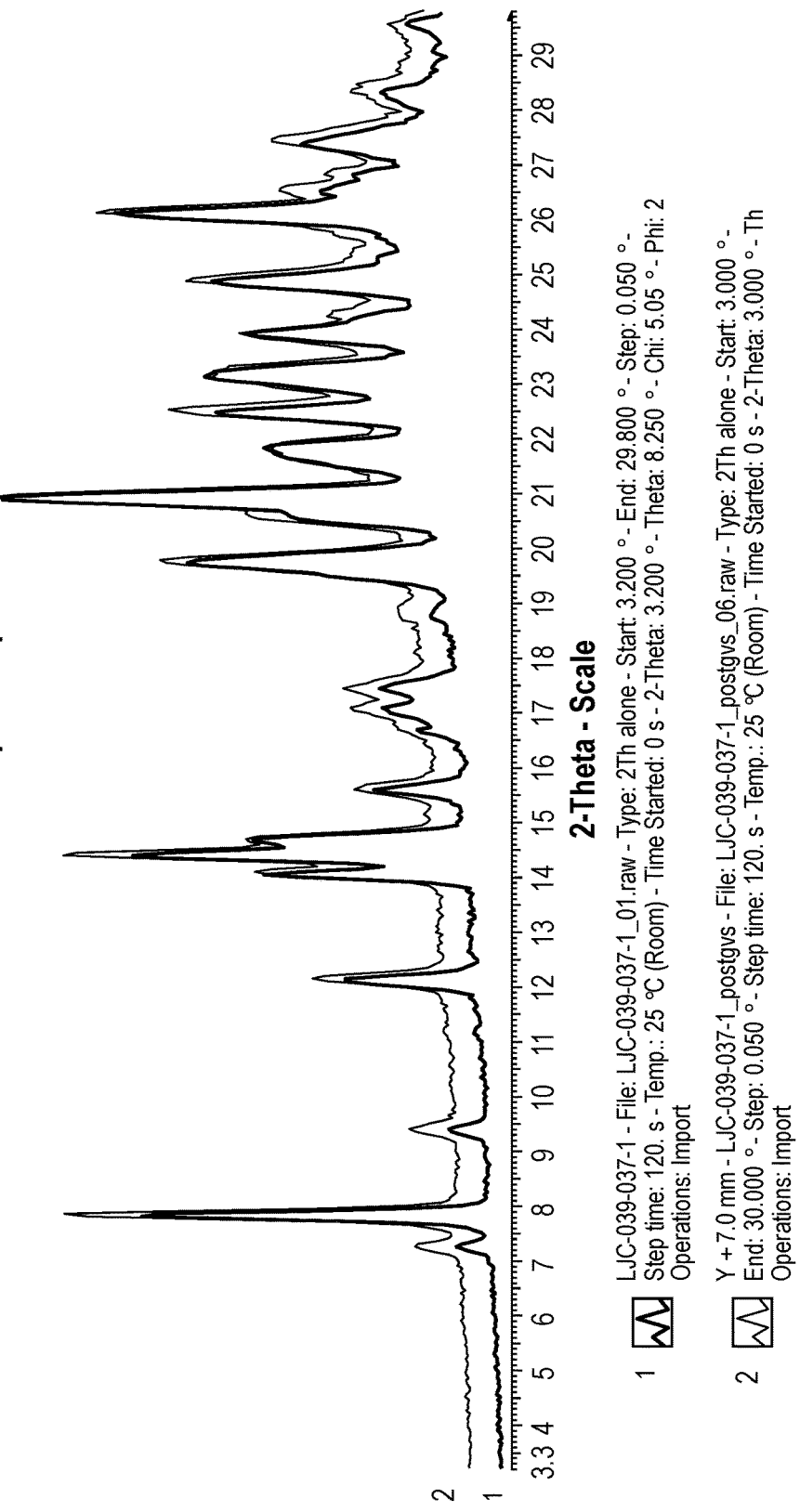
Figure 11G:
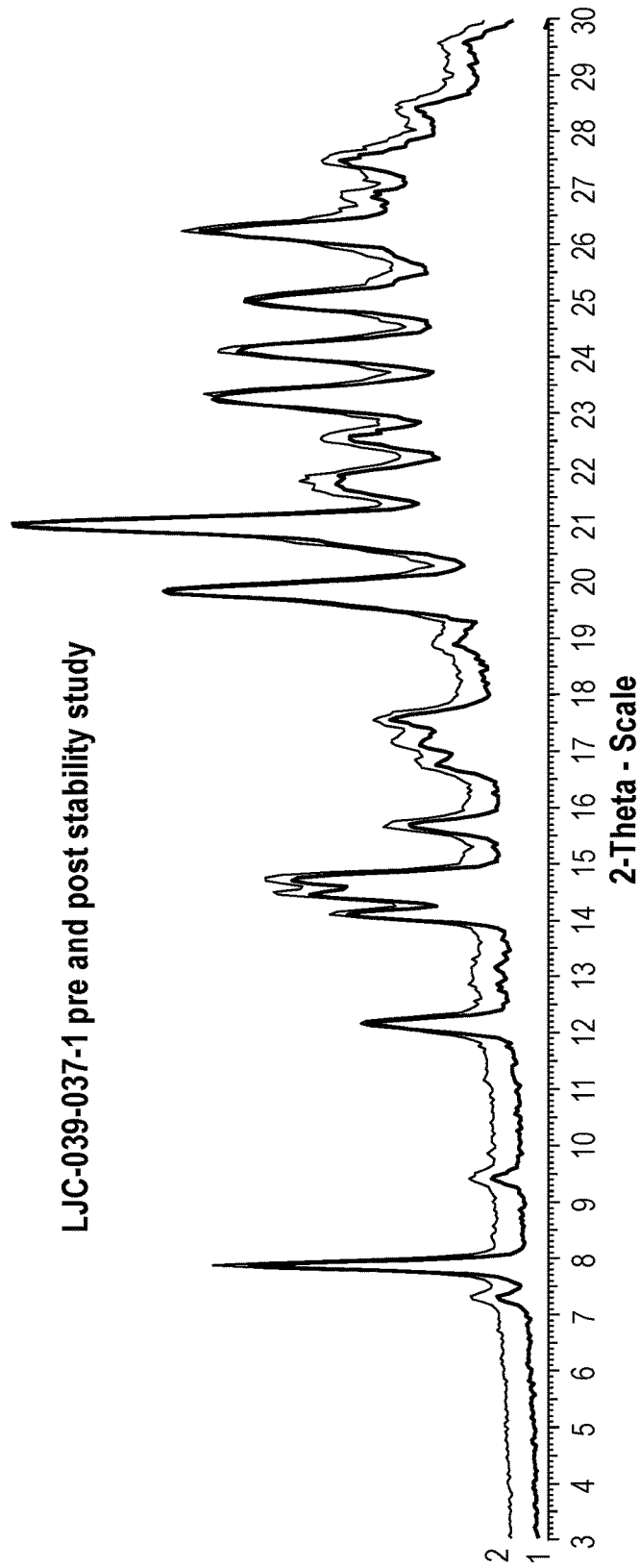
Figure 11H:
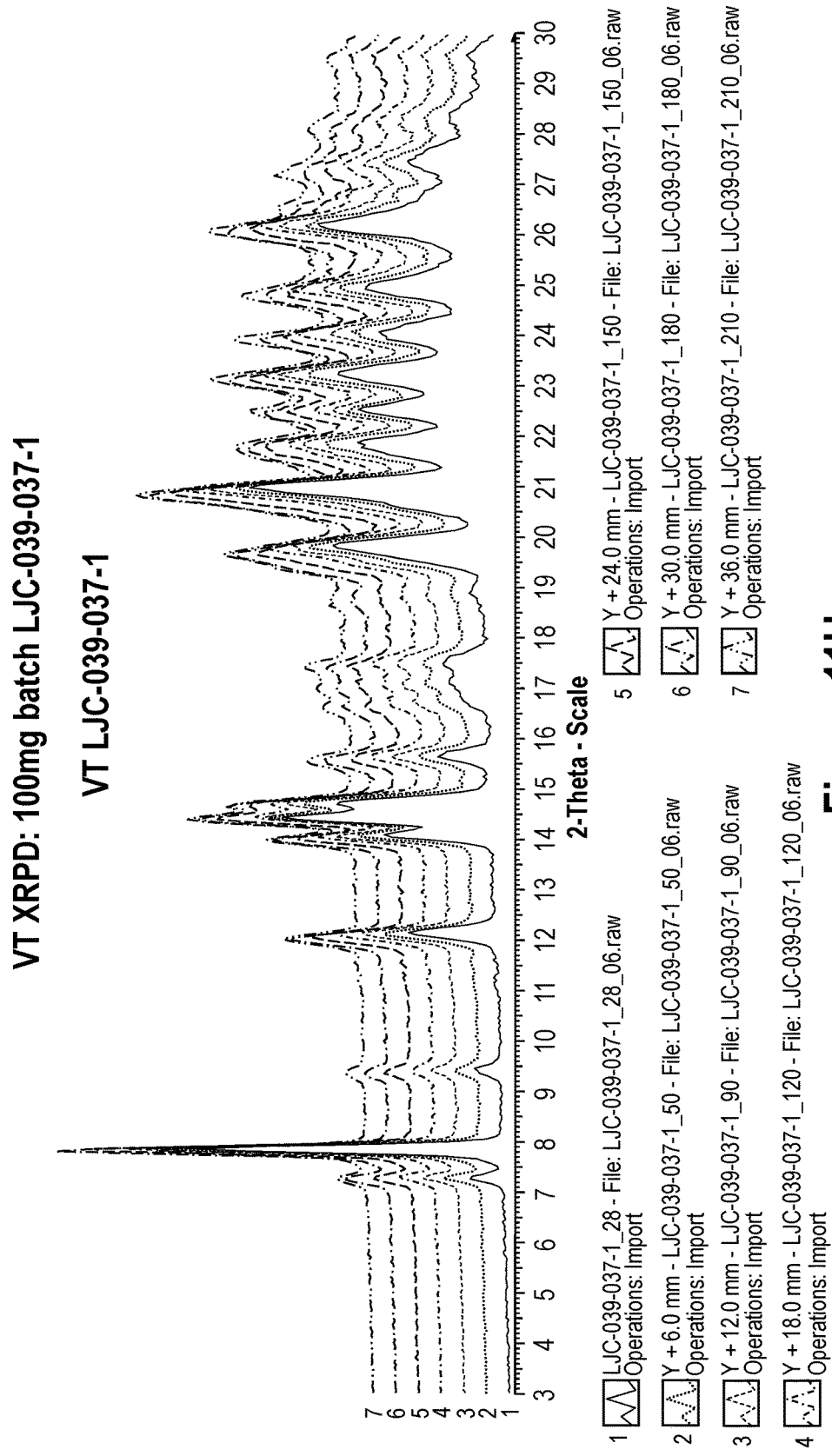
Figure 11I:
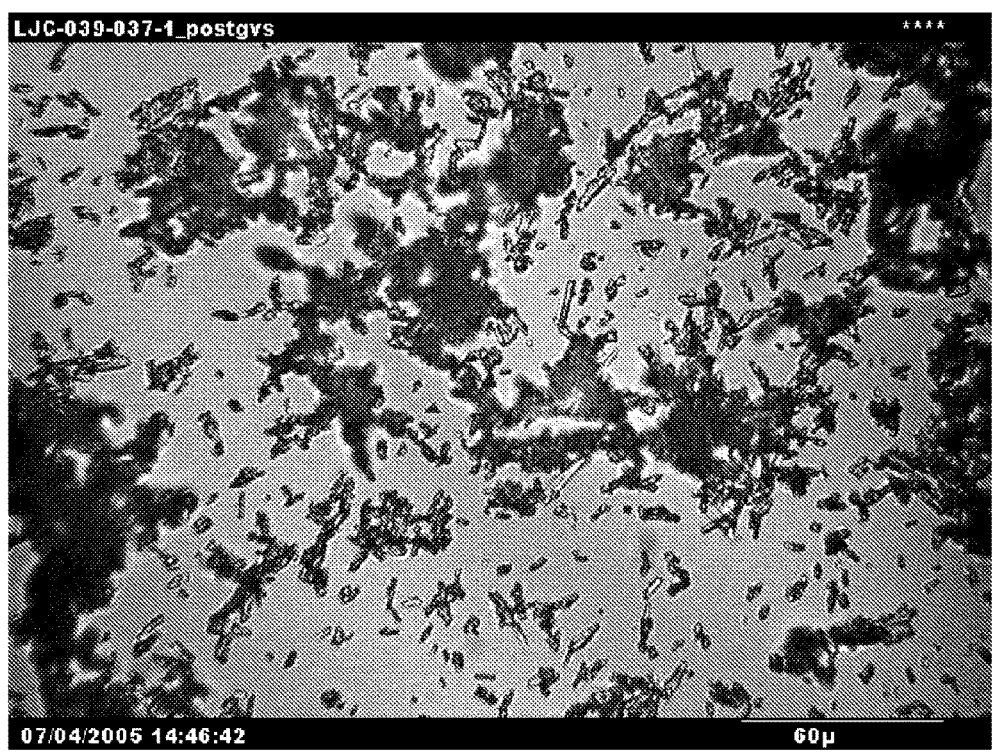
Figure 12A:
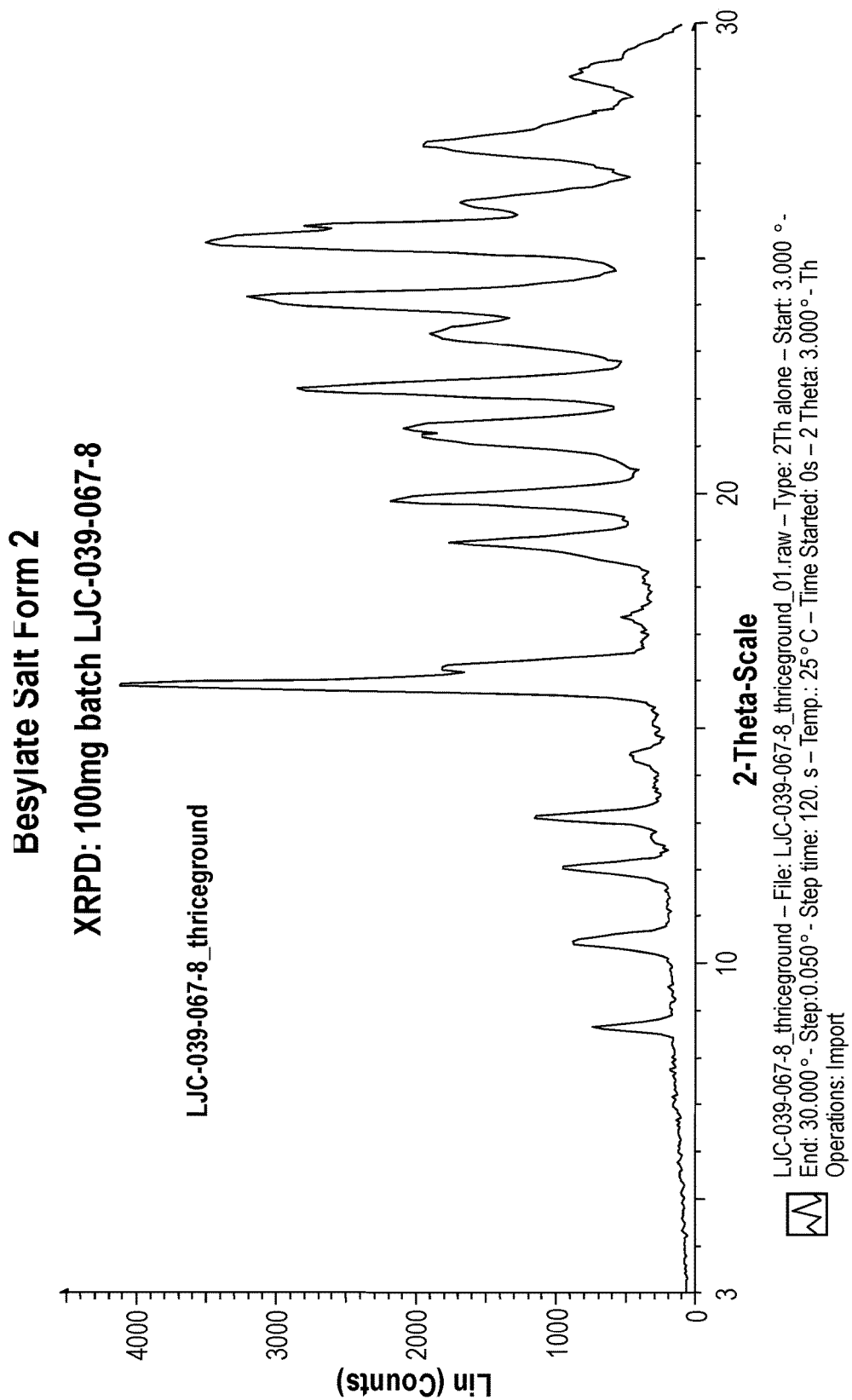
FIGS. 12A-12D show results for besylate Form 2.
Figure 12B:
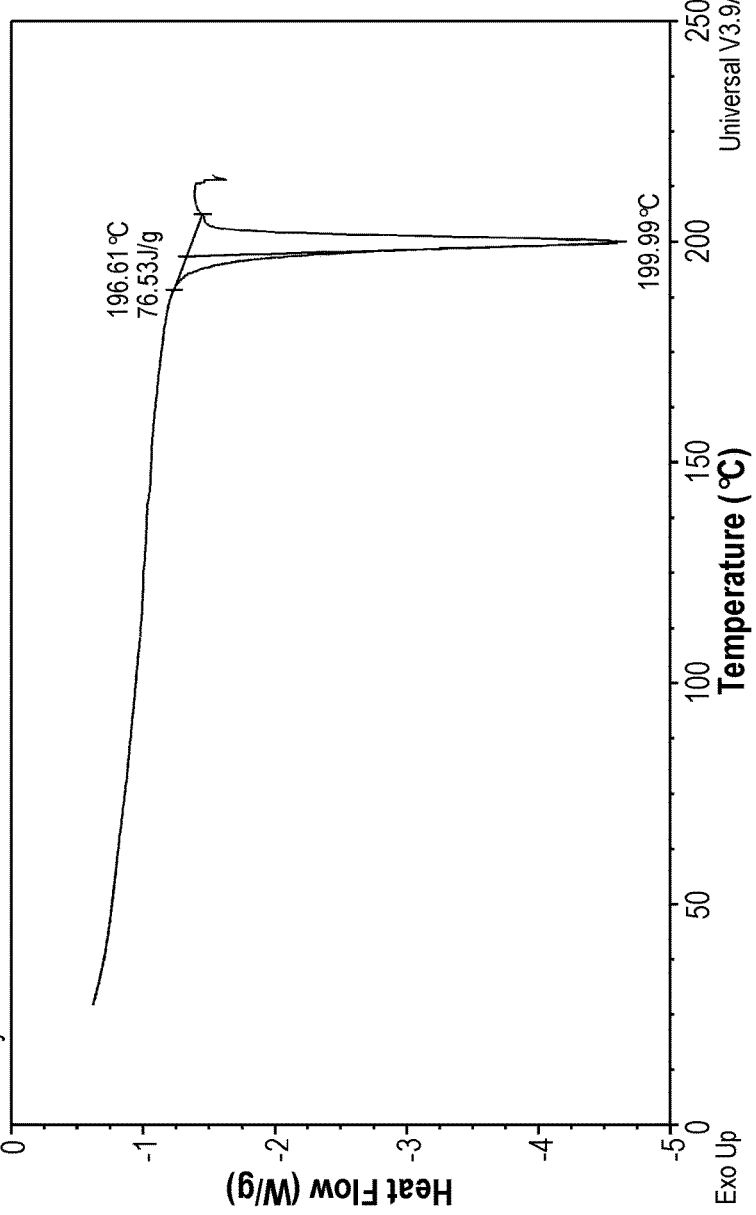
Figure 12C:
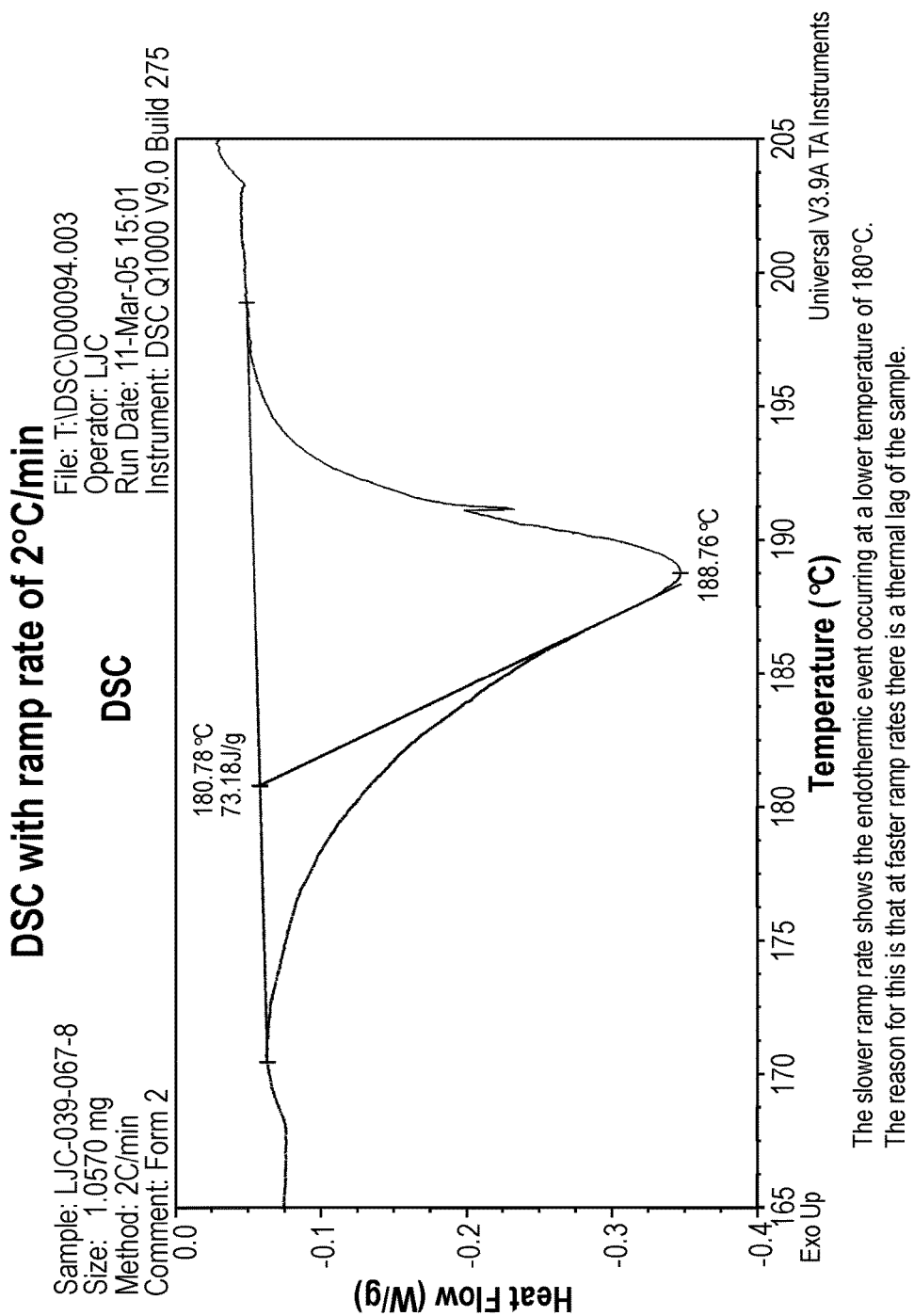
Figure 12D:
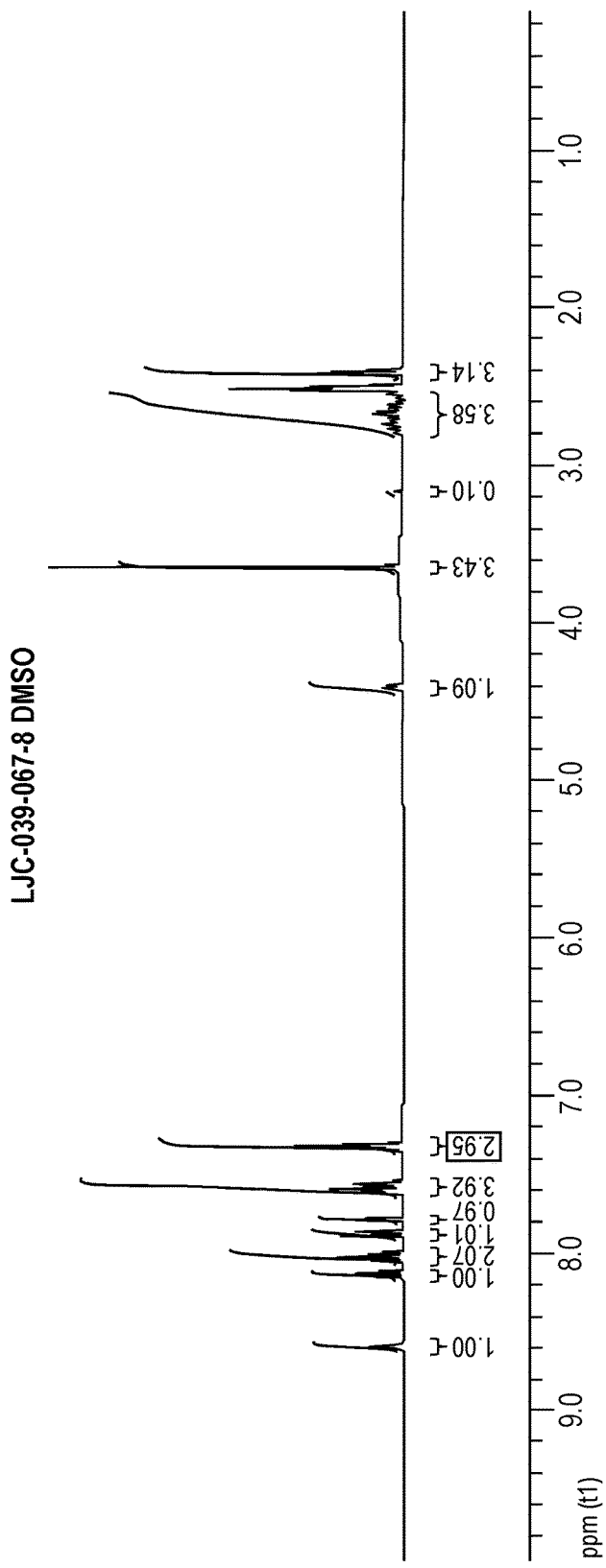
Figure 13A:
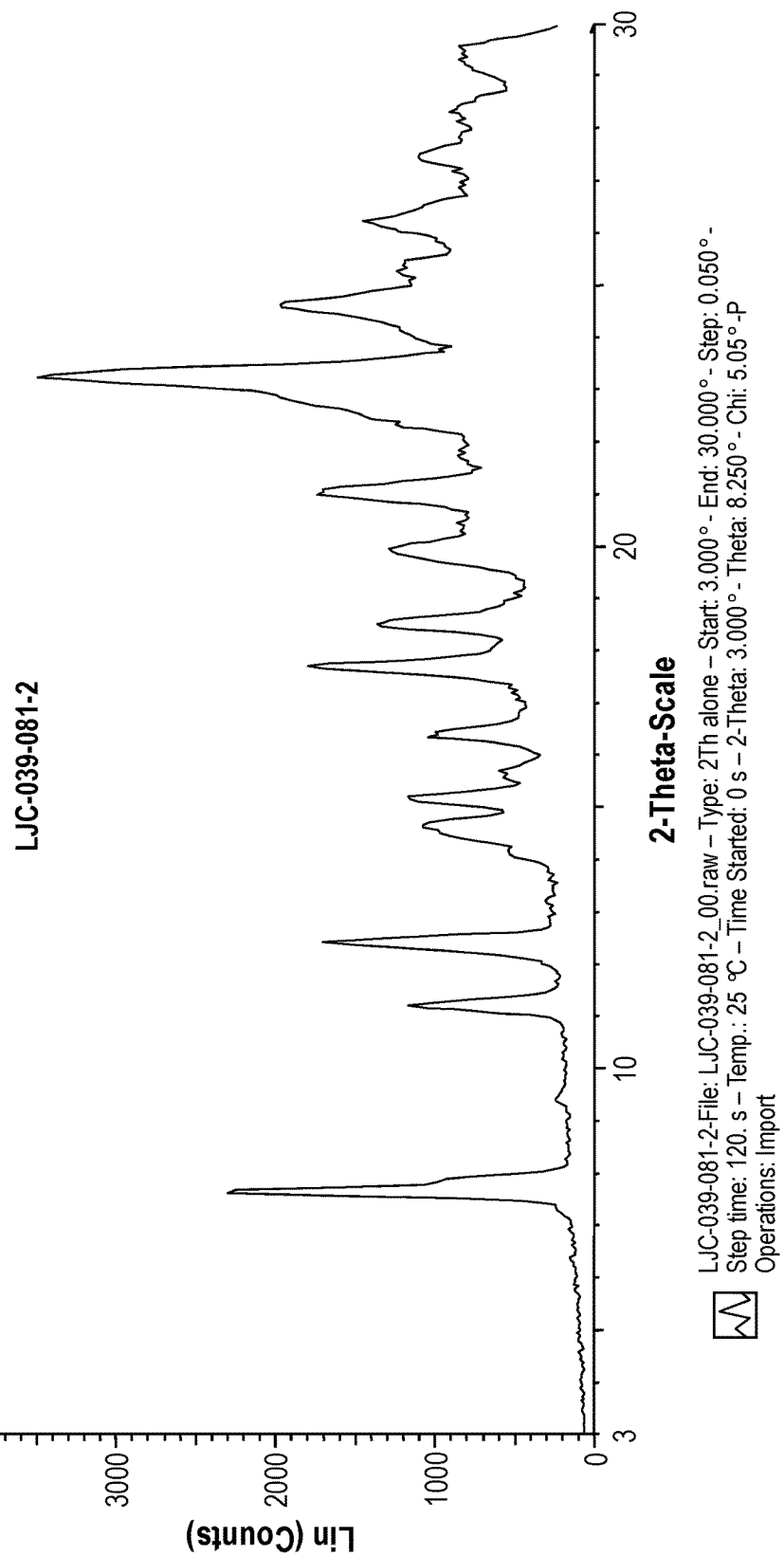
FIGS. 13A-13G show results for besylate Form 3.
Figure 13B:
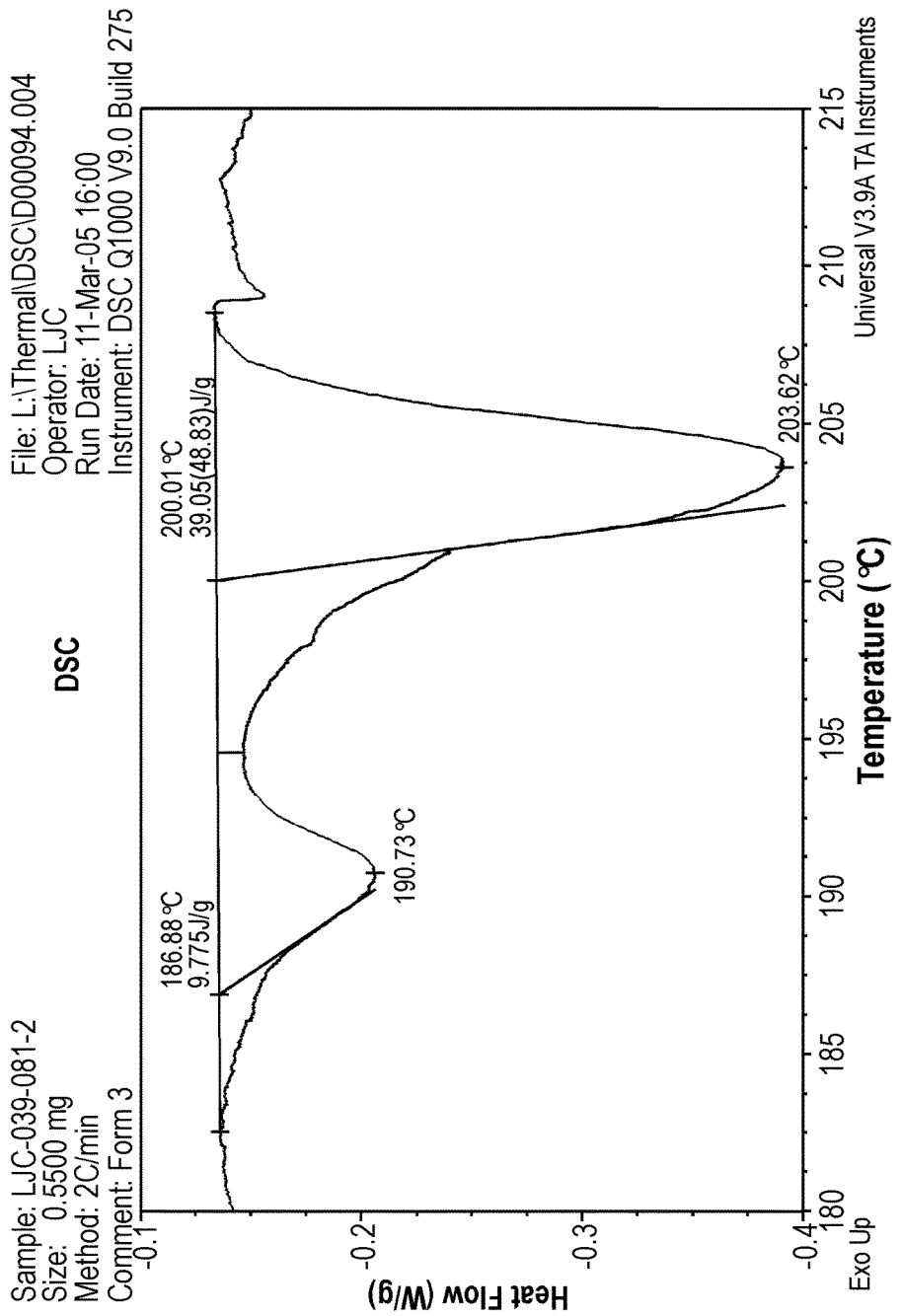
Figure 13C:
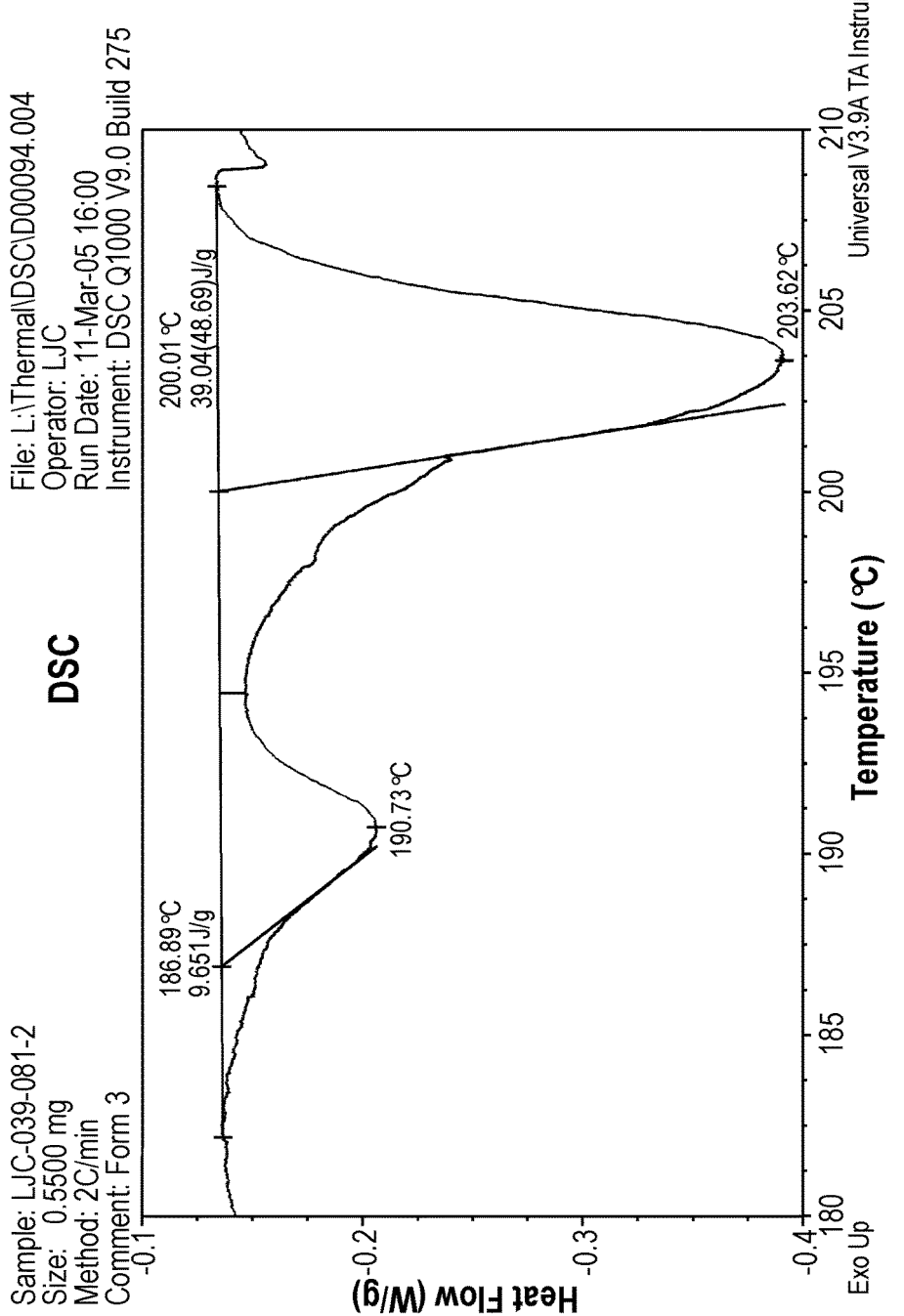
Figure 13D:
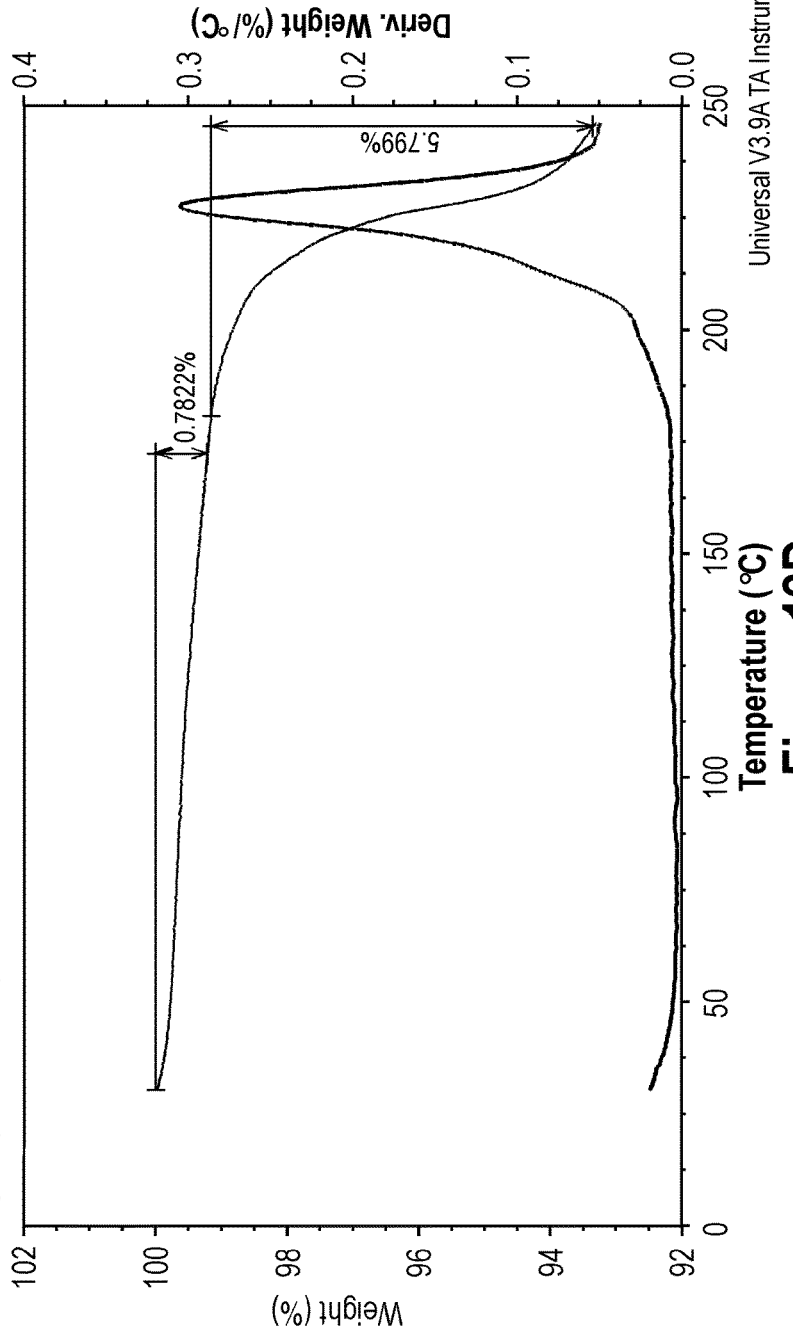
Figure 13E:
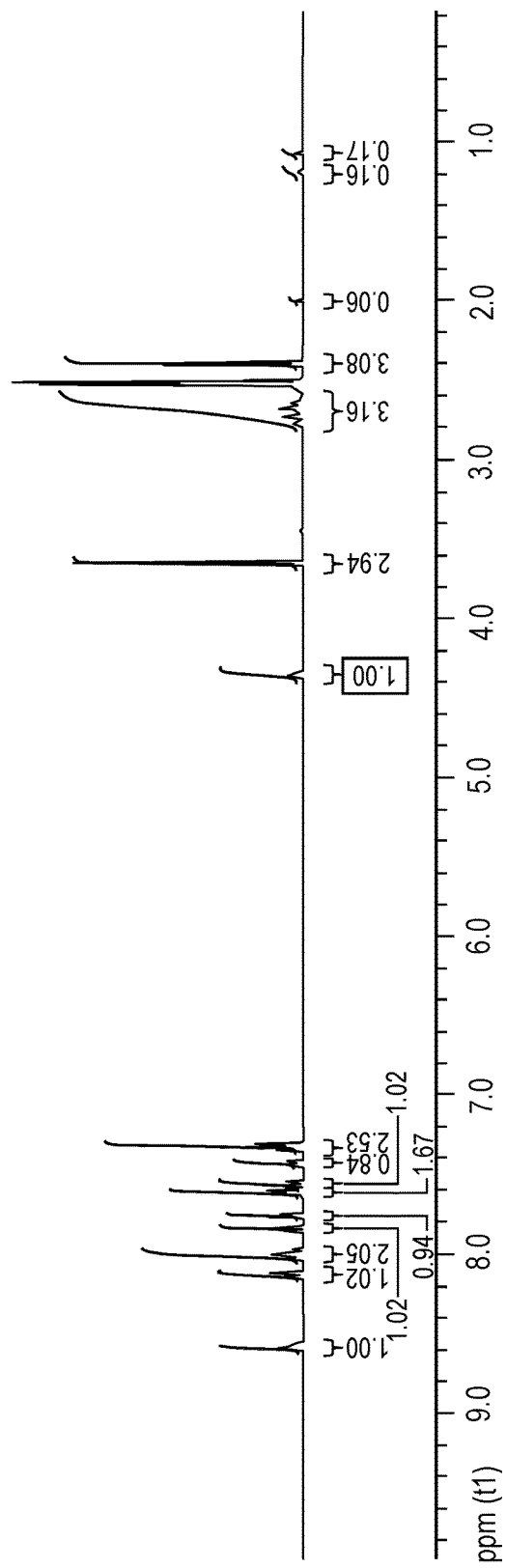
Figure 13F:
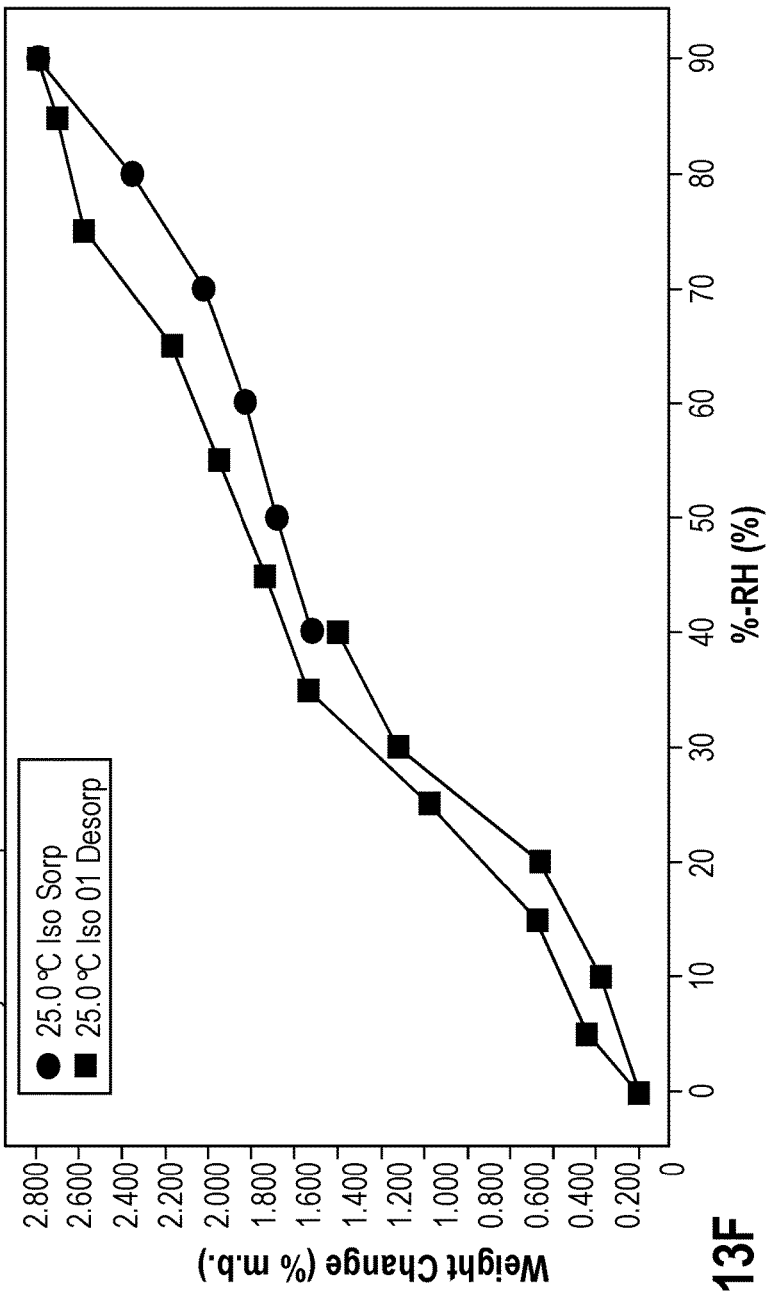
Figure 13G:
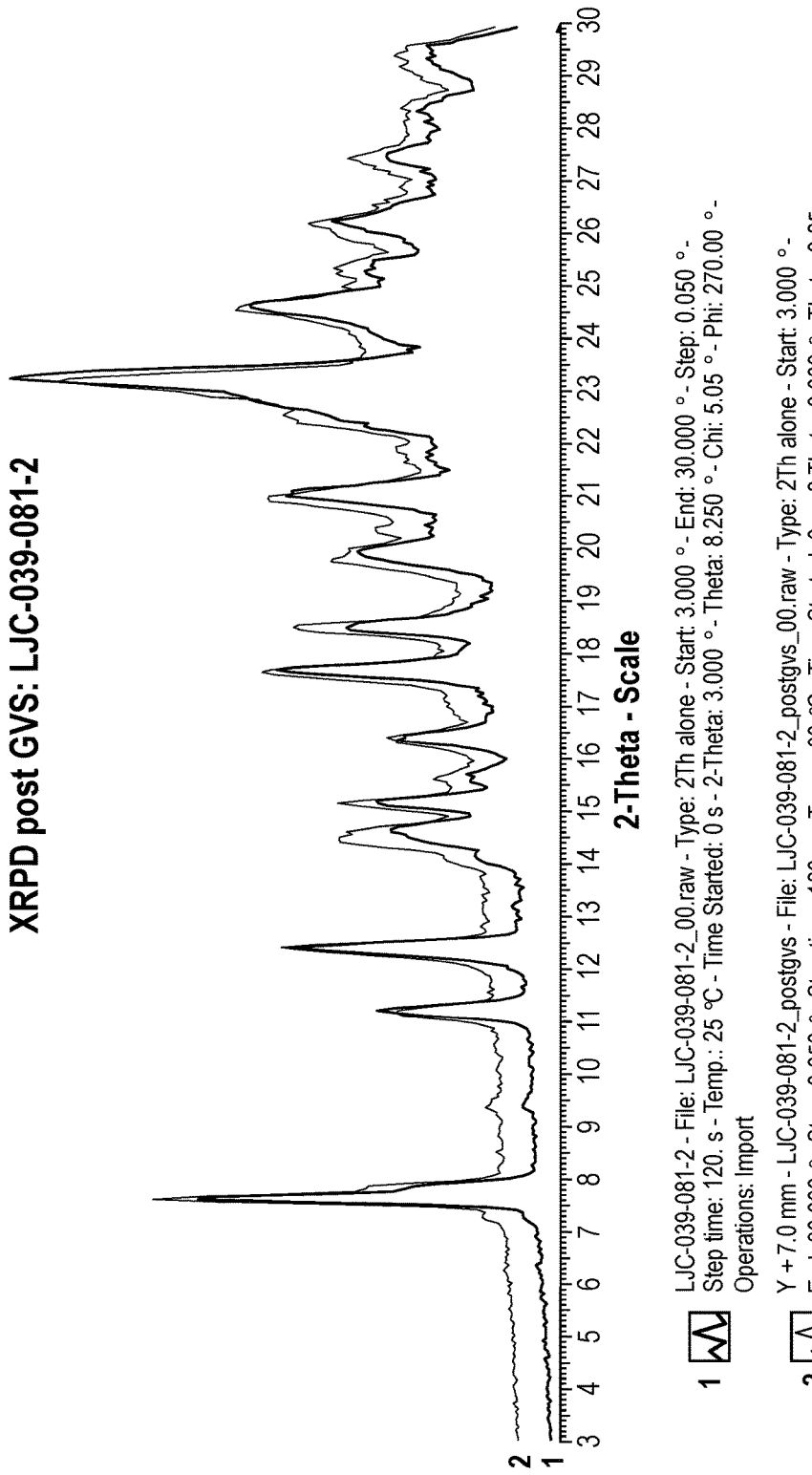
Figure 14A:
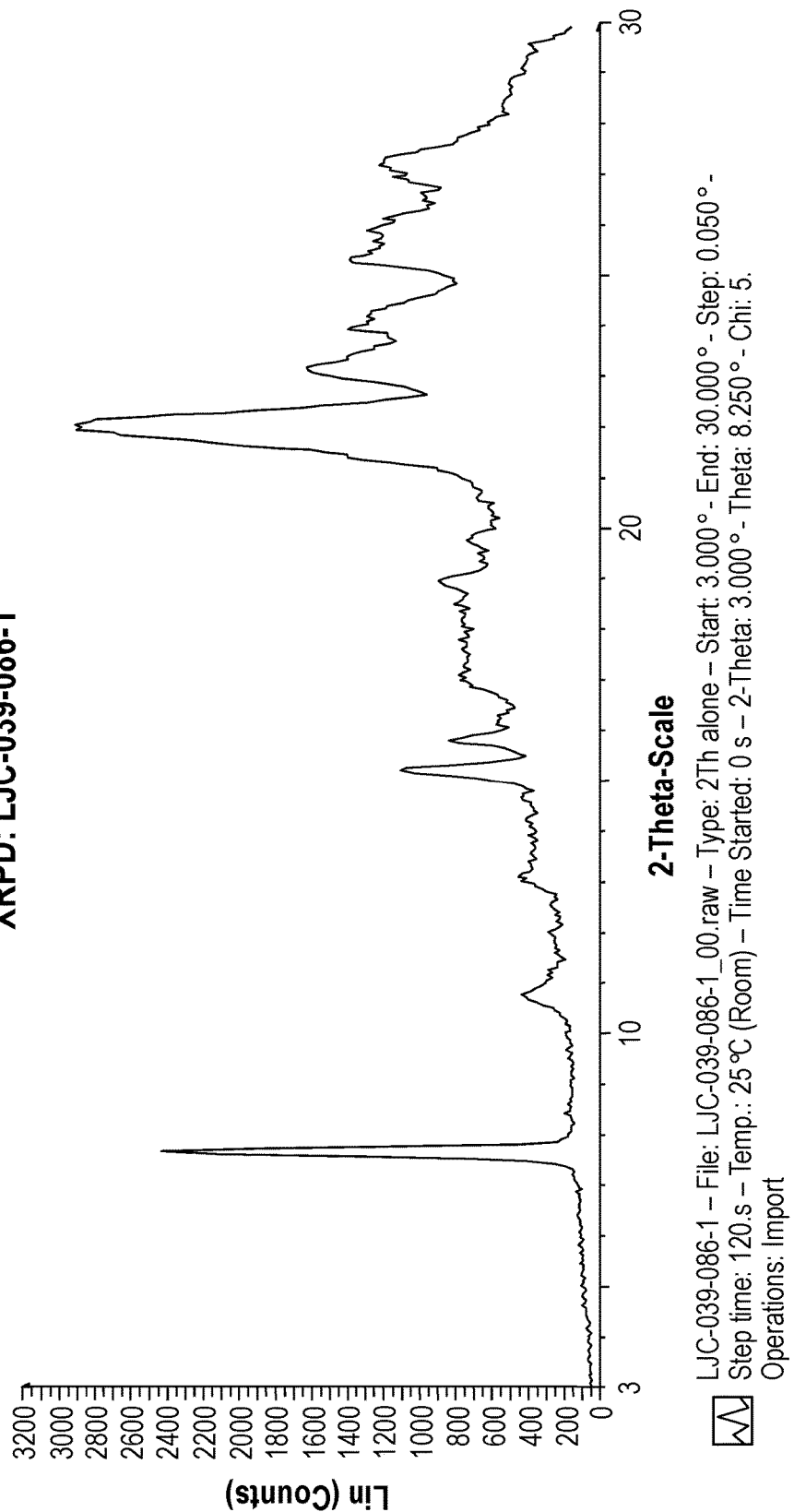
FIGS. 14A-14C show results for besylate Form 4.
Figure 14B:
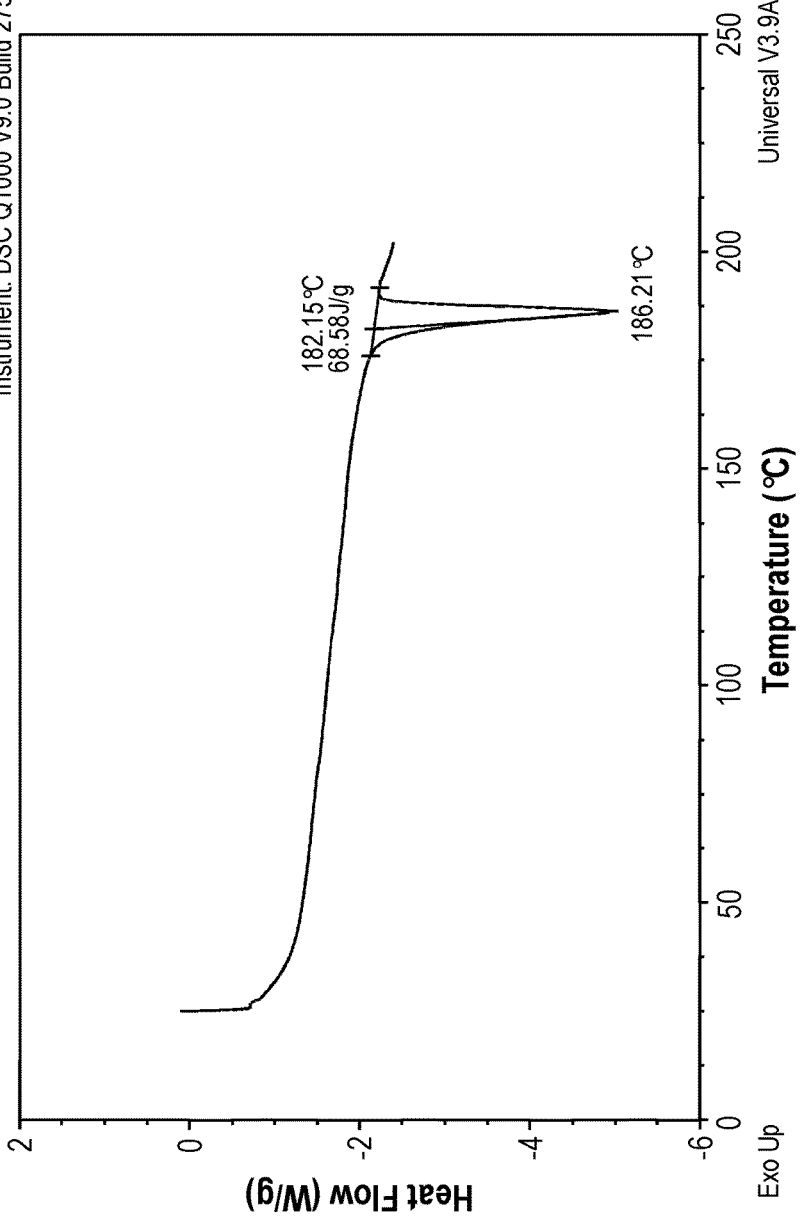
Figure 14C:
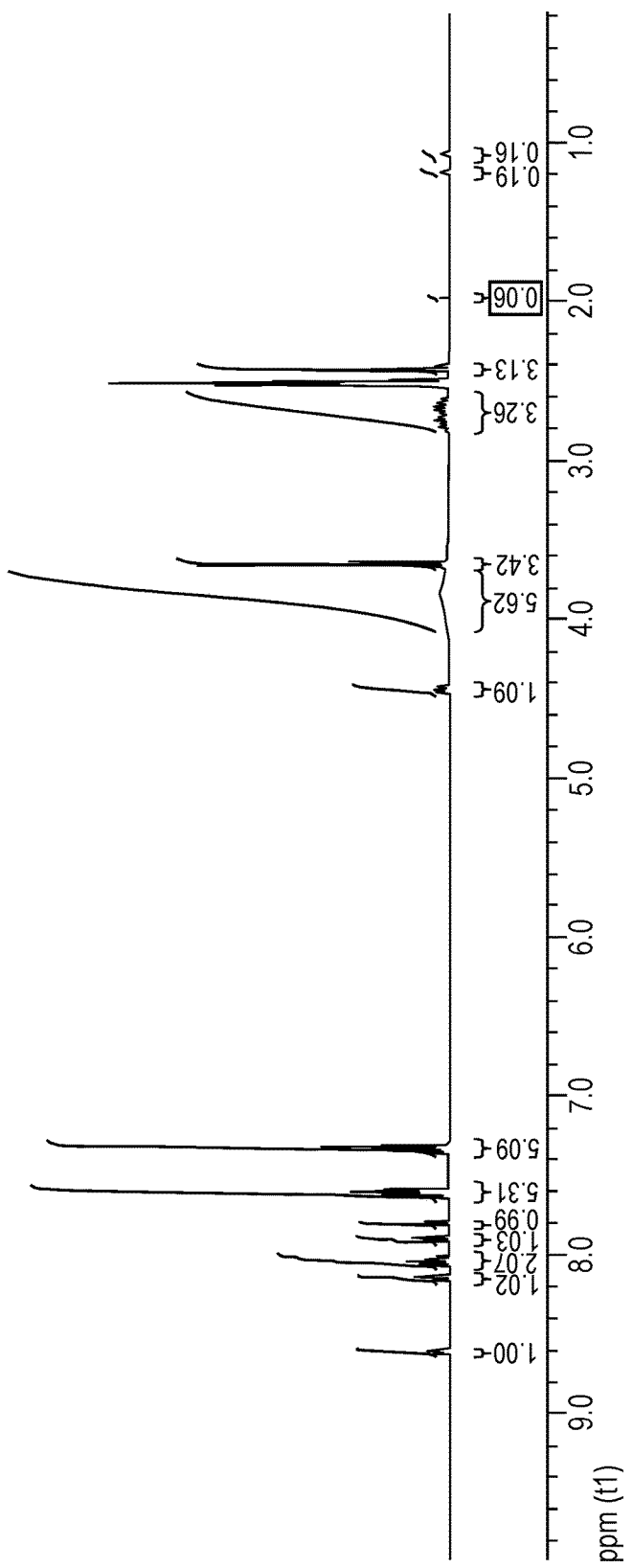
Figure 15A:
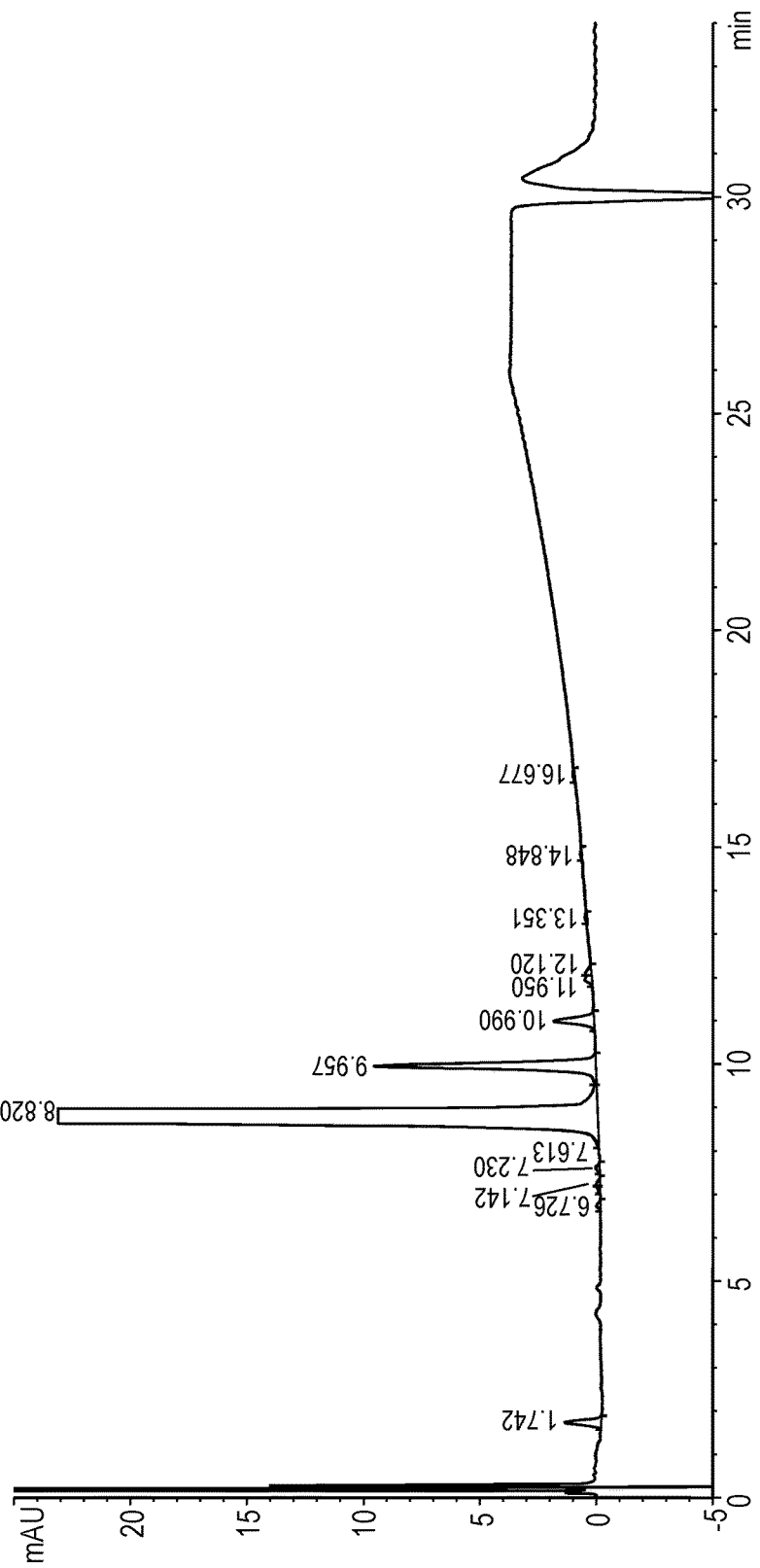
FIGS. 15A and 15B show HPLC chromatographs for release batch of besylate salts, followed by FIGS. 15C and 15D showing Agilent ChemStation reports detailing results.
Figure 15B:
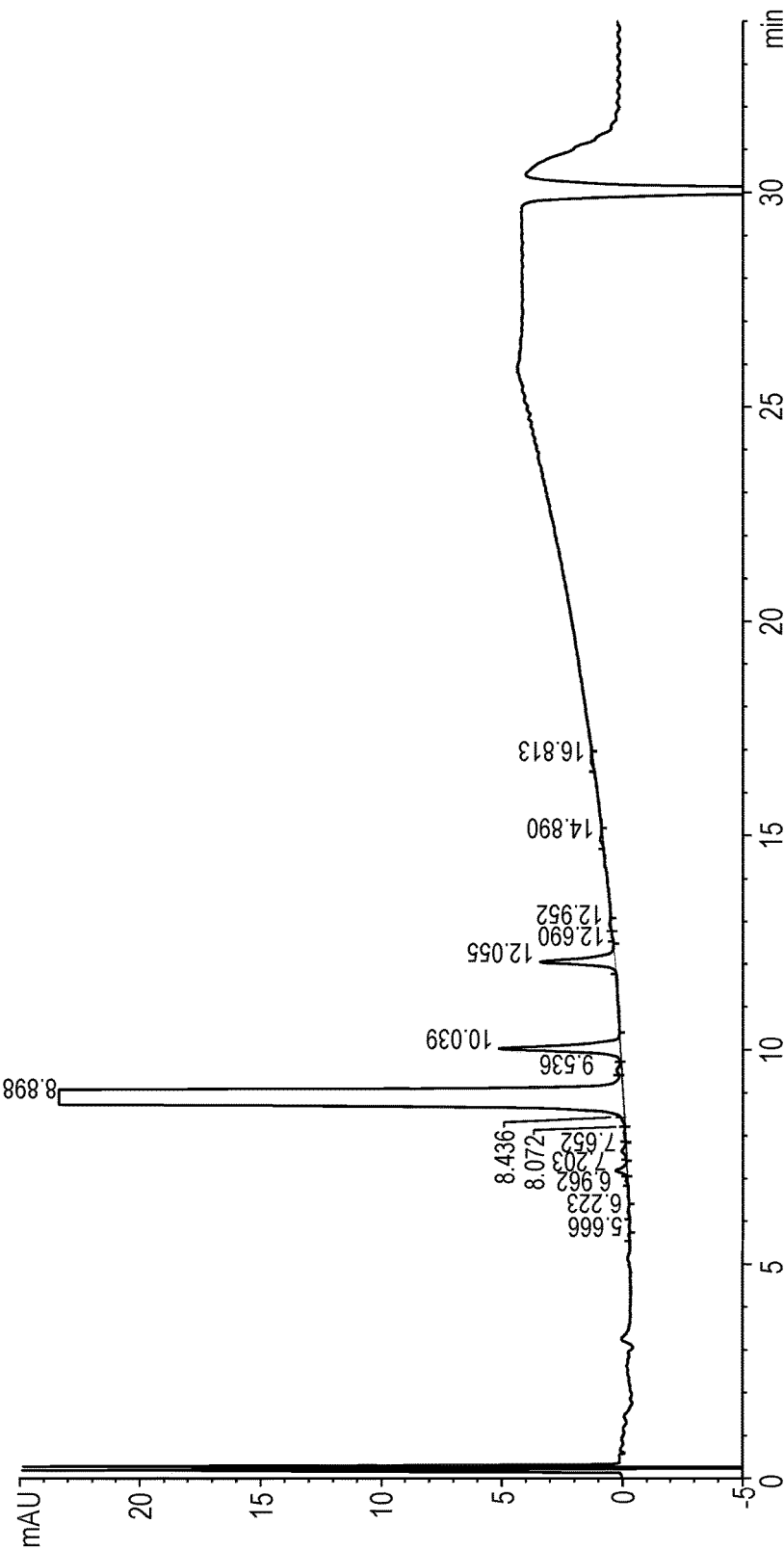
Figure 16A:
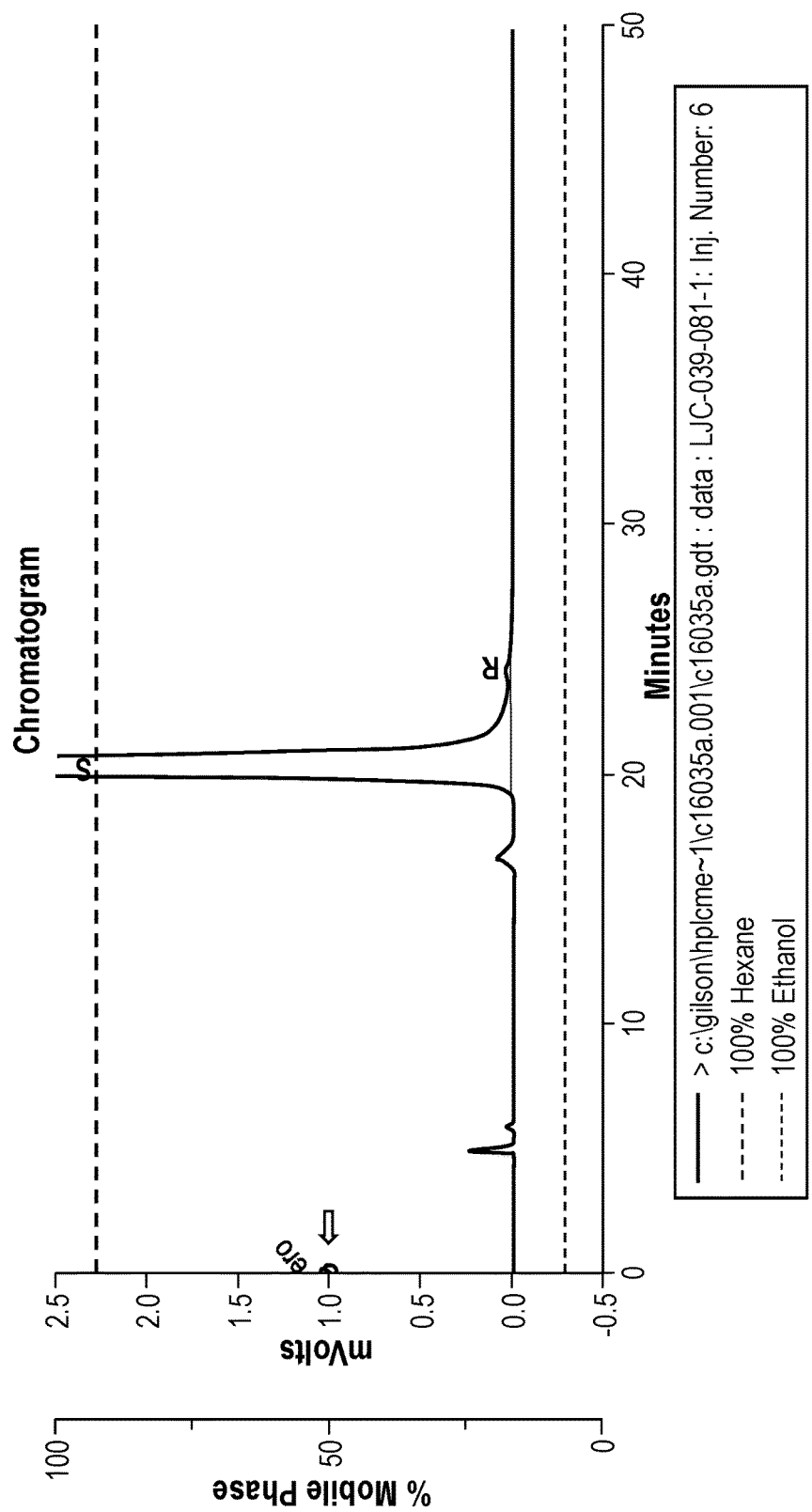
Figure 16B:
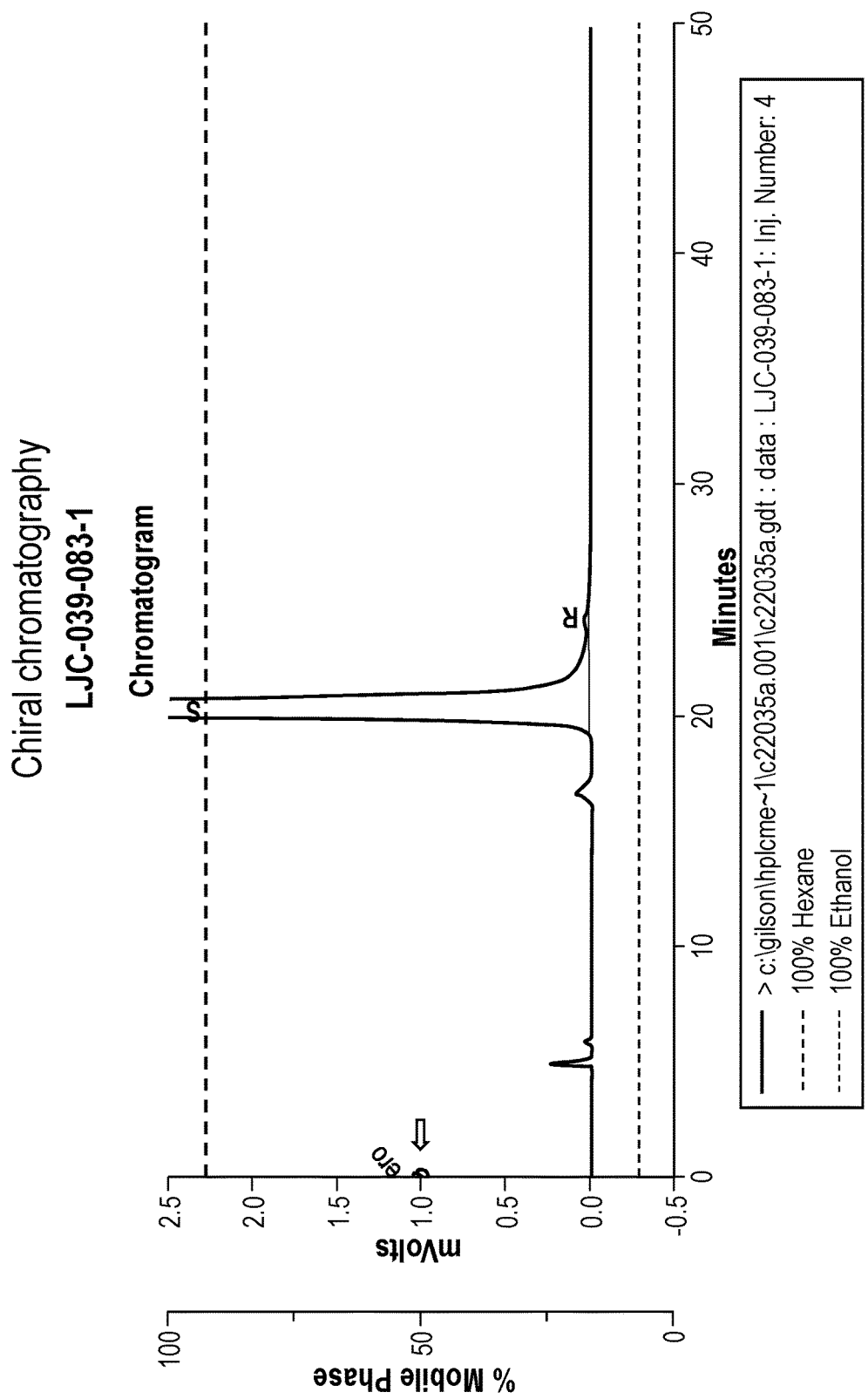
Figure 16C:
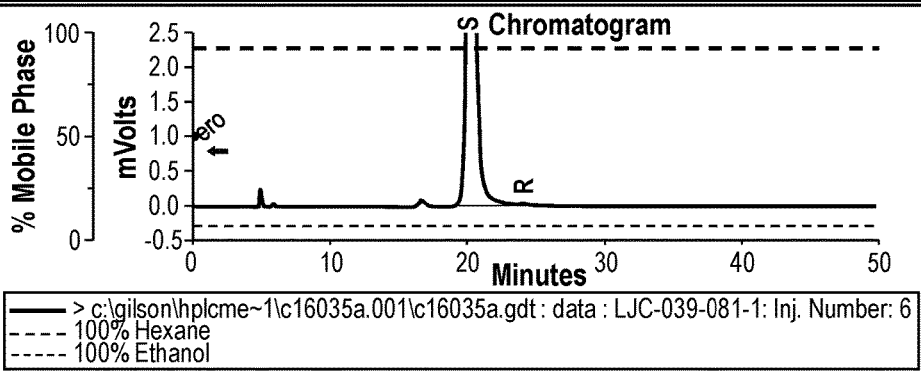

A 100 mg sample was taken for a re-crystallisation attempt from 40% isopropyl acetate/ethanol. The re-crystallisation was carried out traditionally by dissolving the salt in the minimum amount of hot solvent, then cooling slowly to ambient to yield a precipitate. The dried solid was analysed by XRPD which indicated a new form, and with thermal analysis and $^1$H NMR it was confirmed to be a polymorph and not a solvate. FIG. 10 shows DSC of LJC-039-086-1.

The salt screen investigations have shown that compound of formula (I) forms many salts within the appropriate pKa range, and that they are easily isolated from a range of solvents. From full characterisation of the salts, it has been determined that the besylate salts have good stability with respect to humidity. It has been concluded that there are two polymorphic forms of besylate. Form 3 came from the second crop of LJC-039-081-1 liquors after seeding with Form 1. Form 4 has been observed after a re-crystallisation of Form 1 was carried out from 40% isopropyl acetate/ ethanol.

Full analytical data is shown in FIGS. 11-14 below.

Experimental Methods for Examples 2-5

Example 2

Compound of formula (I) (5 mg/well) was dissolved in solvent (ethanol, toluene, and acetonitrile) (30 μl) in HPLC vials. To the solutions, benzene sulfonic acid (11.4 μl, 1M in ethanol) was added and the reaction mixtures stood overnight at ambient. Those vials that contained solid were dried at 40° C. under vacuum, and those that remained as solutions were concentrated by evaporation and then treated with heptane. Those that precipitated were dried as mentioned, and those that oiled were stored at 4° C.

Besylate Form 1 Scale Up

Compound of formula (I) (100 mg) dissolved in ethyl acetate (600 µl) and benzene sulfonic acid (250 µl, 1M in ethanol) added. Precipitation occurred instantly and the reaction mixture was stirred for 24 hours at ambient. The solid was filtered, washed with ethyl acetate and oven dried at 40° C. under vacuum for 16 hours.

Analysis Methods

Differential Scanning Calorimetry (DSC)

DSC data was collected on a TA instrument Q1000 equipped with a 50 position autosampler. The energy and temperature calibration standard was indium. Samples were heated at a rate of 10° C./min between 25 and 350° C. A nitrogen purge at 30 ml/min was maintained over the sample.

Between 0.5 and 3 mg of sample was used, unless otherwise stated, and all samples ran in a pin holed aluminium pan.

Thermogravimetric Analysis (TGA)

TGA data was collected on a TA Instrument Q500 TGA, calibrated with Alumel and running at scan rates of 10° C./minute. A nitrogen purge at 60 ml/min was maintained over the sample.

Typically 5-10 mg of sample was loaded onto a pre-tared platinum crucible unless otherwise stated.

NMR

All spectra were collected on a Bruker 400 MHz equipped with autosampler. Samples were prepared in d6-DMSO, unless otherwise stated.

XRPD (X-Ray Powder Diffraction)

Bruker AXS C2 GADDS Diffractometer

X-ray powder diffraction patterns for the samples were acquired on a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consists of a single Göbel multilayer mirror coupled with a pinhole collimator of 0.3 mm.

Beam divergence, i.e. the effective size of the X-ray beam on the sample, was approximately 4 mm. A θ-θ continuous scan mode was employed with a sample to detector distance of 20 cm which gives an effective 2θ range of 3.2-29.8°. A typical exposure time of a sample would be 120 s.

Samples run under ambient conditions were prepared as flat plate specimens using powder as received without grinding. Approximately 1-2 mg of the sample was lightly pressed on a glass slide to obtain a flat surface. Samples run under non-ambient conditions were mounted on a silicon wafer with heat conducting compound. The sample was then heated to the appropriate temperature at ca. 20° C./minute and subsequently held isothermally for ca 1 minute before data collection was initiated.

Purity Analysis:

Chemical Method

Purity analysis was performed on a HP1100 Agilent:
Method: Gradient, Reverse Phase
Method Duration/min: 34
Column: Phenomenex Gemini C18 5 µm (2.0×50 mm) (Guard cartridge Phenomenex Gemini C18 guard cartridge 2×4 mm)
Column Temperature/° C.: 40
Injection/µl: 5
Flow Rate ml/min: 0.8
Detection: UV
Wavelength/nm: 255 (bandwidth of 90 nm), 240 (bandwidth of 80 nm), 254 (bandwidth of 8 nm)
Phase A: 2 mmol $NH_4HCO_3$ (adjusted to pH10 with $NH_3$ solution)
Phase B: acetonitrile
Timetable:

| Time/Min | % A | % B |
|---|---|---|
| 0 | 90 | 10 |
| 25 | 10 | 90 |
| 28.8 | 10 | 90 |
| 29 | 90 | 10 |
| 34 | 90 | 10 |

Chiral Method

Purity analysis was performed on a Gilson HPLC system:
Method: Isocratic, Normal Phase
Method Duration/min: 50
Column: Diacel Chiralcel OJ-H (5 µm) 4.6×250 mm (Guard cartridge Diacel Chiralcel OJ-H analytical guard cartridge 5 µm 4.0×10 mm)
Column Temperature/° C.: 40
Injection/µl: 10
Flow Rate ml/min: 1.0
Detection: UV
Wavelength/nm: 225 (single wavelength detector)
Phase A: hexane
Phase B: ethanol
Timetable:

| Time/Min | % A | % B |
|---|---|---|
| 0 | 93 | 7 |

Gravimetric Vapour Sorption (GVS) Studies

All samples were run on a Hiden IGASorp moisture sorption analyser running CFRSorp software. Sample sizes were typically 10 mg. A moisture adsorption desorption isotherm was performed as outlined below (2 scans giving 1 complete cycle). All samples were loaded/unloaded at typical room humidity and temperature (40% RH, 25° C.). All samples were analysed by XRPD post GVS analysis. The standard isotherm was performed at 25° C. at 10% RH intervals over a 0-90% RH range unless otherwise stated.

| Scan1 | Scan2 | |
|---|---|---|
| Adsorption | Desorption | Adsorption |
| 40 | 85 | 10 |
| 50 | 75 | 20 |
| 60 | 65 | 30 |
| 70 | 45 | 40 |
| 80 | 35 | |
| 90 | 25 | |
| | 15 | |
| | 5 | |
| | 0 | |

Solubility

This was measured by suspending sufficient compound in 0.25 ml of solvent (water) to give a maximum final concentration of 10 mg/ml of the parent free form of the compound. The suspension was equilibrated at 25° C. for 24 hrs followed by a pH check and filtration through a glass fibre C 96 well plate. The filtrate is then diluted down 101×. Quantitation was by HPLC with reference to a standard dissolved in DMSO at approx 0.1 mg/ml. Different volumes of the standard, diluted and undiluted tests were injected.

The solubility was calculated by integration of the peak area found at the same retention time as the peak maximum in the standard injection. If there is sufficient solid in the filter plate the XRPD is normally checked for phase changes, hydrate formation, amorphization, crystallization etc.
Timetable:

| Time/min | % Phase A | % Phase B |
|---|---|---|
| 0.0 | 95 | 5 |
| 1.0 | 80 | 20 |
| 2.3 | 5 | 95 |
| 3.3 | 5 | 95 |
| 3.5 | 95 | 5 |
| 4.4 | 95 | 5 | pKa Determination pKa determination was performed on a Sirius GlpKa instrument with D-PAS attachment. Measurements were made by potentiometric titration in MeOH:H2O mixtures at 25° C. The titration media was ionic strength adjusted with 0.15M KCl. The values found in the MeOH:$H_2O$ mixtures were extrapolated to 0% co-solvent via a Yasuda-Shedlovsky extrapolation.

Hot Stage Microscopy

Hot stage microscopy was studied using a Leica LM/DM polarised microscope combined with a Mettler-Toledo MTFP82HT hot-stage in the temperature range 25-350° C. with typical heating rates in the range 10-20° C./min. A small amount of sample was dispersed onto a glass slide with individual particles separated as well as possible. Samples were viewed under normal or cross-polarised light (coupled to a λ false-colour filter) with a ×20 objective lens.

Chiral Purity Method
System Setup
Pump: Gilson 322 binary pump
Detector: Gilson 152 UV/Vis
Autosampler: Gilson 233XL rack+Gilson 402 dual syringe pump
Column oven: Phenomenex Thermasphere TS-130
Software: Gilson Unipoint LC software
Column: Daicel Chiralcel OJ-H, 5 µm, 4.6×250 mm
Guard column: Daicel Chiralcel OJ-H analytical guard cartridge, 5 µm, 4.6×10 mm
HPLC Conditions
Channel A: Hexane (93%)
Channel B: Ethanol (7%)
Flow rate: 1.0 ml/min
Detector wavelength 225 nm
Column Temperature: 40° C.
Run time: 50.0 mins
Sample Conditions Approximately 0.2 mg of sample was dissolved in the appropriate volume of Hexane:Ethanol 1:1 v/v to give a 0.2 mg/ml solution. This was capped and placed on a vortex mixer at high speed for a duration of ~15 seconds. If solid remained at this point, then the sample vial was sonicated for approximately 10 seconds followed by a further 10 to 15 seconds on the vortex mixer. 10 µl was injected onto the HPLC system. Samples were injected in duplicate following an initial duplicate injection of Hexane:Ethanol 1:1 v/v as a blank.

Example 5

Pharmacological Test Example

The anaesthetic and sedative effects of the besylate salt Form 1 of the present invention was evaluated. The besylate (benzenesulfonic acid) salt was dissolved in physiological saline for administration of the test composition to the animal. The test composition was administered to mice, placed in individual Plexiglas cages (20×10×10 cm). Mice were injected with either vehicle or test substance by the intravenous route. The latency to sleep and the duration of anaesthesia (maximum: 90 minutes after test-substance administration) were recorded. Anaesthesia is indicated by loss of the righting reflex (LRR). The righting reflex test was performed as soon as the animals appear sedated, approximately every 20-30 seconds. Once the righting reflex is absent, duration of loss of righting reflex was measured by testing for the return of the righting reflex approximately every 20-30 seconds thereafter. Eight mice were studied per group and the test was performed blind. Results from the study are given in the table below.

| TREATMENT (mg/kg) i.v. | NUMBER OF MICE WITH LRR | LATENCY TO LRR (min) mean ± s.e.m. (#) | LRR DURATION (##) (min) mean ± s.e.m. (#) | p value |
|---|---|---|---|---|
| Vehicle | 0 | — | 0.0 ± 0.0 | — |
| CNS 7056X besylate (20.4) | 2 | — | 1.7 ± 1.3 NS | 0.1441 |
| CNS 7056X besylate (27.2) | 5+ | 3.0 ± 0.2 | 4.9 ± 1.6* | 0.0106 |
| CNS 7056X besylate (34) | 6++ | 1.8 ± 0.2 | 6.0 ± 1.9** | 0.0038 |
| CNS 7056X besylate (40.8) | 6++ | 1.6 ± 0.5 | 7.3 ± 2.5** | 0.0038 |

Mann-Whitney U test: NS = Not Significant; *= $p < 0.05$; **= $p < 0.01$
Fisher's Exact test (number of mice with LRR): no indication = not significant; += $p < 0.05$; ++= $p < 0.01$
(#): not calculated if n < 3
(##): maximum = 90 minutes after injection The results in the above table show that the besylate salt Form 1 has a short latency to loss of righting reflex and therefore a short induction time to anaesthesia in the animals. Additionally the mice recover rapidly from anaesthesia as indicated by the short duration of loss of righting reflex. Thus, this compound can provide rapid induction and recovery from anaesthesia.

Example 6

Additional Conditions for Crystallisation of Forms 2, 3, and 4

Additional conditions were tested in an attempt to reproduce the previously reported crystallisations of Forms 2, 3 and 4. However, the reported scales were substantially reduced and the methodology modified accordingly, as described below.

Form 2

5 mg of solid was dissolved in 25 ul of methanol and 10 ul of ethanol added; the solution was then chilled at 4° C. for 3 days.

Form 3

Three variants were attempted:

5 mg of solid was dissolved in 50 ul of ethanol and 120 ul of ethyl acetate added; the solution was then chilled at 4° C. for 3 days.

10.1 mg of solid was dissolved in 300 ul of ethanol and 120 ul of ethyl acetate added; the solution was then chilled at 4° C. for 3 days.

2.5 mg of solid was dissolved in 50 ul of ethanol in a silanized vial and 100 ul of ethyl acetate added; the solution was then chilled at 4° C. for 3 days.

Form 4

Three variants were attempted:

A warmed (70° C.) mixture isopropyl acetate:ethanol (40%:60% v/v) was added to 5 mg of warmed solid in 20 ul aliquots until the solid dissolved (60 ul of solvent mixture in total); the solution was then allowed to cool slowly to ambient in a thermostated waterbath initially at 70° C. over a period of hours.

5 mg of solid was dissolved in 180 ul of warmed (50° C.) isopropyl acetate:ethanol (40%:60% v/v) solvent and the solution allowed to cool slowly to ambient in a thermostated waterbath (initially at 50° C.) over a period of hours.

5 mg portion of solid was dissolved in 100 ul of warmed (50° C.) isopropyl acetate:ethanol (40%:60% v/v) solvent in a silanized vial and the solution allowed to cool slowly to ambient in a thermostated waterbath (initially at 50° C.) over a period of hours.

Each of the crystallisations yielded solid material with blade and plate-like habits, with the Form 4 crystallisations also yielding needle-like material.

Example 7

Characterisation of Compound of Formula (I) Besylate

Compound of formula (I) besylate is chiral and assumed to be of the single enantiomeric form below, i.e. the S enantiomer (consistent with the subsequently determined crystal structures):

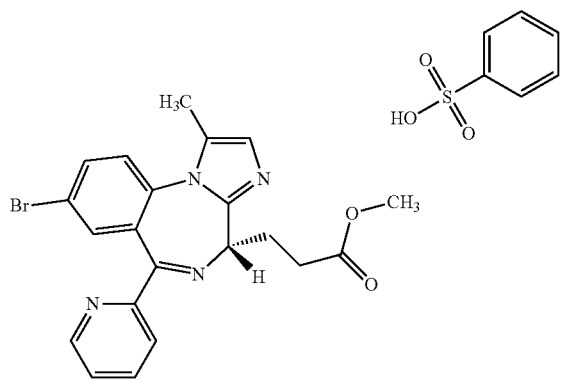 [SMILES: COC(=O)CC[C@@H]1N=C(c2ccccn2)c2cc(Br)ccc2-n2c(C)cnc21 ; O=S(=O)(O)c1ccccc1]

The heterocyclic structure contains a basic Nitrogen in the imidazole ring (pKa of ca. 5), and a weaker basic Nitrogen in the pyridyl ring (pKa of ca. 2). The imidazole-Nitrogen will typically be protonated in the presence of the strongly acidic besylate (pKa ca. −0.6) in aqueous solution, with the pyridyl-Nitrogen also potentially being protonated under conditions of excess besylate.

The neutral free base form (i.e. unprotonated) of the compound is expected to be somewhat lipophilic (log $P_{octanol:water}$ ca. 4.0) and thus would prefer some lipophilic environments over aqueous ones. Moreover, it is likely to retain a degree of lipophillicity even when monoprotonated (log $D_{octanol:water}$ ca. 2 at pH3), although the effect of the besylate counter-ion is likely to ameliorate this tendency through its inherent hydrophilicity. The degree of lipophilicity further diminishes for the diprotonated form (log $D_{octanol:water}$ ca. 0.6 at pH0).

The compound also has an excess of Hydrogen bond acceptors and therefore will be suitably partnered by Hydrogen bond donating solvents. It is thus expected that the compound will prefer solubilisation in a range of polar organic solvents such as the alcohols, particularly those which provide a partially lipophilic, Hydrogen bond donating environment. This has been borne out by experimental evidence (details of solvents used are given in Example 8):

| Solvent | Observed solubility (mg/ml) |
| --- | --- |
| Formamide | 350 |
| Water | 2 |
| Dimethyl sulfoxide | 500 |
| Dimethylacetamide | 200 |
| 1,2-ethanediol | 60 |
| Dimethylformamide | 300 |
| Acetonitrile | >20 |
| Methanol | 400 |
| 2-ethoxyethanol | 20 |
| 2,2,2-trifluoroethanol | 1000 |
| Ethanol | 100 |
| Acetone | 2 |
| Propan-1-ol | 15 |
| Propan-2-ol | 4.8 |
| 2-methoxyethanol | 167 |
| Hexafluoropropan-2-ol | >700 |
| Dichloromethane | <<0.3 |
| Tetrahydrofuran | 2.5 |
| Methylbenzoate | 2 |
| Ethyl acetate | 0.2 |
| Chloroform | <<0.4 |
| 1,4-dioxan | 1 |

Soluble (>5 mg/ml), partially soluble (2.5-5 mg/ml), partially insoluble (0.5-2.5 mg/ml, insoluble (<0.5 mg/ml).
Values quoted are approximate, but experimentally confirmed.

These results highlight the good solubility of the compound in a wide variety of polar organic solvents. In particular, 2,2,2-trifluoroethanol and hexafluoropropan-2-ol are both identified as extremely good solvents for this compound. This is consistent with the considerations discussed above, both solvents being strong Hydrogen bond donors. Likewise, the more substantially lipophilic solvents are identified as poor solvents and thence potential anti-solvents for crystallisations.

Example 8

Compound of Formula (I) Besylate Crystallisations

Various conditions conducive to obtaining crystalline material of compound of formula (I) besylate Forms 1 and 2 are described. Crystallisation conditions which include alcohols or acetonitrile solvents as components, with their respectively compatible anti-solvents or co-solvents, are believed to provide the most promising conditions to yield useful crystalline material. Crystallisation using solvent/anti-solvent binary mixtures was primarily used. Crystallisations were performed by retarded evaporation from sub-saturated solutions of the compound in solvent/anti-solvent mixtures, at ambient and reduced (4° C.) temperature. Crystallisation was typically observed within 3-5 days of preparation.

Where sample quantity allowed, all crystallisation conditions were performed in duplicate in a glass 96-wellplate format; one half of each wellplate being used to duplicate the conditions in the other half of the wellplate. Cross-contamination between wells is minimised by design. All of the conditions tested behaved reproducibly in at least duplicate, most yielding solid material suitable for further analysis.

In all cases, equipment coming into contact with samples and crystallisation media were scrupulously cleaned with a variety of solvents and reagents before being bathed in ethanol and blown dry using copious evaporated nitrogen.

High quality solvents from commercial suppliers were employed, as described in Table 12.

TABLE 12

| Solvent | Supplier | Cat. No. | Batch No. | Grade | Purity |
|---|---|---|---|---|---|
| 1,2-dichlorobenzene | Romil | H177 | E558470 | SpS | >99.8% |
| 1,4-dimethylbenzene | Fluka | 95682 | 429739/1 | puriss p.a. | >99% |
| 1,4-dioxan | Romil | H297 | H540480 | SpS | >99.9% |
| 2,2,2-trifluoroethanol | Romil | H860 | M538412 | SpS | >99.9% |
| acetonitrile | Romil | H049 | D531490 | SpS | >99.9% |
| dimethylacetamide | Romil | H249 | B540480 | SpS | >99.9% |
| dimethylsulfoxide | Romil | H280 | W530480 | SpS | >99.9% |
| ethanol | Romil | H314 | O533480 | SpS | >99.8% |
| ethyl acetate | Romil | H346 | T533480 | SpS | >99.9% |
| methyl iso-butyl ketone | Romil | H446 | M539430 | SpS | >99.9% |
| n-nonane | Romil | H568 | O558450 | SpS | >99.9% |
| pentylacetate | Fluka | 46022 | 13248/1 | puriss p.a. | >98.5% |
| propan-1-ol | Romil | H624 | G531460 | SpS | >99.9% |
| propan-2-ol | Romil | H625 | O530480 | SpS | >99.9% |
| tetrachloroethylene | Romil | H702 | W536450 | SpS | >99.9% |
| tetrahydrofuran | Romil | H718 | B532470 | SpS | >99.9% |
| Acetone | Romil | H031 | E559470 | SpS | >99.9% |
| Chloroform | Romil | H135 | B554470 | SpS | >99.9% |
| Dichloromethane | Romil | H202 | O554460 | SpS | >99.9% |
| Dimethylformamide | Romil | H253 | T546460 | SpS | >99.9% |
| Formamide | Romil | H351 | Q537480 | BioPure | >99.9% |
| Hexafluoropropan-2-ol | Romil | H359 | H559470 | SpS | >99.9% |
| Methylbenzoate | Fluka | 12460 | 417868/1 | purum | >98% |
| water | Romil | H950 | D537480 | SpS | >99.9% |

Visual analysis of the resulting crystalline morphologies was achieved using a binocular microscope (ca. 10×-40× magnification) with digital camera attached, employing both transmitted and reflected lighting as appropriate.

Visual characterisation of the solid material is summarised in Table 14 below. A predominance of blade or tabular/plate morphologies, either as unique crystals or as spherulites, was observed. Over all, there was little morphological difference between the crystallisations performed at ambient temperatures and those at 4° C., with the exception of those with ethanol as solvent where the tendency for spherulite and interface type growth diminished with lowered temperature. It is notable that the use of anti-solvent can improve the quality of the crystalline material substantially.

Figure 17:
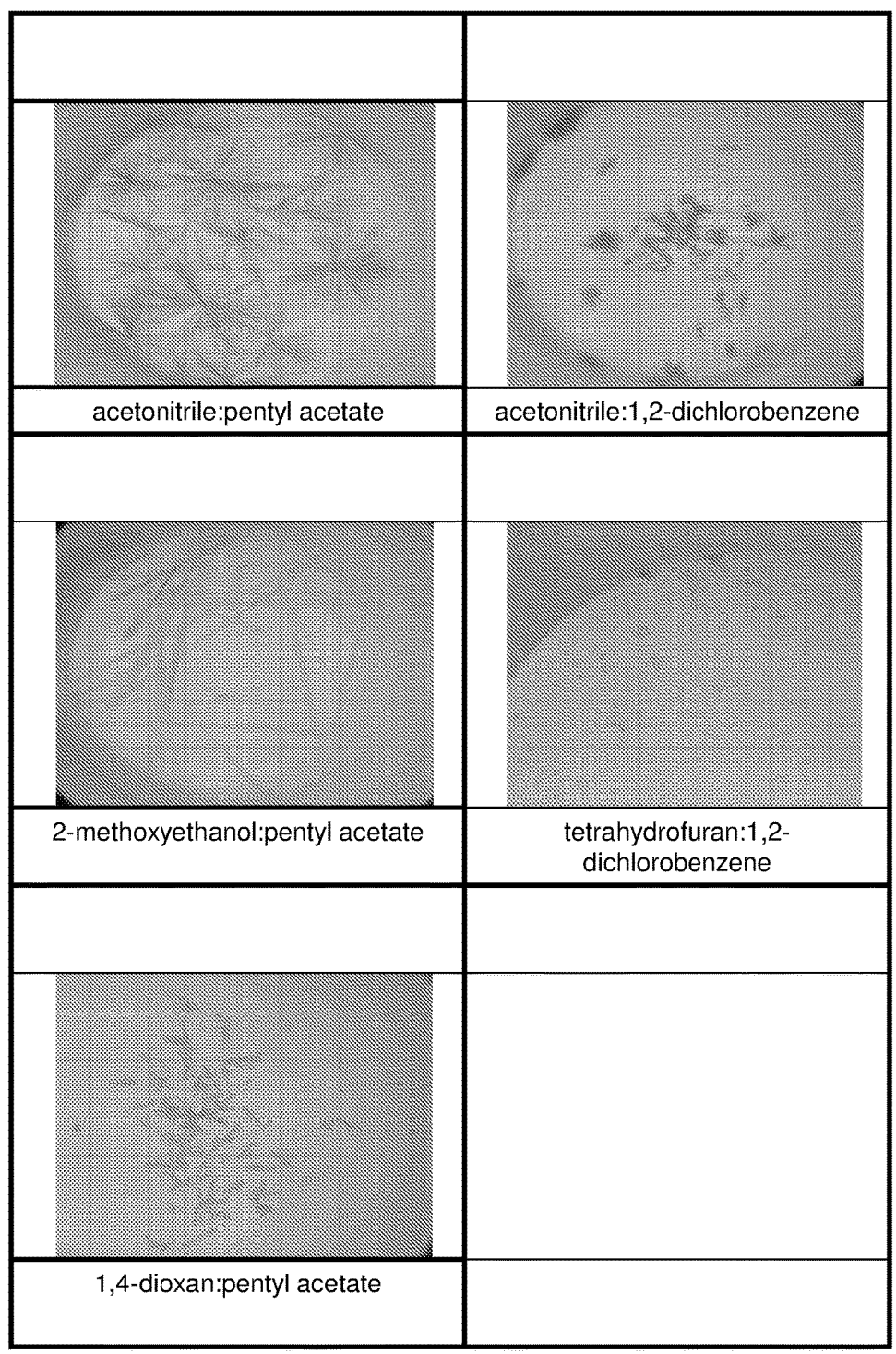
FIG. 17 shows exemplar images (ca. 4-8 mm diameter field of view) of the solid forms observed in crystallisations of compound of formula (I) besylate.

Example images of the crystalline material observed are presented in FIG. 17. As illustrated in this Figure, acetonitrile has a tendency to produce spherulite growth, typically seen as a consequence of poor nucleation and thence growth from poor quality crystal surfaces. In contrast, 2-methoxyethanol has a tendency to produce unique crystals of blade/needle-like morphology.

There appears to be a general preference for Form 1 to crystallise from many of the conditions. However, it is notable that Form 2 has also been observed from several crystallisation conditions, including the scaled-down analogues for obtaining Forms 3 and 4 (described in Example 6). Form 2 is observed in conditions where there are extremes of either polarity (acetonitrile:water) or lipophilicity (n-nonane) or both (dimethyl sulfoxide:1,2-dichlorobenzene). In general, the crystals of Form 2 were notable in their superior quality and distinctive well-formed plate/tabular habit.

Single Crystal X-Ray Diffraction Cell Determinations

To provide corroborative evidence of the crystalline forms generated, the cell parameters of a number of crystals of suitable quality were determined using single crystal X-ray diffraction. Crystal unit cell parameters were determined using a Kappa CCD diffractometer with Mo radiation, the crystals mounted on a glass fibre with oil and held at 260K. The parameters for Form 1 and Form 2 have been determined as summarised in Table 13.

TABLE 13

Cell parameters determined for crystals of compound of formula (I) besylate.

|  | Form 1 | Form 2 |
|---|---|---|
| Crystal State |  |  |
| Solvent | 2-methoxyethanol | ethanol |
| Anti-solvent/Co-solvent | pentyl acetate | ethyl acetate |
| Crystal Morphology | needle | plate |
| Crystal Size (mm) | 0.8 × 0.04 × 0.02 | 0.7 × 0.3 × 0.25 |
| Colour | colourless | colourless |
| Crystal Structure |  |  |
| System | monoclinic | orthorhombic |
| Unit Cell a (Å) | 7.6868 (1) | 8.92130 (10) |
| b (Å) | 29.2607 (5) | 11.1536 (2) |
| c (Å) | 12.3756 (3) | 25.8345 (4) |
| α (°) | 90 | 90 |
| β (°) | 97.7880 (8) | 90 |
| γ (°) | 90 | 90 |
| Volume (Å$^3$) | 2757.86 (9) | 2570.65 (7) |

The crystallisation results from solvent/co-solvent and solvent/anti-solvent conditions for compound of formula (I) besylate with single crystal X-ray diffraction unit cell results are tabulated in Table 14.

TABLE 14

Experimental crystallisation results from solvent/co-solvent and solvent/anti-solvent conditions for compound of formula (I) besylate, with single crystal X-ray diffraction unit cell results (X-ray results for ambient crystallisations unless otherwise stated).

| Solvent | Co/Anti-solvent (& conditions) | Observed Crystallisations Habit | X-ray Form (No & habit of crystals) |
|---|---|---|---|
| methanol | ethanol (at 4° C., 3 days) | blades & plates | 2 (hex, blade) |

TABLE 14-continued

Experimental crystallisation results from solvent/co-solvent and solvent/anti-solvent conditions for compound of formula (I) besylate, with single crystal X-ray diffraction unit cell results (X-ray results for ambient crystallisations unless otherwise stated).

| Solvent | Co/Anti-solvent (& conditions) | Observed Crystallisations Habit | X-ray Form (No & habit of crystals) |
|---|---|---|---|
| ethanol | ethyl acetate (at 4° C., 3 days) | blades & plates | 2 (4 plates) |
| ethanol | ethyl acetate | blades & plates | 2 (6 plates) |
| isopropyl acetate | ethanol (70° C. → 20° C.) | blades, plates & needles | 2 (2 plates) |
| isopropyl acetate | ethanol (50° C. → 20° C.) | blades & plates | 2 (2 hex plates, 2 plates, 2 blades) |
| ethanol | methyl isobutyl ketone (at 4° C., 3 days, silanized vial) | tabular plates | 2 (3 plates) |
| ethanol | p-cymene (at 4° C., 3 days, silanized vial) | plate & tabular | 2 (2 tabular) |
| nonane | none (silanized vial) | blades & plates | 2 (plate) |
| dimethylsulfoxide | 1,2-dichlorobenzene | intergrown blades dendrite, one huge tabular | 2 (tabular) |
| dimethylacetamide | methyl isobutyl ketone | plate-like fragments | 1 (blade) |
| dimethylacetamide | tetrachloroethylene | intergrown blades | 1 (2 blades) |
| acetonitrile | water | interface | 2 (2 tabular) |
| acetonitrile | 3-methylbutan-1-ol | triangular plates, fragments & dendrite | 1 (blade) |
| acetonitrile | 1,2-dichlorobenzene | spherulite blades | 1 (2 blades) |
| acetonitrile | pentyl acetate | spherulite blades | 1 (blade) |
| methanol | none | interface plates | 2 (plate) |
| methanol | 3-methylbutan-1-ol | triangular plates & fragments | 1 (2 blades) |
| methanol | methyl isobutyl ketone | fragments & blade | 1 (blade) |
| 2,2,2-trifluoroethanol | 1,2-dichlorobenzene | interface & blade opaque & translucent blades | 1 (trans, blade) |
| 2,2,2-trifluoroethanol | 1,4-dimethylbenzene | plate-like fragments | 1 (sph, plate) |
| ethanol | methyl isobutyl ketone | interface plates (5° C.: tabular & plate) | 1 (interface), 2 (tabular) |
| ethanol | 1,2-dichlorobenzene | interface plates, (5° C.: needles) | 2 (plate) |
| ethanol | tetrachloroethylene | interface (5° C.: hexagonal tabular) | 2 (blade 4° C.) |
| ethanol | 1,4-dimethylbenzene | interface blades | 1 (blade) |
| propan-1-ol | none | plate-like fragments | 1 (plate) |
| propan-1-ol | 1,2-dichlorobenzene | interface | 1 (blade) |
| propan-1-ol | tetrachloroethylene | plate-like fragments & interface | 1 (blade) |
| propan-2-ol | 1,2-dichlorobenzene | fan needles & dendrite | 1 (blade) |
| propan-2-ol | n-nonane | blades, needles & spherulite needles | 1 (needle) |
| 2-methoxy ethanol | water | blade | 1 (2 blades) |
| 2-methoxy ethanol | pentyl acetate | needles | 1 (blade) |
| 2-methoxy ethanol | 1,4-dimethylbenzene | blades & needles | 1 (blade) |
| 2-methoxy ethanol | n-nonane | blades & dendrite | 1 (blade) |

TABLE 14-continued

Experimental crystallisation results from solvent/co-solvent and solvent/anti-solvent conditions for compound of formula (I) besylate, with single crystal X-ray diffraction unit cell results (X-ray results for ambient crystallisations unless otherwise stated).

| Solvent | Co/Anti-solvent (& conditions) | Observed Crystallisations Habit | X-ray Form (No & habit of crystals) |
|---|---|---|---|
| tetrahydrofuran | water | plate | 1 (plate) |
| tetrahydrofuran | 3-methylbutan-1-ol | intergrown blades | 1 (plate) |
| tetrahydrofuran | 1,2-dichlorobenzene | prismatic tabular, fragments, powder | 2 (3 tabular) |
| tetrahydrofuran | ethyl acetate | dendrite, interface | 2 (plate 4° C.) |
| tetrahydrofuran | isopropyl acetate | intergrown plates & intergrown blades | 1 (plate) |
| tetrahydrofuran | 1,3-dimethylbenzene | intergrown blades | 1 (blade) |
| 1,4-dioxane | pentyl acetate | triangular plates, some part of spherulite | 1 (2 tri plate) |
| 1,4-dioxane | 1,4-dimethylbenzene | blade | 1 (blade) |

A variety of crystals of suitable quality for full single crystal X-ray diffraction crystal structure determination were achieved and the full structure obtained for Forms 1 and 2. These crystal structures are reported in Examples 9 and 10.

Example 9

Crystal Structure of Form 1

Crystals of compound of formula (I) besylate grown from a 2-methoxyethanol:pentyl acetate solution which have a needle habit, are imaged in FIG. 17.

A single needle habit crystal (ca. 0.8×0.04×0.02 mm in size) was selected and its cell parameters determined at 260K and then at 190K. No transition was observed on lowering the temperature between 260-190K. The structure analysed here is for the data at 190K; parameters of the crystal and the X-ray diffraction refinement are given in Table 15.

TABLE 15

Data of the 2-methoxyethanol:pentyl acetate grown crystal of compound of formula (I) besylate, Form 1.

| Crystal State | |
|---|---|
| Code | CNS7056 besylate |
| Solvent | 2-methoxyethanol |
| Anti-solvent/Co-solvent | pentyl acetate |
| Crystal Morphology | needle |
| Crystal Size (mm) | 0.8 × 0.04 × 0.02 |
| Colour | colourless |
| Crystal Structure | |
| Formula | $C_{54}H_{50}Br_2N_8O_{10}S_2$ |
| Formula Weight | 1194.98 |
| System | monoclinic |
| Space Group | $P\,2_1$ |
| Unit Cell a (Å) | 7.6868 (1) |
| b (Å) | 29.2607 (5) |
| c (Å) | 12.3756 (3) |
| α (°) | 90 |
| β (°) | 97.7880 (8) |
| γ (°) | 90 |
| Volume (Å$^3$) | 2757.86 (9) |
| Z (No. molecules in unit) | 2 |

TABLE 15-continued

Data of the 2-methoxyethanol:pentyl acetate grown crystal of compound of formula (I) besylate, Form 1.

| | |
|---|---|
| Z' (No. molecules in asymmetric unit) | 2 |
| Density (g cm$^3$) | 1.439 |
| Absorption μ [MoKα] (mm$^{-1}$) | 1.610 |
| F(000) | 1224 |
| Data Collection | |
| Temperature, (K) | 190 |
| Instrument | Kappa CCD diffractometer |
| Scan Type | ω |
| Absorption Correction Type | multi-scan |
| No. of Measured Reflections | 9868 |
| No. of Independent Reflections | 9848 |
| θ min/max (°) | 1.80/27.49 |
| h min/max | −9/9 |
| k min/max | −37/36 |
| l min/max | −15/15 |
| Refinement | |
| Refinement On | F |
| I/σ(I) Cut-off | 3 |
| No. of Used Reflections | 6821 |
| No. of Parameters | 686 |
| R factor (%) | 6.34 |
| Rw factor (%) | 6.39 |
| S | 1.00 |
| Δρ(min) Å$^{-3}$ | −0.8 |
| Δρ(max) Å$^{-3}$ | 0.8 |
| Max Shift/Error | 0.0005 |
| Flack Parameter | 0.027 (11) |

Figure 18:
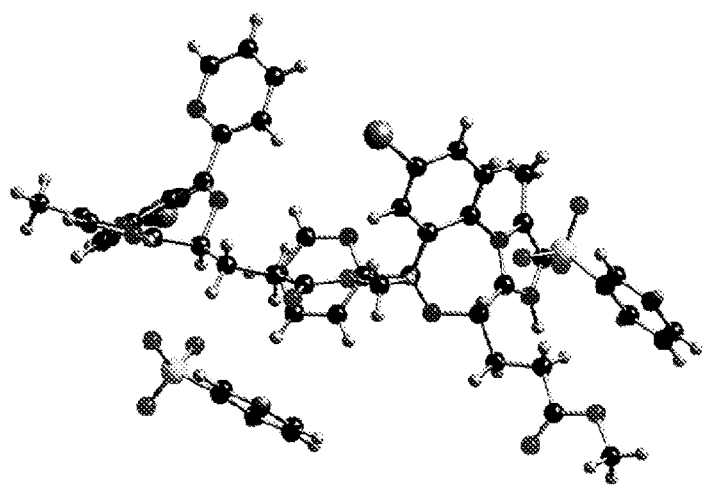
FIG. 18 shows content of the asymmetric unit in Form 1.
Figure 18:

The content of the asymmetric unit is displayed in FIG. 18. It consists of two independent molecules of the compound and two independent besylate counter ions. Each compound has the imidazole-Nitrogen protonated.

The Flack "Enantiopole" parameter was determined as 0.03(1) and thus the stereochemistry of the structures depicted here are well established and are consistent with the purported stereochemistry for the compound:

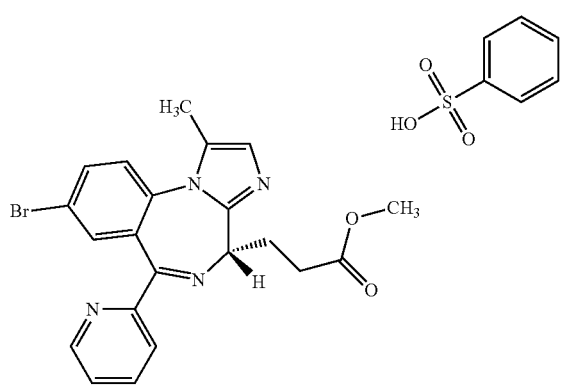 [SMILES: COC(=O)CC[C@@H]1N=C(c2ccccn2)c2cc(Br)ccc2-n2c(C)cnc21 ; O=S(=O)(O)c1ccccc1]

Crystallographic co-ordinates and other relevant data are tabulated in the form of a SHELX file in Table 17.

Figure 19:
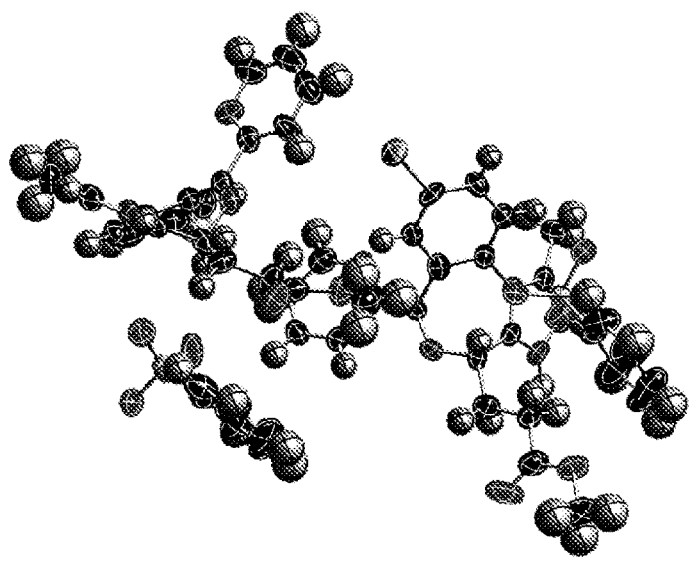
FIG. 19 shows molecular structure as determined by single-crystal X-ray diffraction of a crystal of compound of formula (I) besylate, Form 1, grown from a 2-methoxyethanol:pentyl acetate solution with atoms represented by thermal ellipsoids. Only hydrogens specifically located in the crystal structure are depicted.
Figure 19:

The conformational disorder can be represented (in first approximation) by the "thermal ellipsoids" of the atomic positions, as presented on FIG. 19. It can be seen that the major regions of disorder lie in the methyl groups and in the besylate.

Figure 20:
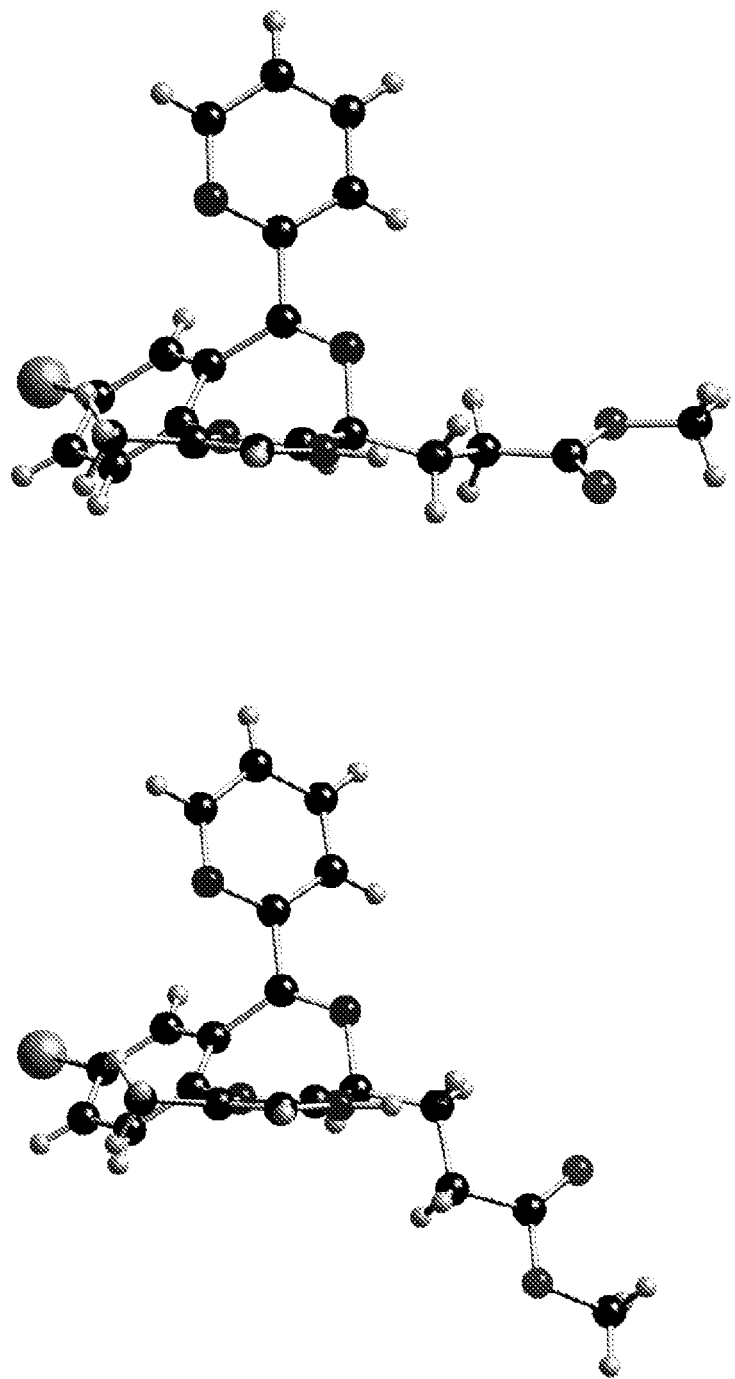
FIG. 20 shows conformation adopted by the two independent molecules in Form 1.

The difference between the two independent molecules comes mainly from the ester chains as seen in FIG. 20. One molecule has the ester chain being coplanar with the imidazole ring, whereas the other molecule has the ester chain being orthogonal.

Figure 21:
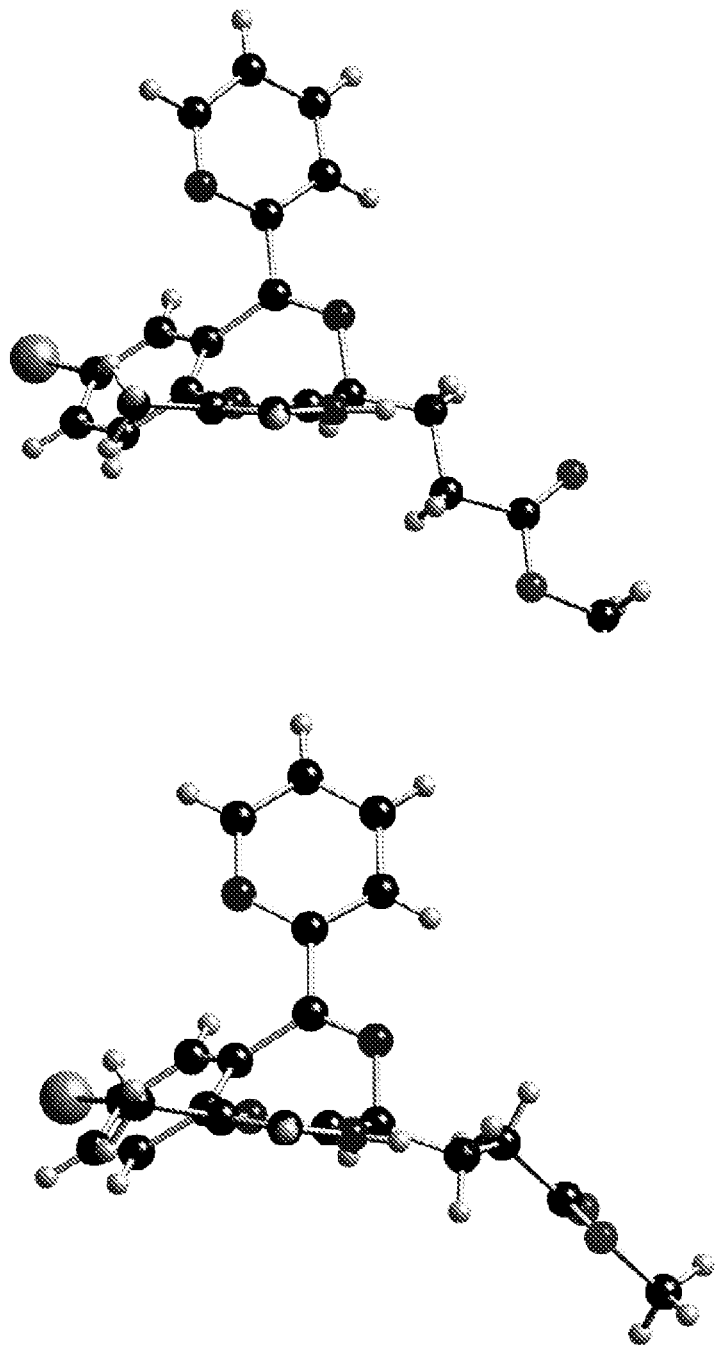
FIG. 21 shows comparison of the conformation adopted by one independent molecule in Form 1 (top) and the conformation in Form 2 (bottom)

The conformation of the ester chains are different to that adopted in Form 2 (FIG. 21). The orthogonal conformation observed in Form 1 bears the greatest similarity to that found in Form 2.

Figure 22:
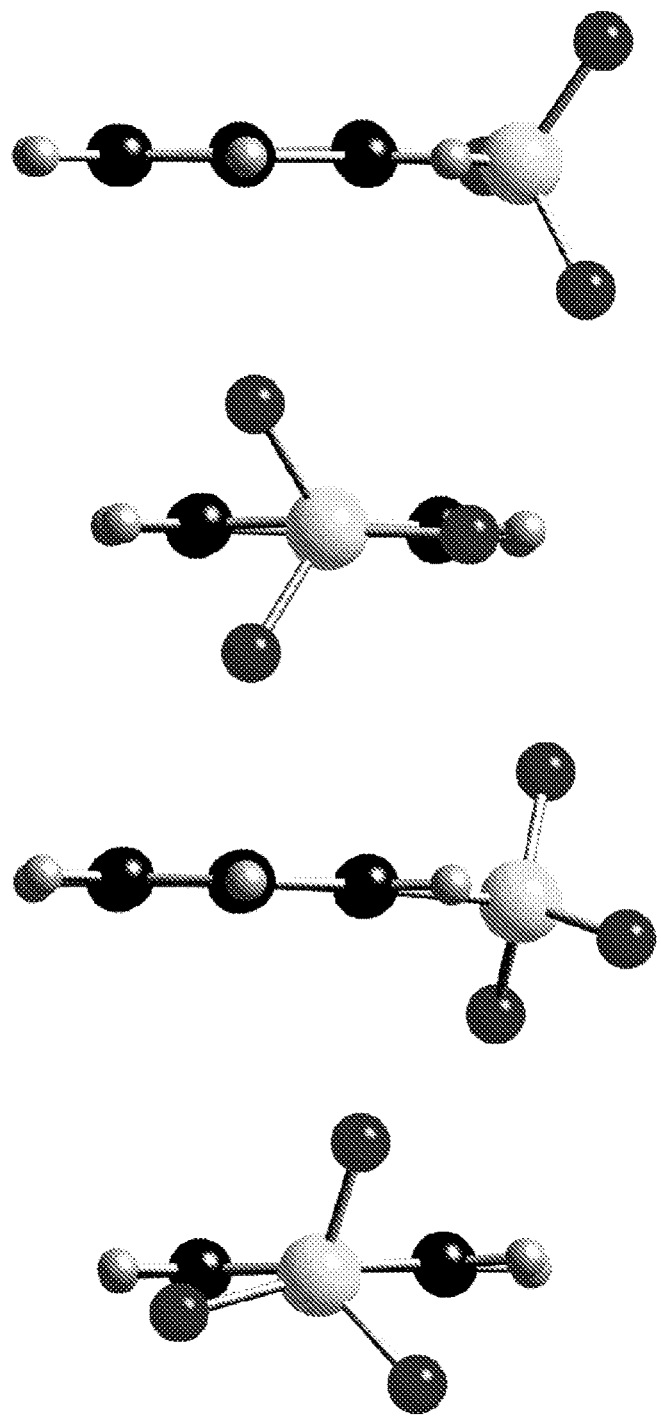
FIG. 22 shows comparison of the conformation adopted by the two independent besylates in Form 1, view along two different directions.

The two independent besylates have staggered conformations (FIG. 22). No substantial differences in bond lengths are apparent.

Figure 23:
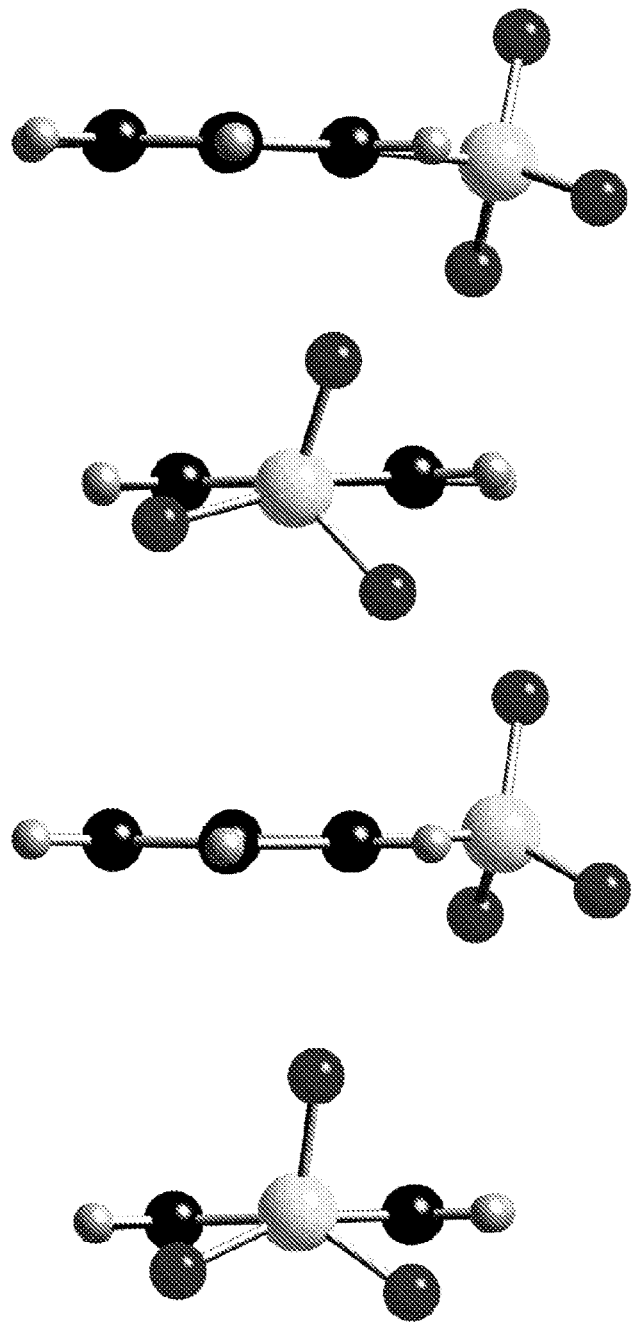
FIG. 23 shows comparison of the conformation adopted by one independent besylate in Form 1 (top) and the conformation in Form 2 (bottom)

One besylate adopts the conformation observed for the besylate in Form 2 (FIG. 23).

Figure 24B:
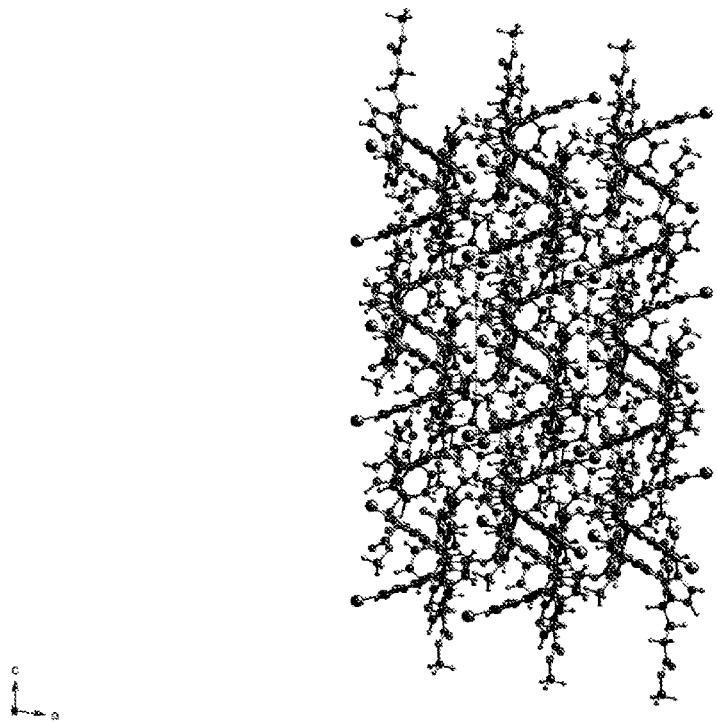
Figure 24C:
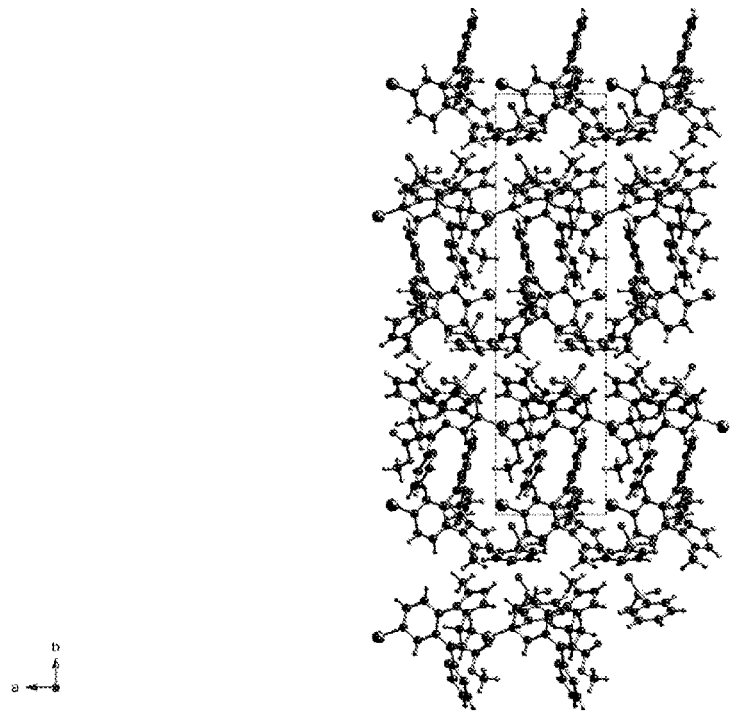
Figure 25:
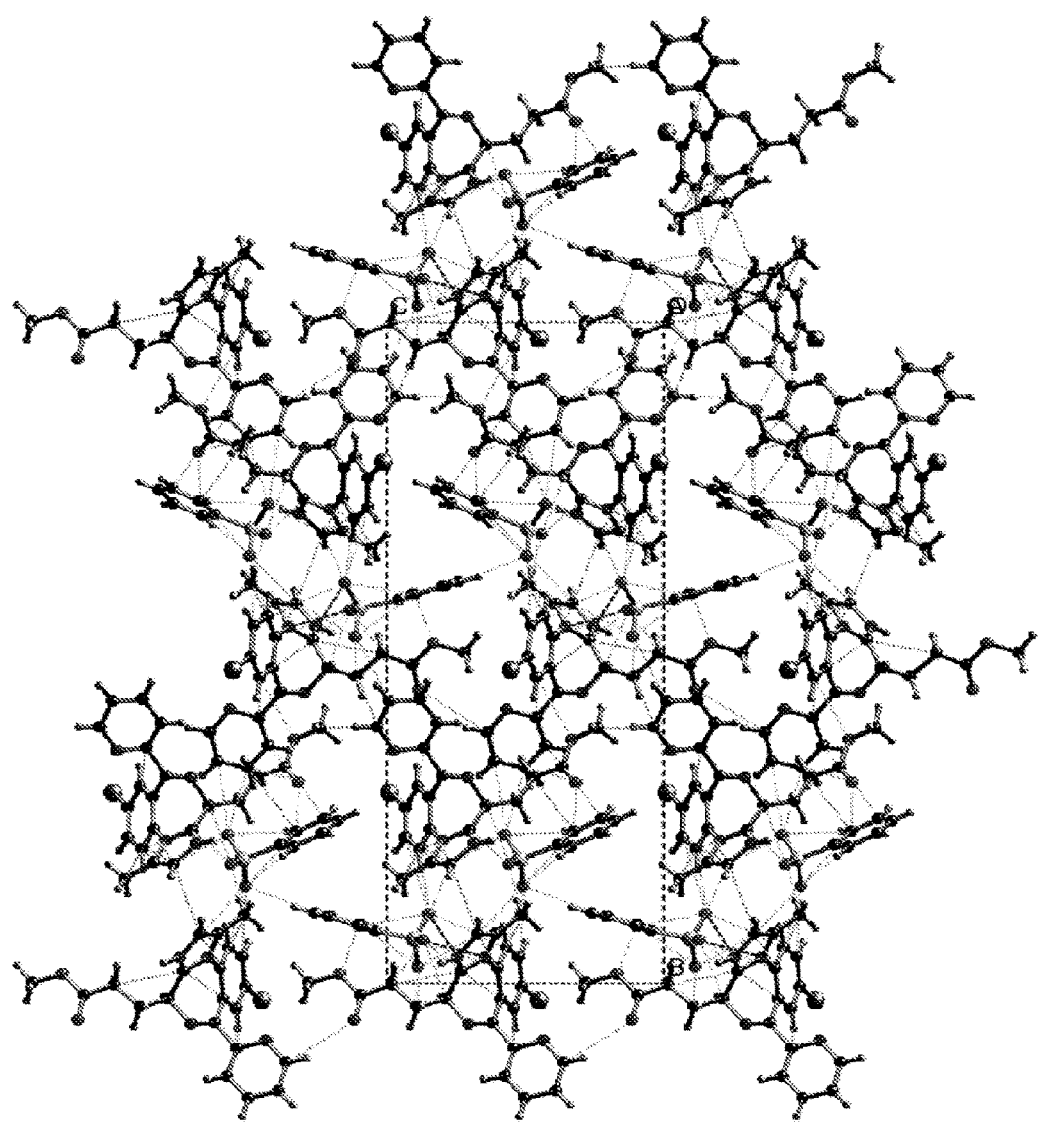
FIG. 25 shows short contact C—O<3.6 Å, C—C<3.6 Å, and N—O<3.5 Å for Form 1.

The resolved crystal structure, viewed along the crystallographic a, b and c axes, is illustrated in FIGS. 24*a*, *b* and *c* respectively. FIG. 25 summarises the shortest contacts observed in the crystal packing.

Each compound interacts with the two independent besylates. In particular, a short distance (hydrogen-bond type) is established between one oxygen atom of one besylate and the protonated nitrogen of the imidazole ring of the compound. The second independent compound interacts similarly, but with the second independent besylate.

Other close contacts (C—O, H—O) are observed between the compounds and the besylates mainly in the vicinity of the imidazole and pyridyl ring. Some close contacts are also observed between the two compounds themselves (Br—N, C—C, O—H) and the two besylate themselves (O—H contacts) but to a lesser extent for the latter.

Figure 26:
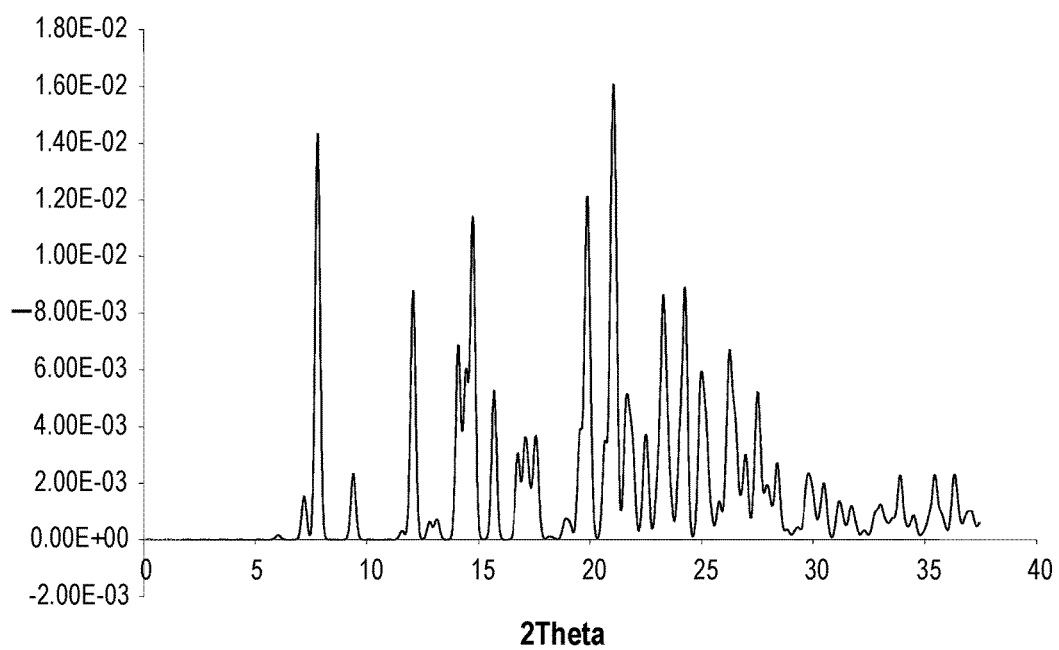
FIG. 26 shows calculated powder pattern diffraction from single crystal X-ray diffraction data for Form 1.

Using the crystal structure determined experimentally, a powder diffraction pattern for Form 1 has been calculated using CrystalDiffract® (CrystalDiffract is a registered TradeMark of CrystalMaker Ltd) and is depicted in FIG. 26. This powder pattern matches the experimental powder pattern reported for Form 1.

Example 10

Crystal Structure of Form 2

Figure 27:
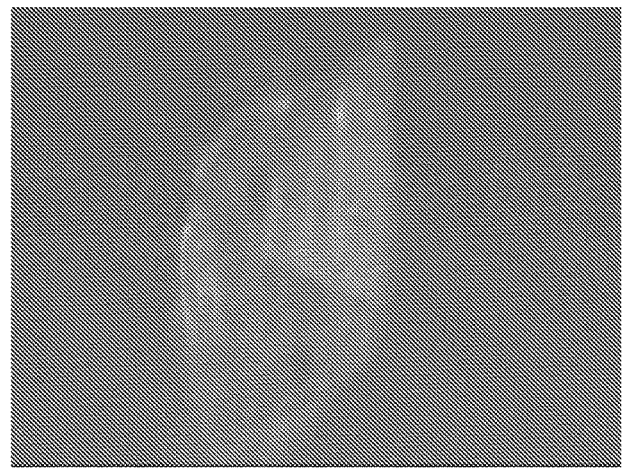
FIG. 27 shows plate form crystals observed for compound of formula (I) besylate Form 2.

A crystal of compound of formula (I) besylate Form 2, which has a plate habit, is imaged in FIG. 27.

A single plate habit crystal (ca. 0.7×0.30×0.25 mm in size) was selected and its cell parameters determined at 260K then at 190K. No transition was observed on lowering the temperature between 260-190K. The structure analysed here is for the data at 190K; parameters of the crystal and the X-ray diffraction refinement are given in Table 16.

TABLE 16

Data of the ethanol:ethyl acetate grown crystal of compound of formula (I) besylate, Form 2.

| | |
|---|---|
| Crystal State | |
| Code | CNS7056 besylate |
| Solvent | ethanol |
| Anti-solvent/Co-solvent | ethyl acetate |
| Crystal Morphology | plate |
| Crystal Size (mm) | 0.7 × 0.30 × 0.25 |
| Colour | colourless |
| Crystal Structure | |
| Formula | $C_{27}H_{25}Br_1N_4O_5S_1$ |
| Formula Weight | 597.49 |
| System | Orthorhombic |
| Space Group | P $2_12_12_1$ |
| Unit Cell a (Å) | 8.92130 (10) |
| b (Å) | 11.1526 (2) |
| c (Å) | 25.8345 (4) |
| α (°) | 90 |
| β (°) | 90 |
| γ (°) | 90 |
| Volume (Å$^3$) | 2570.65 (7) |
| Z (No. molecules in unit) | 4 |
| Z' (No. molecules in asymmetric unit) | 1 |
| Density (g cm$^3$) | 1.544 |
| Absorption μ [MoKα] (mm$^{-1}$) | 1.727 |
| F(000) | 1224 |
| Data Collection | |
| Temperature, (K) | 190 |
| Instrument | Kappa CCD diffractometer |
| Scan Type | ω |
| Absorption Correction Type | multi-scan |
| No. of Measured Reflections | 5750 |
| No. of Independent Reflections | 5727 |
| θ min/max (°) | 5.15/27.48 |
| h min/max | −11/11 |
| k min/max | −14/14 |
| l min/max | −33/33 |
| Refinement | |
| Refinement On | F |
| I/σ(I) Cut-off | 3 |
| No. of Used Reflections | 4067 |
| No. of Parameters | 344 |
| R factor (%) | 3.85 |
| Rw factor (%) | 3.66 |
| S | 1.12 |
| Δρ(min) Å$^{-3}$ | −0.6 |
| Δρ(max) Å$^{-3}$ | 0.5 |
| Max Shift/Error | 0.0003 |
| Flack Parameter | 0.011 (9) |

Figure 28:
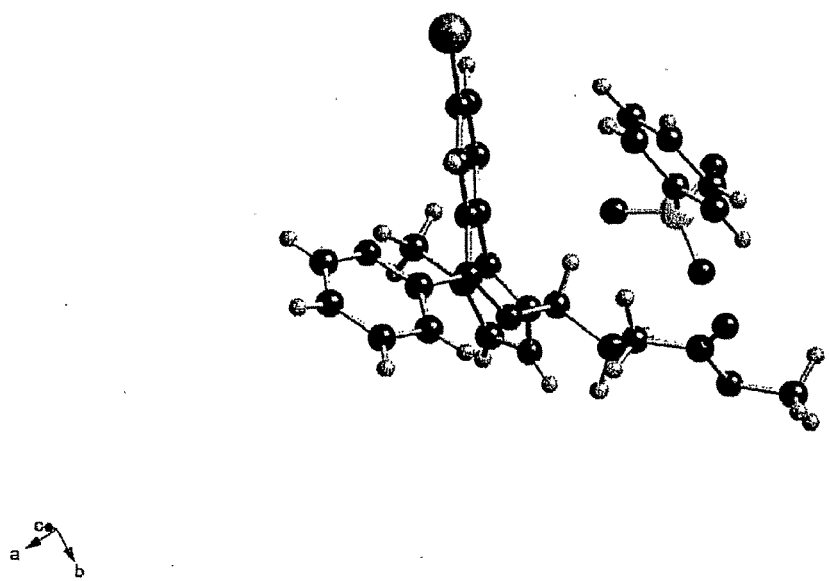
FIG. 28 shows content of the asymmetric unit in Form 2.

The content of the asymmetric unit is displayed in FIG. 28. It consists of one independent molecule of the compound and one independent besylate. The compound has the imidazole-Nitrogen protonated.

The Flack "Enantiopole" parameter was determined as 0.011(9) and thus the stereochemistry of the structures depicted here are well established and are consistent with the purported stereochemistry for the compound. Crystallographic co-ordinates and other relevant data are tabulated in the form of a SHELX file in Table 18.

The conformational disorder can be represented (in first approximation) by the "thermal ellipsoids" of the atomic positions, as presented on FIG. 29. It can be seen that the major regions of disorder lie in the besylate.

As discussed above, the conformation of the ester chain in Form 2, depicted in FIG. 30, is different to that adopted in Form 1.

Figure 31:
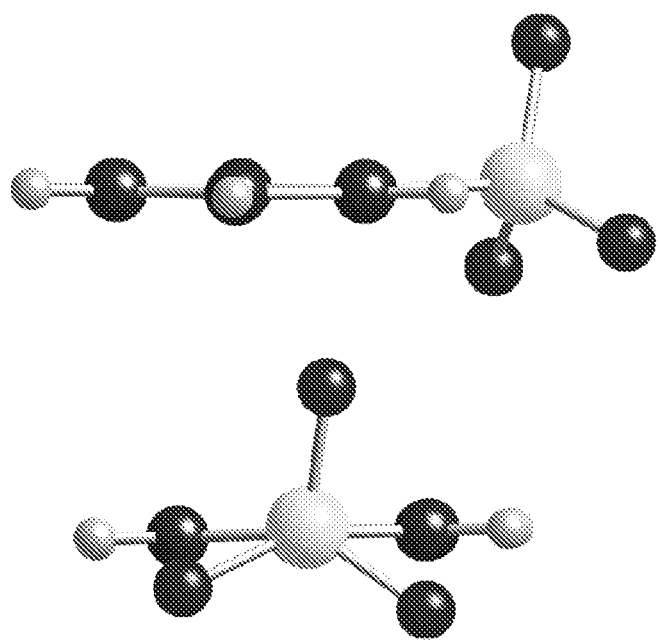
FIG. 31 shows conformation adopted by the independent besylate in Form 2, viewed along two different directions.

However, the conformation of the besylate is similar to the one observed for one of the besylate in Form 1 (FIG. 31).

Figure 32A:
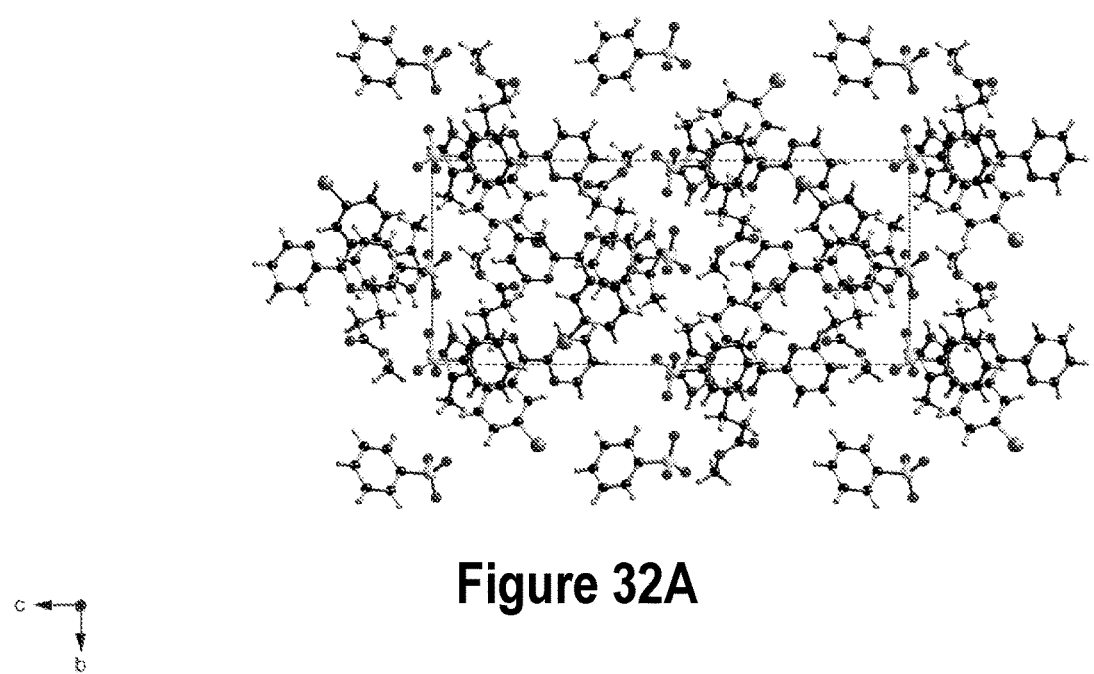
FIGS. 32A-32C show a crystal structure, determined by single-crystal X-ray diffraction of a crystal of compound of formula (I) besylate Form 2, viewed along the crystallographic a axis (FIG. 32A), b axis (FIG. 32B), and c axis (FIG. 32C)
Figure 32B:
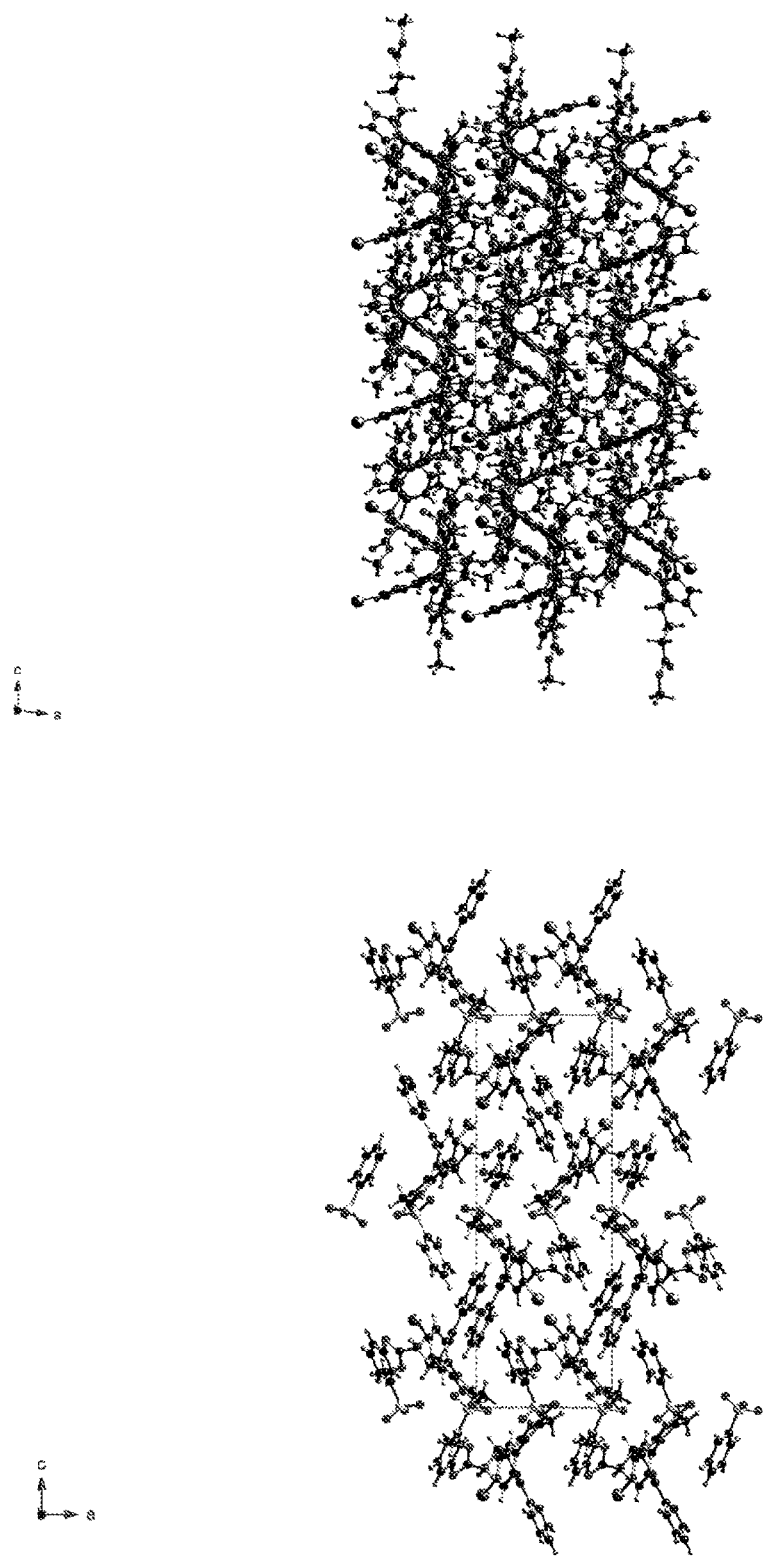
Figure 32C:
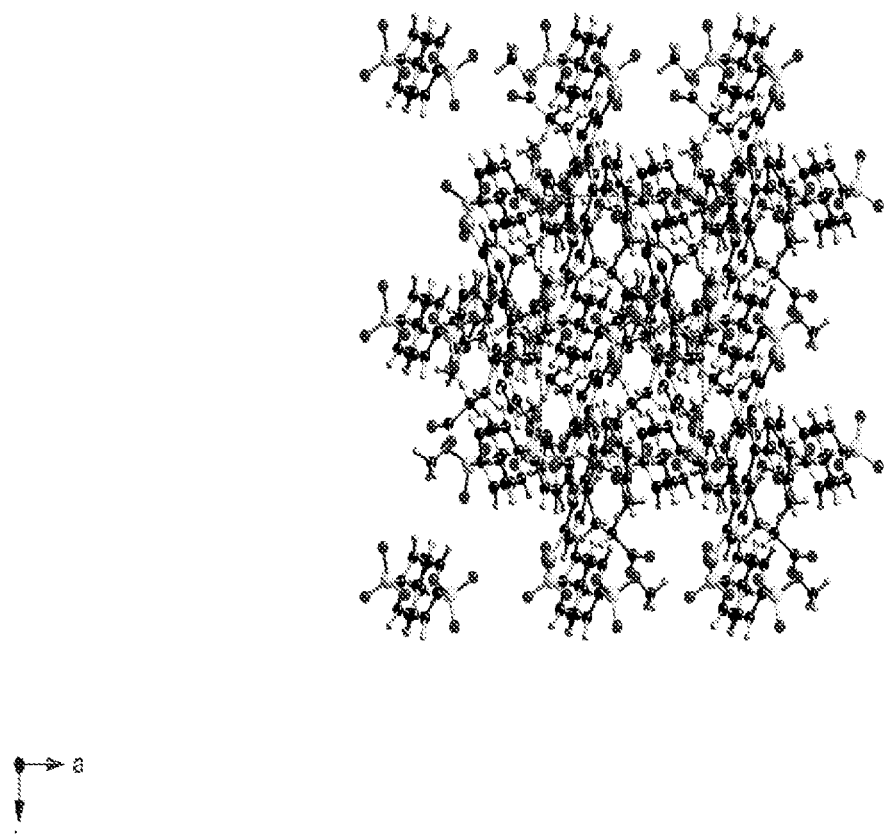
Figure 33:
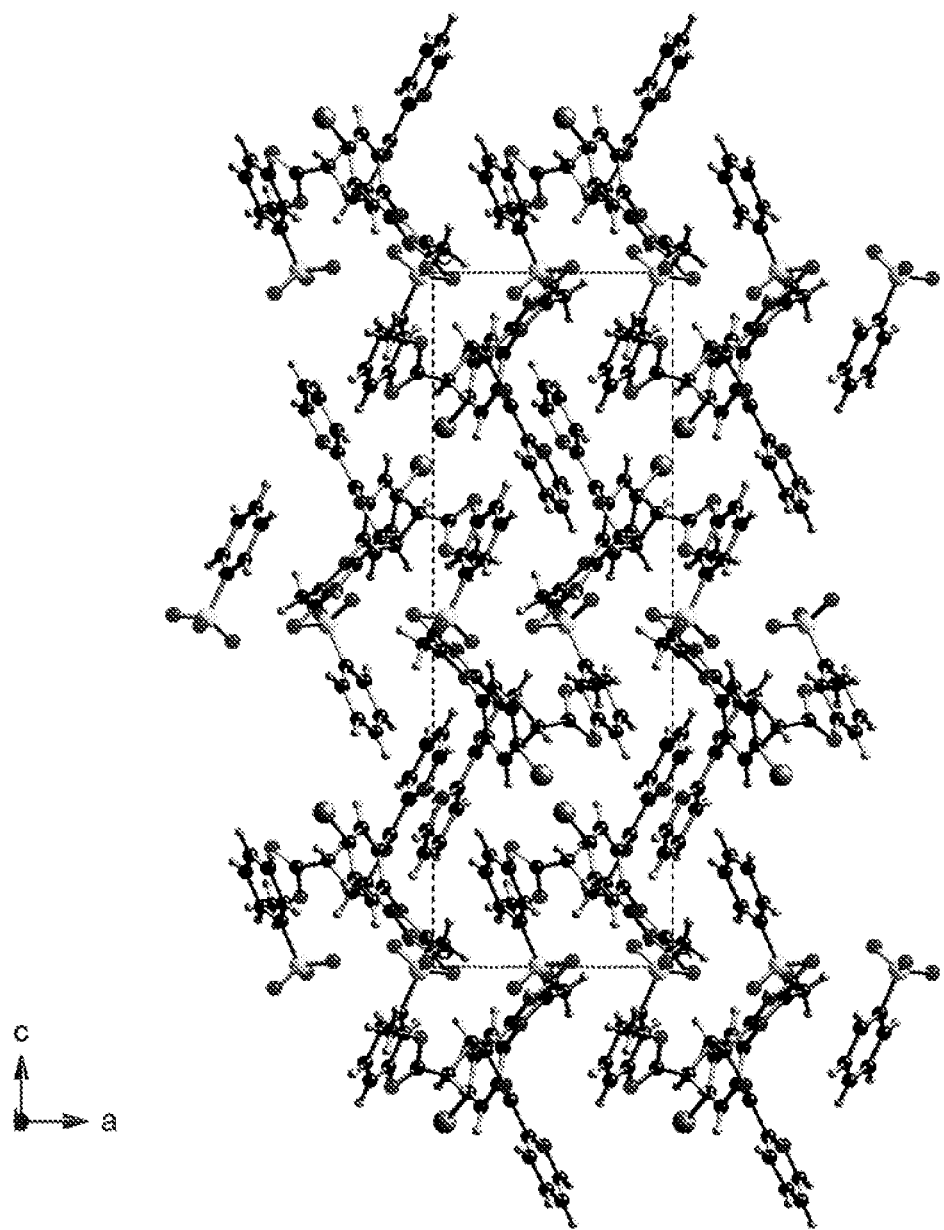
FIG. 33 shows short contact C—O<3.6 Å, C—C<3.6 Å and N—O<3.5 Å for Form 2.

The resolved crystal structure, viewed along the crystallographic a, b and c axes, is illustrated in FIGS. 32a, b and c respectively with FIG. 33 summarising the shortest contacts observed in the crystal packing. The compound establishes a short contact (hydrogen-bond type) with one oxygen atom of the besylate through its protonated nitrogen of the imidazole ring. Other short contacts (C—C, C—O, H—O) are observed between the compound and the besylate through the imidazole ring.

Some close contacts are also observed between the two compounds themselves (Br—C, C—C, O—C, O—H), most of which are via the ester chain. There are no close contacts between the besylate themselves.

Figure 34:
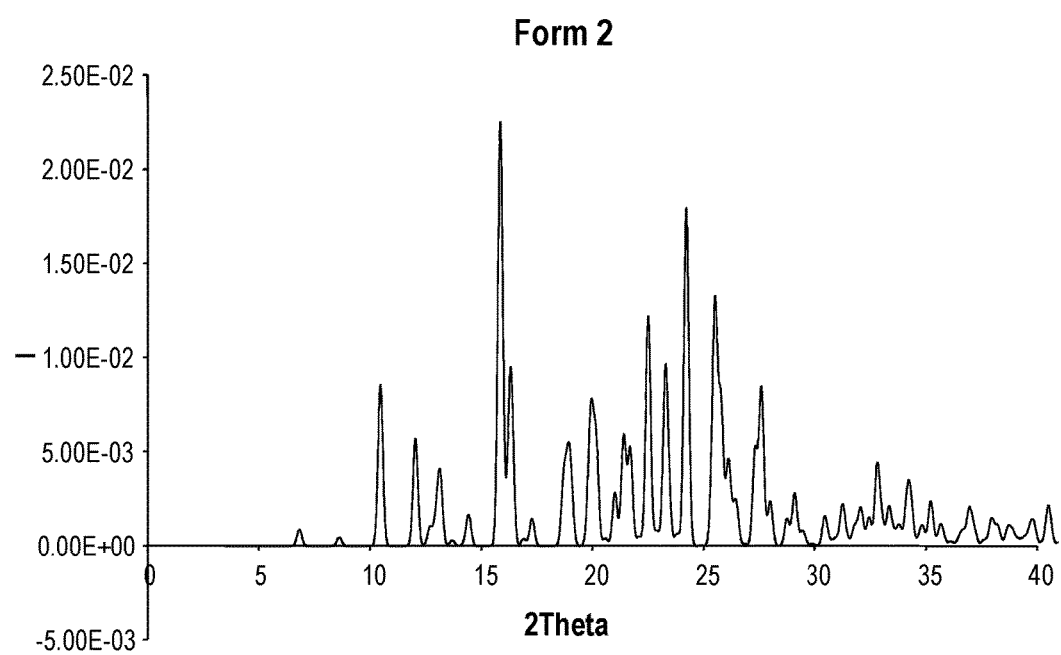
FIG. 34 shows calculated powder pattern diffraction from single crystal X-ray diffraction data for Form 2.
Figure 35:
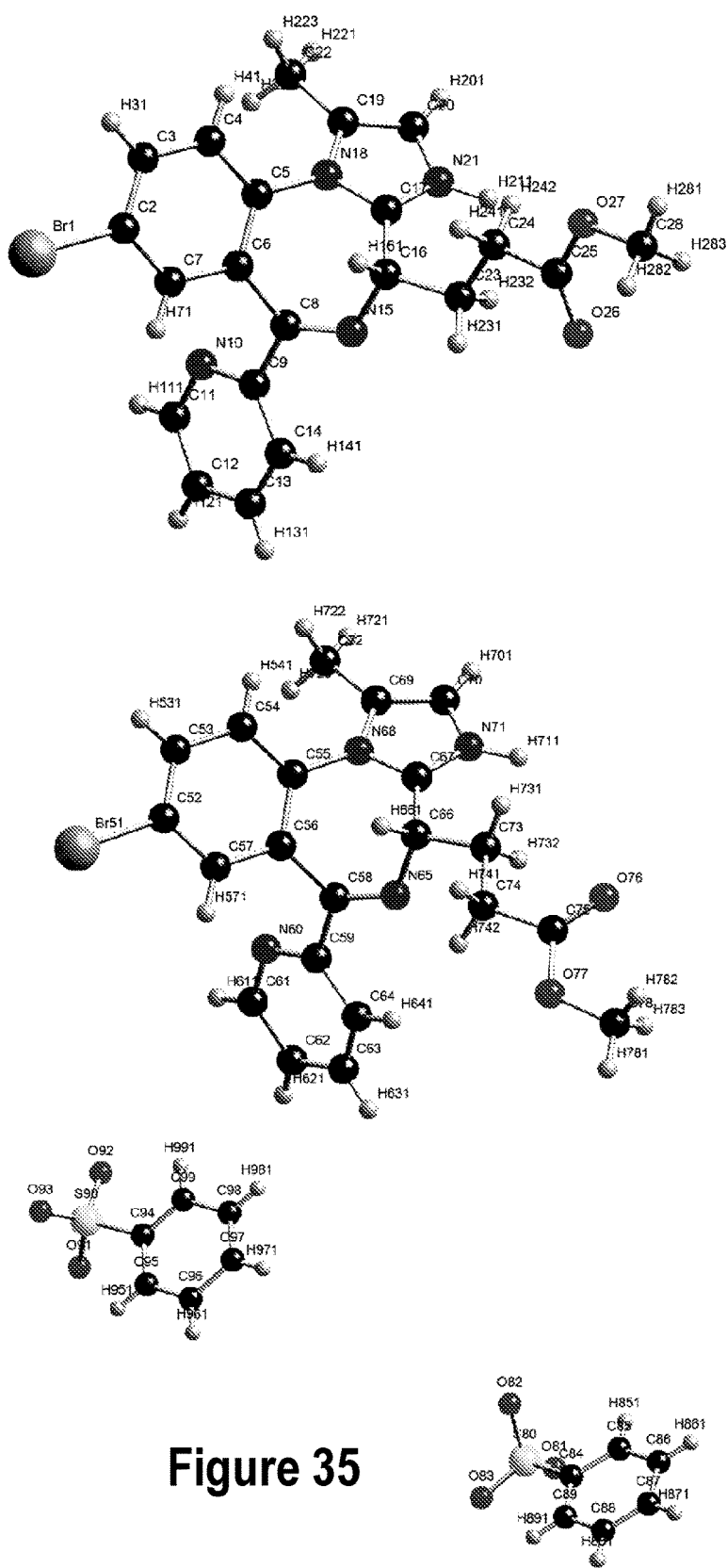
FIG. 35 shows labelling of atomic centres for Compound of formula (I) besylate Form 1.
Figure 36:
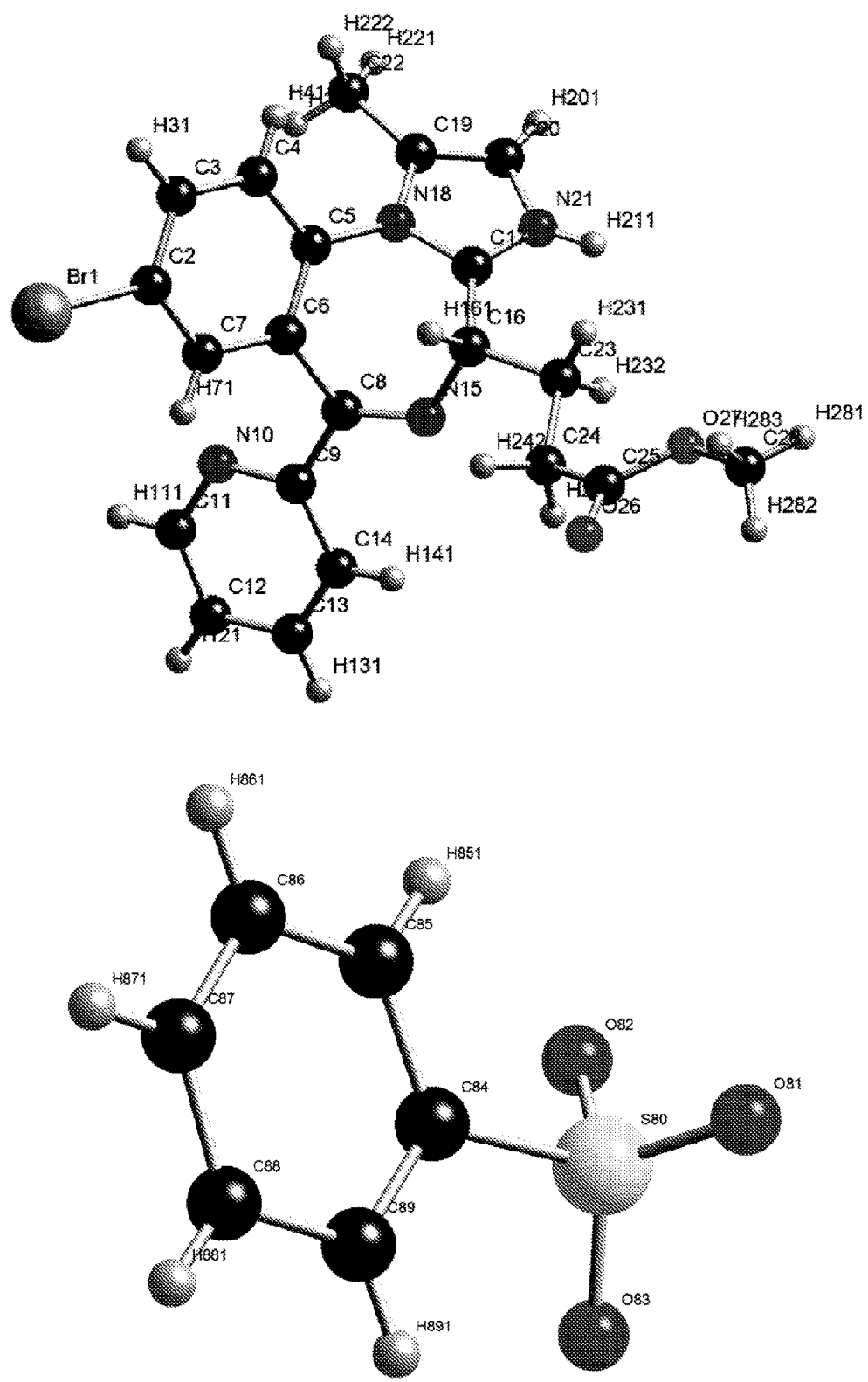
FIG. 36 shows labelling of atomic centres for Compound of formula (I) besylate Form 2.

Using the crystal structure determined experimentally, a powder diffraction pattern for Form 2 has been calculated using CrystalDiffract® (FIG. 34). This powder pattern matches the experimental powder pattern reported for Form 2.

TABLE 17

Crystallographic co-ordinates and other relevant data tabulated in the form of a SHELX File for Compound of formula (I) besylate Form 1.

TITL 12161316 Compound CNS7056 Form 1
CELL 0.71073 7.687 29.261 12.376 90.000 97.788 90.000
ZERR 2 0.0001 0.0005 0.0003 0.0000 0.0008 0.0000
LATT −1
SYMM −X, Y + 0.500, −Z
SFAC C 2.3100 20.8439 1.0200 10.2075 1.5886 0.5687 0.8650 = 51.6512 0.2156 0.0033 0.0016 1.15 0.7700 12.0110
SFAC H 0.4930 10.5109 0.3229 26.1257 0.1402 3.1424 0.0408 = 57.7998 0.0030 0.0000 0.0000 0.06 0.3200 1.0079
SFAC O 3.0485 13.2771 2.2868 5.7011 1.5463 0.3239 0.8670 = 32.9089 0.2508 0.0106 0.0060 3.25 0.7700 15.9994
SFAC BR 17.1789 2.1723 5.2358 16.5796 5.6377 0.2609 3.9851 = 41.4328 2.9557 −0.2901 2.4595 1000.00 1.1000 79.9040
SFAC N 12.2126 0.0057 3.1322 9.8933 2.0125 28.9975 1.1663 = 0.5826 −11.5290 0.0061 0.0033 1.96 0.7700 14.0067
SFAC S 6.9053 1.4679 5.2034 22.2151 1.4379 0.2536 1.5863 = 56.1720 0.8669 0.1246 0.1234 53.20 1.1100 32.0660
UNIT 108. 100. 20. 4. 16. 4.
S80 6 0.23964 0.43139 0.09908 11.00000 0.04634 0.03299 = 0.04052 0.00002 0.01880 −0.00340
O81 3 0.16028 0.39374 0.15143 11.00000 0.06864 0.04111 = 0.05255 −0.00210 0.02801 0.00002
O82 3 0.14598 0.47435 0.11207 11.00000 0.08099 0.03603 = 0.04614 0.00545 0.03373 −0.00236
O83 3 0.42589 0.43401 0.12925 11.00000 0.05754 0.08564 = 0.05198 −0.01536 0.01792 −0.00644
C84 1 0.20581 0.41866 −0.04324 11.00000 0.05949 0.04444 = 0.02903 0.00359 0.01728 0.00704
C85 1 0.03624 0.41100 −0.09142 11.00000 0.06649 0.10092 = 0.05586 0.01088 0.01751 0.00507
C86 1 0.00323 0.39810 −0.20187 11.00000 0.08670 0.14765 = −0.02096 −0.03160 −0.00004
C87 1 0.14311 0.39209 −0.25693 11.00000 0.07916 0.11651 = 0.06238 −0.01696 0.00195 0.02481
C88 1 0.30473 0.39806 −0.20987 11.00000 0.09246 0.09710 = 0.04155 0.00157 0.01795 0.02685

TABLE 17-continued

Crystallographic co-ordinates and other relevant data tabulated in the form of a SHELX File for Compound of formula (I) besylate Form 1.

C89 1 0.33456 0.41126 −0.10133 11.00000 0.05999 0.09817 = 0.07178 −0.01451 0.00886 0.02173
S90 6 0.68868 0.81145 0.51625 11.00000 0.04072 0.02869 = 0.05437 0.00158 0.00214 0.00223
O91 3 0.79129 0.77464 0.57315 11.00000 0.08025 0.03751 = 0.04867 −0.00213 −0.00954 0.01626
O92 3 0.52601 0.81933 0.56122 11.00000 0.04778 0.05360 = 0.06934 −0.00642 0.01702 0.00039
O93 3 0.78935 0.85213 0.50763 11.00000 0.07515 0.04369 = 0.05025 −0.01354 0.01764 −0.01547
C94 1 0.62446 0.78970 0.38130 11.00000 0.04232 0.04028 = 0.05049 0.00898 0.00929 0.00525
C95 1 0.74659 0.76959 0.32396 11.00000 0.06194 0.06998 = 0.03238 0.00341 −0.00103 0.00990
C96 1 0.69911 0.75023 0.22476 11.00000 0.12417 0.10337 = 0.03441 0.01537 0.02421 0.03314
C97 1 0.51941 0.75295 0.17732 11.00000 0.11897 0.11939 = −0.01324 −0.00963 −0.00586
C98 1 0.40301 0.77268 0.23169 11.00000 0.06106 0.10242 = 0.00570 −0.01263 −0.00283
C99 1 0.45446 0.79193 0.33547 11.00000 0.05307 0.07089 = 0.00728 −0.00426 −0.01944
BR1 4 0.06011 0.52462 0.55140 11.00000 0.04153 0.05204 = 0.07369 −0.00524 0.02434 0.00670
C2 1 0.25757 0.50395 0.49005 11.00000 0.02832 0.04536 = 0.03350 −0.00752 0.01511 0.00763
C3 1 0.28921 0.45781 0.47911 11.00000 0.03135 0.03107 = 0.04579 0.00145 0.00221 −0.00479
C4 1 0.42954 0.44393 0.43174 11.00000 0.03767 0.03461 = −0.00320 −0.00151 −0.00125
C5 1 0.54674 0.47556 0.39943 11.00000 0.03535 0.02939 = 0.03479 −0.00390 0.00647 0.00183
C6 1 0.51907 0.52242 0.41134 11.00000 0.04226 0.03479 = 0.04333 −0.00172 0.00236 0.00188
C7 1 0.37213 0.53602 0.45794 11.00000 0.03598 0.02793 = 0.04586 −0.00044 0.01652 0.00336
C8 1 0.64321 0.55824 0.38118 11.00000 0.03964 0.02453 = 0.02719 0.00516 0.00457 0.00373
C9 1 0.68998 0.59645 0.46059 11.00000 0.03743 0.03694 = 0.04454 −0.00375 0.01588 0.00649
N10 5 0.69097 0.58514 0.56581 11.00000 0.06070 0.03116 = 0.04918 −0.00640 0.02020 −0.00054
C11 1 0.74090 0.61847 0.63822 11.00000 0.06804 0.05787 = 0.04752 −0.00600 0.01695 −0.00669
C12 1 0.78515 0.66221 0.61053 11.00000 0.05480 0.04458 = 0.05526 −0.02125 0.01554 −0.00787
C13 1 0.77550 0.67229 0.50132 11.00000 0.04463 0.03102 = 0.05452 0.00407 0.01432 −0.00038
C14 1 0.73186 0.63955 0.42553 11.00000 0.04272 0.03021 = 0.04282 −0.00243 0.01499 0.00270
N15 5 0.71451 0.55972 0.29408 11.00000 0.04979 0.02502 = 0.03692 0.00975 0.01748 0.00775
C16 1 0.67500 0.52204 0.21324 11.00000 0.04463 0.02346 = 0.04948 −0.00464 0.01738 0.00561
C17 1 0.75857 0.47996 0.26673 11.00000 0.04549 0.02673 = 0.01954 −0.00693 0.00506 −0.00121
N18 5 0.70009 0.45973 0.35317 11.00000 0.03293 0.02806 = 0.02597 −0.00088 0.00321 0.00207
C19 1 0.81334 0.42409 0.39181 11.00000 0.03678 0.02848 = 0.03351 −0.00426 0.00585 0.00488
C20 1 0.93968 0.42402 0.32661 11.00000 0.03371 0.02802 = 0.03711 0.00202 0.00106 0.00680
N21 5 0.90585 0.45925 0.25315 11.00000 0.04775 0.03416 = 0.02231 −0.01051 0.01052 −0.00308
C22 1 0.79597 0.39511 0.48941 11.00000 0.03997 0.03711 = 0.04548 0.01039 0.00508 0.00197
C23 1 0.74788 0.53407 0.10940 11.00000 0.05650 0.04712 = 0.03514 0.00836 0.00449 0.00605
C24 1 0.68780 0.50047 0.01647 11.00000 0.08242 0.04077 = 0.03001 −0.00046 0.01385 0.00523
C25 1 0.71419 0.51690 −0.09234 11.00000 0.06429 0.06543 = 0.03392 0.00018 0.00559 −0.00499
O26 3 0.76261 0.55440 −0.11450 11.00000 0.12347 0.08282 = 0.04188 0.01501 0.01658 −0.04001
O27 3 0.65910 0.48459 −0.16756 11.00000 0.10340 0.06919 = 0.03191 0.00253 0.01824 −0.00449

TABLE 17-continued

Crystallographic co-ordinates and other relevant data tabulated in the form of a SHELX File for Compound of formula (I) besylate Form 1.

C28 1 0.66642 0.49760 −0.27953 11.00000 0.19131 0.12699 =
0.01390 −0.01417 0.02134 −0.05279
BR51 4 1.06737 0.71057 0.98743 11.00000 0.03812 0.08781 =
0.06774 0.00566 −0.00531 0.00447
C52 1 0.84276 0.73306 0.93243 11.00000 0.03132 0.05952 =
0.03819 0.00358 0.00226 −0.00263
C53 1 0.81293 0.77906 0.93249 11.00000 0.04627 0.06820 =
0.03723 −0.00581 0.00481 −0.00474
C54 1 0.65043 0.79579 0.88269 11.00000 0.04551 0.03939 =
0.04858 −0.00084 0.00376 −0.01071
C55 1 0.51946 0.76552 0.84226 11.00000 0.04294 0.03573 =
0.03413 0.00062 0.00952 −0.00208
C56 1 0.54512 0.71765 0.84581 11.00000 0.02688 0.03659 =
0.04586 −0.00025 0.00561 0.00047
C57 1 0.71139 0.70186 0.88914 11.00000 0.03105 0.04840 =
0.04447 −0.00668 −0.00429 0.00504
C58 1 0.40956 0.68443 0.79765 11.00000 0.03348 0.02893 =
0.04334 0.00070 0.00351 0.00421
C59 1 0.38048 0.64253 0.86694 11.00000 0.03165 0.03488 =
0.04951 0.00002 0.00425 0.00528
N60 5 0.42879 0.64650 0.97247 11.00000 0.03542 0.05694 =
0.03178 0.00872 0.00154 0.00467
C61 1 0.38962 0.61026 1.03529 11.00000 0.04457 0.06338 =
0.05765 0.01416 0.00707 0.00171
C62 1 0.30187 0.57202 0.98967 11.00000 0.06548 0.04957 =
0.11303 0.03456 0.03582 0.00696
C63 1 0.25733 0.56863 0.88018 11.00000 0.07395 0.04664 =
0.09803 0.00115 0.01240 −0.01007
C64 1 0.29561 0.60475 0.81590 11.00000 0.08355 0.04152 =
0.05459 −0.00010 0.00128 −0.02308
N65 5 0.31344 0.68797 0.70771 11.00000 0.03846 0.03072 =
0.04952 −0.00160 0.00032 0.00597
C66 1 0.33129 0.72953 0.64125 11.00000 0.03574 0.02676 =
0.05519 0.00406 0.00580 0.00330
C67 1 0.26347 0.76733 0.70231 11.00000 0.03803 0.03316 =
0.04166 0.01528 0.00868 0.00029
N68 5 0.35122 0.78274 0.79764 11.00000 0.03387 0.03259 =
0.05055 0.00549 0.00427 0.00218
C69 1 0.24763 0.81583 0.84108 11.00000 0.05345 0.03305 =
0.04570 0.00005 0.02067 −0.00546
C70 1 0.09873 0.81841 0.77077 11.00000 0.04465 0.03799 =
0.06107 0.00794 0.01464 0.00936
N71 5 0.10819 0.78841 0.68720 11.00000 0.03892 0.03266 =
0.05306 0.00974 0.01063 0.00803
C72 1 0.30218 0.84064 0.94469 11.00000 0.08091 0.04934 =
0.08052 −0.01505 0.02392 −0.00661
C73 1 0.22541 0.72388 0.52948 11.00000 0.04039 0.05583 =
0.03295 0.00047 0.00724 −0.00165
C74 1 0.30154 0.68566 0.46508 11.00000 0.05896 0.05343 =
0.05504 −0.00576 0.00667 0.02016
C75 1 0.18003 0.67204 0.36587 11.00000 0.05296 0.05447 =
0.04241 0.00546 0.01355 0.00171
O76 3 0.06782 0.69497 0.31818 11.00000 0.05552 0.07543 =
0.05719 −0.00702 −0.00194 0.02108
O77 3 0.22119 0.62976 0.33149 11.00000 0.08466 0.04267 =
0.04376 −0.00714 0.00726 0.00488
C78 1 0.10717 0.61220 0.23887 11.00000 0.06302 0.09312 =
0.07465 −0.02449 0.02418 −0.00980
H611 2 10.42342 10.61111 11.10933 11.00000 0.06582
H621 2 10.27371 10.54835 11.03412 11.00000 0.09086
H631 2 10.20282 10.54235 10.84949 11.00000 0.08585
H641 2 10.26600 10.60396 10.74163 11.00000 0.07058
H661 2 10.45616 10.73494 10.63683 11.00000 0.04658
H701 2 10.00528 10.83765 10.77749 11.00000 0.05724
H721 2 10.20390 10.85662 10.96784 11.00000 0.10482
H722 2 10.39143 10.86250 10.93477 11.00000 0.10500
H723 2 10.34863 10.81975 11.00178 11.00000 0.10479
H731 2 10.22647 10.75279 10.49048 11.00000 0.05050
H732 2 10.10462 10.71635 10.53573 11.00000 0.05107
H741 2 10.41143 10.69632 10.44327 11.00000 0.06599
H742 2 10.32279 10.65905 10.51273 11.00000 0.06616
H571 2 10.73613 10.67093 10.88928 11.00000 0.04893
H531 2 10.89874 10.79871 10.96543 11.00000 0.05990
H541 2 10.63029 10.82681 10.87790 11.00000 0.05285
H161 2 10.54702 10.51731 10.19609 11.00000 0.04687
H201 2 11.03302 10.40374 10.33036 11.00000 0.03977
H221 2 10.90306 10.37871 10.51025 11.00000 0.06107

TABLE 17-continued

Crystallographic co-ordinates and other relevant data tabulated in the form of a SHELX File for Compound of formula (I) besylate Form 1.

H222 2 10.77354 10.41394 10.54853 11.00000 0.06102
H223 2 10.70245 10.37370 10.47387 11.00000 0.06087
H231 2 10.71028 10.56434 10.08666 11.00000 0.05487
H232 2 10.87494 10.53365 10.12431 11.00000 0.05471
H241 2 10.56546 10.49241 10.01723 11.00000 0.06095
H242 2 10.75795 10.47323 10.02815 11.00000 0.06099
H111 2 10.74728 10.61186 10.71244 11.00000 0.06882
H121 2 10.81997 10.68398 10.66349 11.00000 0.06182
H131 2 10.79812 10.70154 10.48020 11.00000 0.05215
H141 2 10.72939 10.64544 10.35226 11.00000 0.04595
H71 2 10.35042 10.56684 10.46668 11.00000 0.04408
H31 2 10.21444 10.43638 10.50355 11.00000 0.04223
H41 2 10.44931 10.41280 10.42055 11.00000 0.04056
H891 2 10.44977 10.41481 9.93226 11.00000 0.09285
H881 2 10.39917 10.39332 9.75106 11.00000 0.09266
H871 2 10.12372 10.38356 9.66972 11.00000 0.10194
H861 2 9.88808 10.39388 9.76390 11.00000 0.11607
H851 2 9.94416 10.41466 9.94909 11.00000 0.08904
H951 2 10.86472 10.76918 10.35546 11.00000 0.06580
H961 2 10.78321 10.73544 10.18942 11.00000 0.10497
H971 2 10.48493 10.74055 10.10914 11.00000 0.10604
H981 2 10.28646 10.77378 10.20054 11.00000 0.08719
H991 2 10.37377 10.80653 10.37249 11.00000 0.07037
H781 2 10.14480 10.58182 10.22240 11.00000 0.11588
H782 2 10.11102 10.63197 10.17669 11.00000 0.11581
H783 2 9.98883 10.61082 10.25546 11.00000 0.11600
H711 2 10.01359 10.78308 10.62464 11.00000 0.05205
H211 2 10.98261 10.46785 10.19729 11.00000 0.04161
H281 2 10.62358 10.47180 9.67092 11.00000 0.11566
H282 2 10.59036 10.52501 9.70225 11.00000 0.11566
H283 2 10.79029 10.50514 9.71088 11.00000 0.11566

TABLE 18

Crystallographic co-ordinates and other relevant data tabulated in the form of a SHELX File for Compound of formula (I) besylate Form 2.

TITL 1142055 Compound CNS7056 form 2
CELL 0.71073 8.921 11.154 25.834 90.000 90.000 90.000
ZERR 4 0.0001 0.0002 0.0004 0.0000 0.0000 0.0000
LATT −1
SYMM X + 0.500, −Y + 0.500, −Z
SYMM −X, Y + 0.500, −Z + 0.500
SYMM −X + 0.500, −Y, Z + 0.500
SFAC C 2.3100 20.8439 1.0200 10.2075 1.5886 0.5687 0.8650 =
51.6512 0.2156 0.0033 0.0016 1.15 0.7700 12.0110
SFAC H 0.4930 10.5109 0.3229 26.1257 0.1402 3.1424 0.0408 =
57.7998 0.0030 0.0000 0.0000 0.06 0.3200 1.0079
SFAC BR 17.1789 2.1723 5.2358 16.5796 5.6377 0.2609 3.9851 =
41.4328 2.9557 −0.2901 2.4595 1000.00 1.1000 79.9040
SFAC N 12.2126 0.0057 3.1322 9.8933 2.0125 28.9975 1.1663 =
0.5826 −11.5290 0.0061 0.0033 1.96 0.7700 14.0067
SFAC O 3.0485 13.2771 2.2868 5.7011 1.5463 0.3239 0.8670 =
32.9089 0.2508 0.0106 0.0060 3.25 0.7700 15.9994
SFAC S 6.9053 1.4679 5.2034 22.2151 1.4379 0.2536 1.5863 =
56.1720 0.8669 0.1246 0.1234 53.20 1.1100 32.0660
UNIT 108. 100. 4. 16. 20. 4.
BR1 3 −0.04819 −0.10880 −0.27710 11.00000 0.07032 0.03277 =
0.00144 −0.01238 −0.02224
C2 1 −0.15018 −0.21830 −0.32054 11.00000 0.02777 0.02177 =
−0.00009 −0.00209 −0.00471
C3 1 −0.17401 −0.18875 −0.37205 11.00000 0.02963 0.01861 =
0.02702 0.00623 0.00188 −0.00107
C4 1 −0.24491 −0.26965 −0.40362 11.00000 0.02825 0.02442 =
0.01718 0.00327 0.00106 −0.00145
C5 1 −0.29275 −0.37943 −0.38401 11.00000 0.02223 0.01822 =
0.01875 −0.00067 0.00141 0.00066
C6 1 −0.27139 −0.40894 −0.33163 11.00000 0.02028 0.01967 =
0.01926 0.00182 0.00105 −0.00153
C7 1 −0.20042 −0.32532 −0.29979 11.00000 0.02809 0.02763 =
0.01685 0.00206 0.00190 −0.00055
C8 1 −0.32197 −0.52600 −0.30927 11.00000 0.01670 0.02233 =
0.00135 −0.00476 −0.00144

TABLE 18-continued

Crystallographic co-ordinates and other relevant data tabulated in the form of a SHELX File for Compound of formula (I) besylate Form 2.

```
C9 1 -0.39853 -0.52353 -0.25770 11.00000 0.01623 0.02317 =
0.00259 -0.00384 -0.00281
N10 4 -0.46099 -0.41943 -0.24363 11.00000 0.02251 0.02613 =
0.02353 -0.00189 0.00408 0.00155
C11 1 -0.52777 -0.41652 -0.19697 11.00000 0.02617 0.03441 =
0.02357 -0.00451 0.00365 0.00346
C12 1 -0.53610 -0.51390 -0.16425 11.00000 0.02740 0.04329 =
0.02040 -0.00335 0.00652 -0.00779
C13 1 -0.47518 -0.62062 -0.17997 11.00000 0.03584 0.03200 =
0.02405 0.00767 0.00645 -0.00687
C14 1 -0.40334 -0.62685 -0.22730 11.00000 0.02879 0.02223 =
0.02565 0.00090 0.00272 -0.00057
N15 4 -0.30040 -0.62781 -0.33049 11.00000 0.02151 0.02416 =
0.01713 0.00287 -0.00002 0.00182
C16 1 -0.21928 -0.62991 -0.38036 11.00000 0.02330 0.02286 =
0.01602 0.00057 0.00417 0.00450
C17 1 -0.32510 -0.57975 -0.41920 11.00000 0.02824 0.02308 =
0.01704 -0.00121 0.00336 -0.00285
N18 4 -0.36294 -0.46298 -0.41818 11.00000 0.02482 0.02037 =
0.01483 0.00150 -0.00070 0.00079
C19 1 -0.46920 -0.44117 -0.45641 11.00000 0.03022 0.02725 =
0.01634 0.00325 0.00039 -0.00224
C20 1 -0.49445 -0.54753 -0.47911 11.00000 0.03071 0.03401 =
0.00110 -0.00174 -0.00215
N21 4 -0.40440 -0.63226 -0.45591 11.00000 0.03619 0.02354 =
0.02146 -0.00463 0.00147 -0.00154
C22 1 -0.54310 -0.32298 -0.46595 11.00000 0.03636 0.03429 =
0.00778 -0.00982 -0.00011
C23 1 -0.15995 -0.75547 -0.39193 11.00000 0.03430 0.02640 =
0.01793 -0.00359 0.00177 0.00554
C24 1 -0.06166 -0.79435 -0.34621 11.00000 0.04707 0.03881 =
0.02350 0.00041 0.00034 0.01530
C25 1 0.06625 -0.87542 -0.35603 11.00000 0.03182 0.02650 =
0.00340 -0.00125 -0.00016
O26 5 0.17233 -0.88334 -0.32760 11.00000 0.03778 0.06570 =
0.03313 -0.01160 -0.01173 0.00417
O27 5 0.05245 -0.94265 -0.39885 11.00000 0.03130 0.03874 =
0.02467 -0.00799 -0.00330 0.01418
C28 1 0.17574 -1.02443 -0.40867 11.00000 0.05622 0.08123 =
0.03697 -0.01153 -0.00496 0.04396
S80 6 -0.94275 -0.52899 -0.49624 11.00000 0.03340 0.02679 =
0.02442 0.00000 0.00210 -0.00075
O81 5 -0.83867 -0.47114 -0.53020 11.00000 0.05118 0.08336 =
0.02297 -0.00622 -0.02476
O82 5 -1.08156 -0.46260 -0.49186 11.00000 0.04015 0.07788 =
0.05503 -0.01022 -0.00539 0.01721
O83 5 -0.97025 -0.65272 -0.50726 11.00000 0.13945 0.03230 =
0.06071 -0.01467 0.01447 -0.00725
C84 1 -0.86288 -0.52210 -0.43343 11.00000 0.02735 0.05893 =
0.02832 0.01509 0.00686 -0.00534
C85 1 -0.87781 -0.41462 -0.40588 11.00000 0.03763 0.08695 =
0.03855 -0.01799 0.00427 -0.00754
C86 1 -0.81420 -0.39965 -0.35764 11.00000 0.05438 0.16315 =
0.04455 -0.02905 0.00147 -0.02905
C87 1 -0.73766 -0.49241 -0.33773 11.00000 0.06202 0.20226 =
0.03510 -0.02105 -0.05062
C88 1 -0.71885 -0.60444 -0.36221 11.00000 0.04217 0.17120 =
0.11388 0.10762 -0.01320 -0.03729
C89 1 -0.78500 -0.61610 -0.41251 11.00000 0.03725 0.08786 =
0.05538 -0.00772 -0.01074
H891 2 9.22557 9.31210 9.56883 11.00000 0.08027
H881 2 9.33331 9.33306 9.65289 11.00000 0.13097
H851 2 9.06867 9.64846 9.57936 11.00000 0.06577
H861 2 9.17563 9.67239 9.66111 11.00000 0.10509
H161 2 9.86530 9.42517 9.62245 11.00000 0.02469
H111 2 9.42959 9.65626 9.81326 11.00000 0.03383
H121 2 9.41618 9.49292 9.86839 11.00000 0.03606
H131 2 9.51614 9.31066 9.84059 11.00000 0.03697
H141 2 9.64103 9.30191 9.76144 11.00000 0.03108
H231 2 9.89972 9.24922 9.57680 11.00000 0.03066
H232 2 9.75764 9.18723 9.60372 11.00000 0.03099
H241 2 9.87585 9.16237 9.67759 11.00000 0.04434
H242 2 9.97980 9.27746 9.67100 11.00000 0.04489
H281 2 10.15353 8.92912 9.56085 11.00000 0.08666
H282 2 10.18989 8.92278 9.62053 11.00000 0.08723
H283 2 10.26566 9.02166 9.58620 11.00000 0.08710
H201 2 9.44027 9.43682 9.49457 11.00000 0.03327
H221 2 9.36727 9.66624 9.51370 11.00000 0.05146
H222 2 9.52479 9.72860 9.51527 11.00000 0.05104
H223 2 9.43193 9.71611 9.56601 11.00000 0.05131
H41 2 9.73983 9.74902 9.56204 11.00000 0.02807
H31 2 9.85823 9.88568 9.61518 11.00000 0.03001
H71 2 9.81367 9.65791 9.73490 11.00000 0.02870
H871 2 9.30621 9.51762 9.69480 11.00000 0.13226
H211 2 9.59801 9.29339 9.53630 11.00000 0.03270
```

TABLE 19

Bond lengths for Compound of formula (I) besylate Form 1.

| | | | | | |
|---|---|---|---|---|---|
| S80 | O81 | 1.454(5) Å | S80 | O82 | 1.468(5) Å |
| S80 | O83 | 1.432(6) Å | S80 | C84 | 1.784(7) Å |
| C84 | C85 | 1.376(12) Å | C84 | C89 | 1.318(12) Å |
| C85 | C86 | 1.408(14) Å | C85 | H851 | 0.927 Å |
| C86 | C87 | 1.360(16) Å | C86 | H861 | 0.936 Å |
| C87 | C88 | 1.310(15) Å | C87 | H871 | 0.934 Å |
| C88 | C89 | 1.386(14) Å | C88 | H881 | 0.935 Å |
| C89 | H891 | 0.932 Å | S90 | O91 | 1.459(5) Å |
| S90 | O92 | 1.454(6) Å | S90 | O93 | 1.431(5) Å |
| S90 | C94 | 1.793(8) Å | C94 | C95 | 1.383(11) Å |
| C94 | C99 | 1.354(11) Å | C95 | C96 | 1.356(13) Å |
| C95 | H951 | 0.938 Å | C96 | C97 | 1.428(17) Å |
| C96 | H961 | 0.934 Å | C97 | C98 | 1.323(15) Å |
| C97 | H971 | 0.924 Å | C98 | C99 | 1.409(13) Å |
| C98 | H981 | 0.927 Å | C99 | H991 | 0.924 Å |
| Br1 | C2 | 1.886(6) Å | C2 | C3 | 1.382(9) Å |
| C2 | C7 | 1.381(9) Å | C3 | C4 | 1.358(10) Å |
| C3 | H31 | 0.928 Å | C4 | C5 | 1.388(9) Å |
| C4 | H41 | 0.937 Å | C5 | C6 | 1.398(9) Å |
| C5 | N18 | 1.454(8) Å | C6 | C7 | 1.394(9) Å |
| C6 | C8 | 1.498(9) Å | C7 | H71 | 0.926 Å |
| C8 | C9 | 1.500(9) Å | C8 | N15 | 1.274(8) Å |
| C9 | N10 | 1.343(9) Å | C9 | C14 | 1.386(9) Å |
| N10 | C11 | 1.345(10) Å | C11 | C12 | 1.379(11) Å |
| C11 | H111 | 0.933 Å | C12 | C13 | 1.375(11) Å |
| C12 | H121 | 0.927 Å | C13 | C14 | 1.351(10) Å |
| C13 | H131 | 0.918 Å | C14 | H141 | 0.921 Å |
| N15 | C16 | 1.492(9) Å | C16 | C17 | 1.500(9) Å |
| C16 | C23 | 1.511(9) Å | C16 | H161 | 0.988 Å |
| C17 | N18 | 1.352(8) Å | C17 | N21 | 1.315(8) Å |
| N18 | C19 | 1.400(8) Å | C19 | C20 | 1.344(9) Å |
| C19 | C22 | 1.496(9) Å | C20 | N21 | 1.376(8) Å |
| C20 | H201 | 0.927 Å | N21 | H211 | 1.000 Å |
| C22 | H221 | 0.958 Å | C22 | H222 | 0.950 Å |
| C22 | H223 | 0.953 Å | C23 | C24 | 1.536(11) Å |
| C23 | H231 | 0.969 Å | C23 | H232 | 0.969 Å |
| C24 | C25 | 1.470(11) Å | C24 | H241 | 0.971 Å |
| C24 | H242 | 0.962 Å | C25 | O26 | 1.202(10) Å |
| C25 | O27 | 1.354(10) Å | O27 | C28 | 1.445(10) Å |
| C28 | H281 | 1.000 Å | C28 | H282 | 1.000 Å |
| C28 | H283 | 1.000 Å | Br51 | C52 | 1.886(7) Å |
| C52 | C53 | 1.366(11) Å | C52 | C57 | 1.412(10) Å |
| C53 | C54 | 1.404(11) Å | C53 | H531 | 0.927 Å |
| C54 | C55 | 1.383(10) Å | C54 | H541 | 0.921 Å |
| C55 | C56 | 1.414(9) Å | C55 | N68 | 1.427(9) Å |
| C56 | C57 | 1.396(9) Å | C56 | C58 | 1.489(9) Å |
| C57 | H571 | 0.925 Å | C58 | C59 | 1.530(10) Å |
| C58 | N65 | 1.254(8) Å | C59 | N60 | 1.314(9) Å |
| C59 | C64 | 1.391(10) Å | N60 | C61 | 1.372(9) Å |
| C61 | C62 | 1.386(14) Å | C61 | H611 | 0.918 Å |
| C62 | C63 | 1.355(15) Å | C62 | H621 | 0.928 Å |
| C63 | C64 | 1.378(13) Å | C63 | H631 | 0.932 Å |
| C64 | H641 | 0.917 Å | N65 | C66 | 1.485(8) Å |
| C66 | C67 | 1.474(9) Å | C66 | C73 | 1.516(10) Å |
| C66 | H661 | 0.982 Å | C67 | N68 | 1.354(9) Å |
| C67 | N71 | 1.334(9) Å | N68 | C69 | 1.406(9) Å |
| C69 | C70 | 1.343(11) Å | C69 | C72 | 1.484(12) Å |
| C70 | N71 | 1.366(10) Å | C70 | H701 | 0.925 Å |
| N71 | H711 | 1.000 Å | C72 | H721 | 0.964 Å |
| C72 | H722 | 0.958 Å | C72 | H723 | 0.965 Å |
| C73 | C74 | 1.535(10) Å | C73 | H731 | 0.975 Å |

TABLE 19-continued

Bond lengths for Compound of formula (I) besylate Form 1.

| | | | | | | |
|---|---|---|---|---|---|---|
| C73 | H732 | 0.967 Å | C74 | C75 | 1.493(12) Å |
| C74 | H741 | 0.972 Å | C74 | H742 | 0.977 Å |
| C75 | O76 | 1.185(9) Å | C75 | O77 | 1.360(9) Å |
| O77 | C78 | 1.440(11) Å | C78 | H781 | 0.965 Å |
| C78 | H782 | 0.966 Å | C78 | H783 | 0.960 Å |

TABLE 20

Angles for Compound of formula (I) besylate Form 1

| | | | | | | | |
|---|---|---|---|---|---|---|---|
| O81 | S80 | O82 | 111.0(3)° | O81 | S80 | O83 | 112.9(4)° |
| O82 | S80 | O83 | 114.4(4)° | O81 | S80 | C84 | 105.5(3)° |
| O82 | S80 | C84 | 106.2(3)° | O83 | S80 | C84 | 106.0(4)° |
| S80 | C84 | C85 | 117.7(6)° | S80 | C84 | C89 | 123.6(7)° |
| C85 | C84 | C89 | 118.3(8)° | C84 | C85 | C86 | 120.0(9)° |
| C84 | C85 | H851 | 119.626° | C86 | C85 | H851 | 120.377° |
| C85 | C86 | C87 | 118.1(10)° | C85 | C86 | H861 | 120.636° |
| C87 | C86 | H861 | 121.303° | C86 | C87 | C88 | 121.8(10)° |
| C86 | C87 | H871 | 119.251° | C88 | C87 | H871 | 118.984° |
| C87 | C88 | C89 | 119.3(10)° | C87 | C88 | H881 | 120.392° |
| C89 | C88 | H881 | 120.264° | C84 | C89 | C88 | 122.5(10)° |
| C84 | C89 | H891 | 118.485° | C88 | C89 | H891 | 119.061° |
| O91 | S90 | O92 | 111.7(3)° | O91 | S90 | O93 | 112.8(4)° |
| O92 | S90 | O93 | 113.5(3)° | O91 | S90 | C94 | 104.5(3)° |
| O92 | S90 | C94 | 105.7(3)° | O93 | S90 | C94 | 108.0(3)° |
| S90 | C94 | C95 | 120.6(6)° | S90 | C94 | C99 | 120.1(6)° |
| C95 | C94 | C99 | 119.3(8)° | C94 | C95 | C96 | 121.6(9)° |
| C94 | C95 | H951 | 118.566° | C96 | C95 | H951 | 119.820° |
| C95 | C96 | C97 | 118.4(10)° | C95 | C96 | H961 | 119.911° |
| C97 | C96 | H961 | 121.695° | C96 | C97 | C98 | 119.9(8)° |
| C96 | C97 | H971 | 119.699° | C98 | C97 | H971 | 120.397° |
| C97 | C98 | C99 | 120.8(9)° | C97 | C98 | H981 | 119.080° |
| C99 | C98 | H981 | 120.094° | C94 | C99 | C98 | 119.9(9)° |
| C94 | C99 | H991 | 119.276° | C98 | C99 | H991 | 120.819° |
| Br1 | C2 | C3 | 121.0(5)° | Br1 | C2 | C7 | 118.5(5)° |
| C3 | C2 | C7 | 120.5(5)° | C2 | C3 | C4 | 119.7(6)° |
| C2 | C3 | H31 | 120.203° | C4 | C3 | H31 | 120.109° |
| C3 | C4 | C5 | 120.6(6)° | C3 | C4 | H41 | 120.600° |
| C5 | C4 | H41 | 118.766° | C4 | C5 | C6 | 120.6(6)° |
| C4 | C5 | N18 | 119.6(5)° | C6 | C5 | N18 | 119.8(6)° |
| C5 | C6 | C7 | 117.8(6)° | C5 | C6 | C8 | 123.3(6)° |
| C7 | C6 | C8 | 118.8(6)° | C2 | C7 | C6 | 120.6(6)° |
| C2 | C7 | H71 | 119.721° | C6 | C7 | H71 | 119.679° |
| C6 | C8 | C9 | 117.5(5)° | C6 | C8 | N15 | 126.6(6)° |
| C9 | C8 | N15 | 115.9(6)° | C8 | C9 | N10 | 114.9(6)° |
| C8 | C9 | C14 | 121.2(6)° | N10 | C9 | C14 | 123.9(6)° |
| C9 | N10 | C11 | 115.5(6)° | N10 | C11 | C12 | 124.4(7)° |
| N10 | C11 | H111 | 118.526° | C12 | C11 | H111 | 117.061° |
| C11 | C12 | C13 | 117.4(7)° | C11 | C12 | H121 | 121.279° |
| C13 | C12 | H121 | 121.289° | C12 | C13 | C14 | 120.4(6)° |
| C12 | C13 | H131 | 119.499° | C14 | C13 | H131 | 120.125° |
| C9 | C14 | C13 | 118.3(6)° | C9 | C14 | H141 | 120.274° |
| C13 | C14 | H141 | 121.419° | C8 | N15 | C16 | 118.0(5)° |
| N15 | C16 | C17 | 105.9(5)° | N15 | C16 | C23 | 109.4(5)° |
| C17 | C16 | C23 | 112.4(5)° | N15 | C16 | H161 | 110.723° |
| C17 | C16 | H161 | 109.539° | C23 | C16 | H161 | 108.851° |
| C16 | C17 | N18 | 122.7(6)° | C16 | C17 | N21 | 130.3(6)° |
| N18 | C17 | N21 | 106.5(5)° | C5 | N18 | C17 | 123.1(5)° |
| C5 | N18 | C19 | 127.0(5)° | C17 | N18 | C19 | 109.8(5)° |
| N18 | C19 | C20 | 105.2(5)° | N18 | C19 | C22 | 125.3(6)° |
| C20 | C19 | C22 | 129.4(6)° | C19 | C20 | N21 | 108.0(5)° |
| C19 | C20 | H201 | 126.017° | N21 | C20 | H201 | 126.026° |
| C17 | N21 | C20 | 110.5(5)° | C17 | N21 | H211 | 124.840° |
| C20 | N21 | H211 | 124.681° | C19 | C22 | H221 | 109.508° |
| C19 | C22 | H222 | 109.778° | H221 | C22 | H222 | 108.808° |
| C19 | C22 | H223 | 110.905° | H221 | C22 | H223 | 108.786° |
| H222 | C22 | H223 | 109.018° | C16 | C23 | C24 | 112.3(6)° |
| C16 | C23 | H231 | 109.392° | C24 | C23 | H231 | 108.812° |
| C16 | C23 | H232 | 108.378° | C24 | C23 | H232 | 109.105° |
| H231 | C23 | H232 | 108.825° | C23 | C24 | C25 | 114.3(7)° |
| C23 | C24 | H241 | 109.968° | C25 | C24 | H241 | 110.030° |
| C23 | C24 | H242 | 108.195° | C25 | C24 | H242 | 105.346° |
| H241 | C24 | H242 | 108.752° | C24 | C25 | O26 | 126.4(7)° |
| C24 | C25 | O27 | 109.4(7)° | O26 | C25 | O27 | 123.9(7)° |
| C25 | O27 | C28 | 115.2(7)° | O27 | C28 | H281 | 109.674° |

TABLE 20-continued

Angles for Compound of formula (I) besylate Form 1

| | | | | | | | |
|---|---|---|---|---|---|---|---|
| O27 | C28 | H282 | 109.261° | H281 | C28 | H282 | 109.475° |
| O27 | C28 | H283 | 109.465° | H281 | C28 | H283 | 109.476° |
| H282 | C28 | H283 | 109.476° | Br51 | C52 | C53 | 119.3(6)° |
| Br51 | C52 | C57 | 119.0(5)° | C53 | C52 | C57 | 121.7(7)° |
| C52 | C53 | C54 | 118.9(7)° | C52 | C53 | H531 | 120.141° |
| C54 | C53 | H531 | 120.985° | C53 | C54 | C55 | 119.8(7)° |
| C53 | C54 | H541 | 120.227° | C55 | C54 | H541 | 120.000° |
| C54 | C55 | C56 | 122.1(6)° | C54 | C55 | N68 | 119.4(6)° |
| C56 | C55 | N68 | 118.5(6)° | C55 | C56 | C57 | 117.2(6)° |
| C55 | C56 | C58 | 123.2(6)° | C57 | C56 | C58 | 119.5(6)° |
| C52 | C57 | C56 | 120.2(7)° | C52 | C57 | H571 | 119.709° |
| C56 | C57 | H571 | 120.138° | C56 | C58 | C59 | 116.5(6)° |
| C56 | C58 | N65 | 126.7(6)° | C59 | C58 | N65 | 116.8(6)° |
| C58 | C59 | N60 | 116.3(6)° | C58 | C59 | C64 | 118.5(7)° |
| N60 | C59 | C64 | 125.0(7)° | C59 | N60 | C61 | 116.1(7)° |
| N60 | C61 | C62 | 121.7(8)° | N60 | C61 | H611 | 119.342° |
| C62 | C61 | H611 | 118.993° | C61 | C62 | C63 | 120.6(8)° |
| C61 | C62 | H621 | 120.029° | C63 | C62 | H621 | 119.353° |
| C62 | C63 | C64 | 118.4(9)° | C62 | C63 | H631 | 120.452° |
| C64 | C63 | H631 | 121.124° | C59 | C64 | C63 | 118.1(8)° |
| C59 | C64 | H641 | 120.844° | C63 | C64 | H641 | 121.057° |
| C58 | N65 | C66 | 118.2(6)° | N65 | C66 | C67 | 105.4(5)° |
| N65 | C66 | C73 | 109.7(5)° | C67 | C66 | C73 | 111.5(6)° |
| N65 | C66 | H661 | 109.122° | C67 | C66 | H661 | 108.890° |
| C73 | C66 | H661 | 112.017° | C66 | C67 | N68 | 121.8(6)° |
| C66 | C67 | N71 | 130.3(7)° | N68 | C67 | N71 | 107.4(6)° |
| C55 | N68 | C67 | 122.5(6)° | C55 | N68 | C69 | 128.7(6)° |
| C67 | N68 | C69 | 108.7(6)° | N68 | C69 | C70 | 105.5(6)° |
| N68 | C69 | C72 | 124.0(7)° | C70 | C69 | C72 | 130.5(7)° |
| C69 | C70 | N71 | 109.1(6)° | C69 | C70 | H701 | 125.444° |
| N71 | C70 | H701 | 125.502° | C67 | N71 | C70 | 109.2(6)° |
| C67 | N71 | H711 | 125.400° | C70 | N71 | H711 | 125.366° |
| C69 | C72 | H721 | 110.667° | C69 | C72 | H722 | 109.838° |
| H721 | C72 | H722 | 108.539° | C69 | C72 | H723 | 110.831° |
| H721 | C72 | H723 | 108.455° | H722 | C72 | H723 | 108.445° |
| C66 | C73 | C74 | 111.0(6)° | C66 | C73 | H731 | 108.535° |
| C74 | C73 | H731 | 110.248° | C66 | C73 | H732 | 110.751° |
| C74 | C73 | H732 | 108.249° | H731 | C73 | H732 | 108.042° |
| C73 | C74 | C75 | 112.4(6)° | C73 | C74 | H741 | 108.496° |
| C75 | C74 | H741 | 109.125° | C73 | C74 | H742 | 108.155° |
| C75 | C74 | H742 | 108.578° | H741 | C74 | H742 | 110.035° |
| C74 | C75 | O76 | 126.2(7)° | C74 | C75 | O77 | 110.7(7)° |
| O76 | C75 | O77 | 123.0(7)° | C75 | O77 | C78 | 115.6(7)° |
| O77 | C78 | H781 | 109.214° | O77 | C78 | H782 | 109.848° |
| H781 | C78 | H782 | 109.923° | O77 | C78 | H783 | 109.687° |
| H781 | C78 | H783 | 109.026° | H782 | C78 | H783 | 109.127° |

TABLE 21

Bond Lengths for Compound of formula (I) besylate Form 2.

| | | | | | |
|---|---|---|---|---|---|
| Br1 | C2 | 1.892(3) Å | C2 | C3 | 1.387(5) Å |
| C2 | C7 | 1.383(5) Å | C3 | C4 | 1.371(5) Å |
| C3 | H31 | 0.938 Å | C4 | C5 | 1.392(5) Å |
| C4 | H41 | 0.921 Å | C5 | C6 | 1.406(4) Å |
| C5 | N18 | 1.428(4) Å | C6 | C7 | 1.395(5) Å |
| C6 | C8 | 1.497(4) Å | C7 | H71 | 0.924 Å |
| C8 | C9 | 1.497(4) Å | C8 | N15 | 1.276(4) Å |
| C9 | N10 | 1.338(4) Å | C9 | C14 | 1.395(5) Å |
| N10 | C11 | 1.345(4) Å | C11 | C12 | 1.378(5) Å |
| C11 | H111 | 0.935 Å | C12 | C13 | 1.370(5) Å |
| C12 | H121 | 0.948 Å | C13 | C14 | 1.382(5) Å |
| C13 | H131 | 0.936 Å | C14 | H141 | 0.934 Å |
| N15 | C16 | 1.478(4) Å | C16 | C17 | 1.487(5) Å |
| C16 | C23 | 1.527(5) Å | C16 | H161 | 0.976 Å |
| C17 | N18 | 1.346(4) Å | C17 | N21 | 1.320(4) Å |
| N18 | C19 | 1.391(4) Å | C19 | C20 | 1.342(5) Å |
| C19 | C22 | 1.494(5) Å | C20 | N21 | 1.378(5) Å |
| C20 | H201 | 0.912 Å | N21 | H211 | 0.854 Å |
| C22 | H221 | 0.965 Å | C22 | H222 | 0.966 Å |
| C22 | H223 | 0.960 Å | C23 | C24 | 1.534(5) Å |
| C23 | H231 | 0.969 Å | C23 | H232 | 0.981 Å |
| C24 | C25 | 1.478(5) Å | C24 | H241 | 0.960 Å |
| C24 | H242 | 0.988 Å | C25 | O26 | 1.201(4) Å |
| C25 | O27 | 1.342(4) Å | O27 | C28 | 1.451(5) Å |

TABLE 21-continued

Bond Lengths for Compound of formula (I) besylate Form 2.

| | | | | | | |
|---|---|---|---|---|---|---|
| C28 | H281 | 0.964 Å | C28 | H282 | 0.965 Å | |
| C28 | H283 | 0.962 Å | S80 | O81 | 1.431(3) Å | |
| S80 | O82 | 1.447(3) Å | S80 | O83 | 1.430(3) Å | |
| S80 | C84 | 1.774(4) Å | C84 | C85 | 1.400(7) Å | |
| C84 | C89 | 1.369(7) Å | C85 | C86 | 1.380(7) Å | |
| C85 | H851 | 0.932 Å | C86 | C87 | 1.342(13) Å | |
| C86 | H861 | 0.943 Å | C87 | C88 | 1.410(13) Å | |
| C87 | H871 | 0.934 Å | C88 | C89 | 1.433(10) Å | |
| C88 | H881 | 0.925 Å | C89 | H891 | 0.940 Å | |

TABLE 22

Angles for Compound of formula (I) besylate Form 2.

| | | | | | | | |
|---|---|---|---|---|---|---|---|
| Br1 | C2 | C3 | 119.3(3)° | Br1 | C2 | C7 | 118.9(3)° |
| C3 | C2 | C7 | 121.8(3)° | C2 | C3 | C4 | 119.0(3)° |
| C2 | C3 | H31 | 120.033° | C4 | C3 | H31 | 120.959° |
| C3 | C4 | C5 | 120.3(3)° | C3 | C4 | H41 | 119.485° |
| C5 | C4 | H41 | 120.261° | C4 | C5 | C6 | 121.0(3)° |
| C4 | C5 | N18 | 118.9(3)° | C6 | C5 | N18 | 120.1(3)° |
| C5 | C6 | C7 | 118.2(3)° | C5 | C6 | C8 | 122.3(3)° |
| C7 | C6 | C8 | 119.5(3)° | C2 | C7 | C6 | 119.7(3)° |
| C2 | C7 | H71 | 120.432° | C6 | C7 | H71 | 119.874° |
| C6 | C8 | C9 | 117.7(3)° | C6 | C8 | N15 | 124.4(3)° |
| C9 | C8 | N15 | 117.9(3)° | C8 | C9 | N10 | 116.6(3)° |
| C8 | C9 | C14 | 120.0(3)° | N10 | C9 | C14 | 123.4(3)° |
| C9 | N10 | C11 | 116.7(3)° | N10 | C11 | C12 | 123.7(3)° |
| N10 | C11 | H111 | 117.041° | C12 | C11 | H111 | 119.278° |
| C11 | C12 | C13 | 118.8(3)° | C11 | C12 | H121 | 120.443° |
| C13 | C12 | H121 | 120.783° | C12 | C13 | C14 | 119.3(3)° |
| C12 | C13 | H131 | 120.694° | C14 | C13 | H131 | 119.952° |
| C9 | C14 | C13 | 118.1(3)° | C9 | C14 | H141 | 120.942° |
| C13 | C14 | H141 | 120.983° | C8 | N15 | C16 | 117.6(3)° |
| N15 | C16 | C17 | 105.7(3)° | N15 | C16 | C23 | 110.8(3)° |
| C17 | C16 | C23 | 115.7(3)° | N15 | C16 | H161 | 107.681° |
| C17 | C16 | H161 | 107.726° | C23 | C16 | H161 | 108.910° |
| C16 | C17 | N18 | 120.7(3)° | C16 | C17 | N21 | 131.2(3)° |
| N18 | C17 | N21 | 108.0(3)° | C5 | N18 | C17 | 122.3(3)° |
| C5 | N18 | C19 | 128.6(3)° | C17 | N18 | C19 | 109.0(3)° |
| N18 | C19 | C20 | 105.7(3)° | N18 | C19 | C22 | 124.9(3)° |
| C20 | C19 | C22 | 129.3(3)° | C19 | C20 | N21 | 108.6(3)° |
| C19 | C20 | H201 | 127.007° | N21 | C20 | H201 | 124.433° |
| C17 | N21 | C20 | 108.7(3)° | C17 | N21 | H211 | 125.926° |
| C20 | N21 | H211 | 125.351° | C19 | C22 | H221 | 110.223° |
| C19 | C22 | H222 | 109.368° | H221 | C22 | H222 | 108.664° |
| C19 | C22 | H223 | 111.184° | H221 | C22 | H223 | 109.452° |
| H222 | C22 | H223 | 107.885° | C16 | C23 | C24 | 107.9(3)° |
| C16 | C23 | H231 | 107.712° | C24 | C23 | H231 | 110.073° |
| C16 | C23 | H232 | 111.123° | C24 | C23 | H232 | 109.430° |
| H231 | C23 | H232 | 110.583° | C23 | C24 | C25 | 118.8(3)° |
| C23 | C24 | H241 | 107.661° | C25 | C24 | H241 | 104.516° |
| C23 | C24 | H242 | 109.365° | C25 | C24 | H242 | 106.503° |
| H241 | C24 | H242 | 109.671° | C24 | C25 | O26 | 123.3(3)° |
| C24 | C25 | O27 | 114.4(3)° | O26 | C25 | O27 | 122.4(3)° |
| C25 | O27 | C28 | 115.2(3)° | O27 | C28 | H281 | 108.952° |
| O27 | C28 | H282 | 110.269° | H281 | C28 | H282 | 109.738° |
| O27 | C28 | H283 | 108.681° | H281 | C28 | H283 | 110.225° |
| H282 | C28 | H283 | 108.963° | O81 | S80 | O82 | 111.9(2)° |
| O81 | S80 | O83 | 115.1(2)° | O82 | S80 | O83 | 111.2(3)° |
| O81 | S80 | C84 | 106.30(18)° | O82 | S80 | C84 | 104.5(2)° |
| O83 | S80 | C84 | 107.0(2)° | S80 | C84 | C85 | 117.6(4)° |
| S80 | C84 | C89 | 122.1(4)° | C85 | C84 | C89 | 120.2(5)° |
| C84 | C85 | C86 | 121.6(6)° | C84 | C85 | H851 | 119.148° |
| C86 | C85 | H851 | 119.275° | C85 | C86 | C87 | 117.5(8)° |
| C85 | C86 | H861 | 121.859° | C87 | C86 | H861 | 120.606° |
| C86 | C87 | C88 | 124.9(7)° | C86 | C87 | H871 | 117.763° |
| C88 | C87 | H871 | 117.376° | C87 | C88 | C89 | 116.0(7)° |
| C87 | C88 | H881 | 122.592° | C89 | C88 | H881 | 121.435° |
| C84 | C89 | C88 | 119.8(8)° | C84 | C89 | H891 | 120.080° |
| C88 | C89 | H891 | 120.078° | | | | |

What is claimed is:

1. A lyophilized composition comprising a besylate salt of the compound of formula (I)

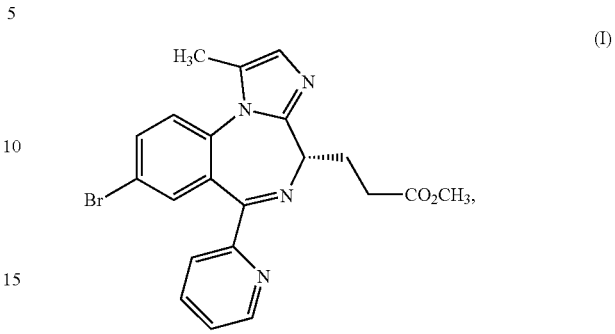

(I)

and at least one pharmaceutically acceptable carrier, excipient or diluent, wherein said lyophilized composition maintains at least 96.7% of the original amount of the compound of formula (I) comprising said lyophilized composition following storage of said lyophilized composition at 40° C. and 75% relative humidity for 4 weeks, and wherein said amount of the compound of formula (I) in said lyophilized composition is measured by high-performance liquid chromatography.

2. The lyophilized composition according to claim 1, wherein said lyophilized composition maintains at least 97.3% of the original amount of the compound of formula (I) comprising said lyophilized composition following storage of said lyophilized composition at 40° C. and 75% relative humidity for 1 week, and wherein said amount of the compound of formula (I) in said lyophilized composition is measured by high-performance liquid chromatography.

3. The lyophilized composition according to claim 1, wherein said lyophilized composition maintains at least 97.3% of the original amount of the compound of formula (I) comprising said lyophilized composition following storage of said lyophilized composition at 40° C. and 75% relative humidity for 2 weeks, and wherein said amount of the compound of formula (I) in said lyophilized composition is measured by high-performance liquid chromatography.

4. An aqueous pharmaceutical composition prepared by reconstitution of a lyophilized composition, said lyophilized composition comprising a besylate salt of the compound of formula (I)

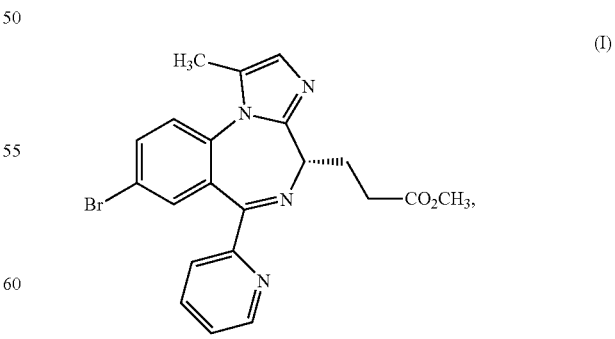

(I)

and at least one pharmaceutically acceptable carrier, excipient or diluent, wherein said lyophilized composition maintains at least 96.7% of the original amount of the compound of formula (I) comprising said lyophilized composition following storage of said lyophilized composition at 40° C. and 75% relative humidity for 4 weeks, and wherein said amount of the compound of formula (I) in said lyophilized composition is measured by high-performance liquid chromatography.

5. The aqueous pharmaceutical composition according to claim 4, wherein said lyophilized composition maintains at least 97.3% of the original amount of the compound of formula (I) comprising said lyophilized composition following storage of said lyophilized composition at 40° C. and 75% relative humidity for 1 week, and wherein said amount of the compound of formula (I) in said lyophilized composition is measured by high-performance liquid chromatography.

6. The aqueous pharmaceutical composition according to claim 4, said lyophilized composition maintains at least 97.3% of the original amount of the compound of formula (I) comprising said lyophilized composition following storage of said lyophilized composition at 40° C. and 75% relative humidity for 2 weeks, and wherein said amount of the compound of formula (I) in said lyophilized composition is measured by high-performance liquid chromatography.

7. The aqueous pharmaceutical composition according to claim 4, wherein said lyophilized composition is reconstituted with water, a dextrose solution or a saline solution.

8. The aqueous pharmaceutical composition according to claim 7, wherein said aqueous composition is presented in a unit dosage form selected from a bottle, an ampoule, a disposable injection device, and a vial.

9. The aqueous pharmaceutical composition according to claim 8, wherein said unit dosage form is an ampoule or a vial.

10. The aqueous pharmaceutical composition according to claim 9, wherein said unit dosage form contains from about 0.1 mg/mL to about 20 mg/mL of a besylate salt of the compound of formula (I).

11. The lyophilized composition according to claim 1, wherein said composition is presented in a unit dosage form selected from a bottle, an ampoule, a disposable injection device, and a vial.

12. The lyophilized composition according to claim 11, wherein said unit dosage form is an ampoule or a vial.

* * * * *

UNITED STATES PATENT AND TRADEMARK OFFICE
CERTIFICATE OF CORRECTION

PATENT NO. : 9,914,738 B2
APPLICATION NO. : 15/703945
DATED : March 13, 2018
INVENTOR(S) : Gary Stuart Tilbrook et al.

Page 1 of 2

It is certified that error appears in the above-identified patent and that said Letters Patent is hereby corrected as shown below:

In the Drawings

Figure 2:
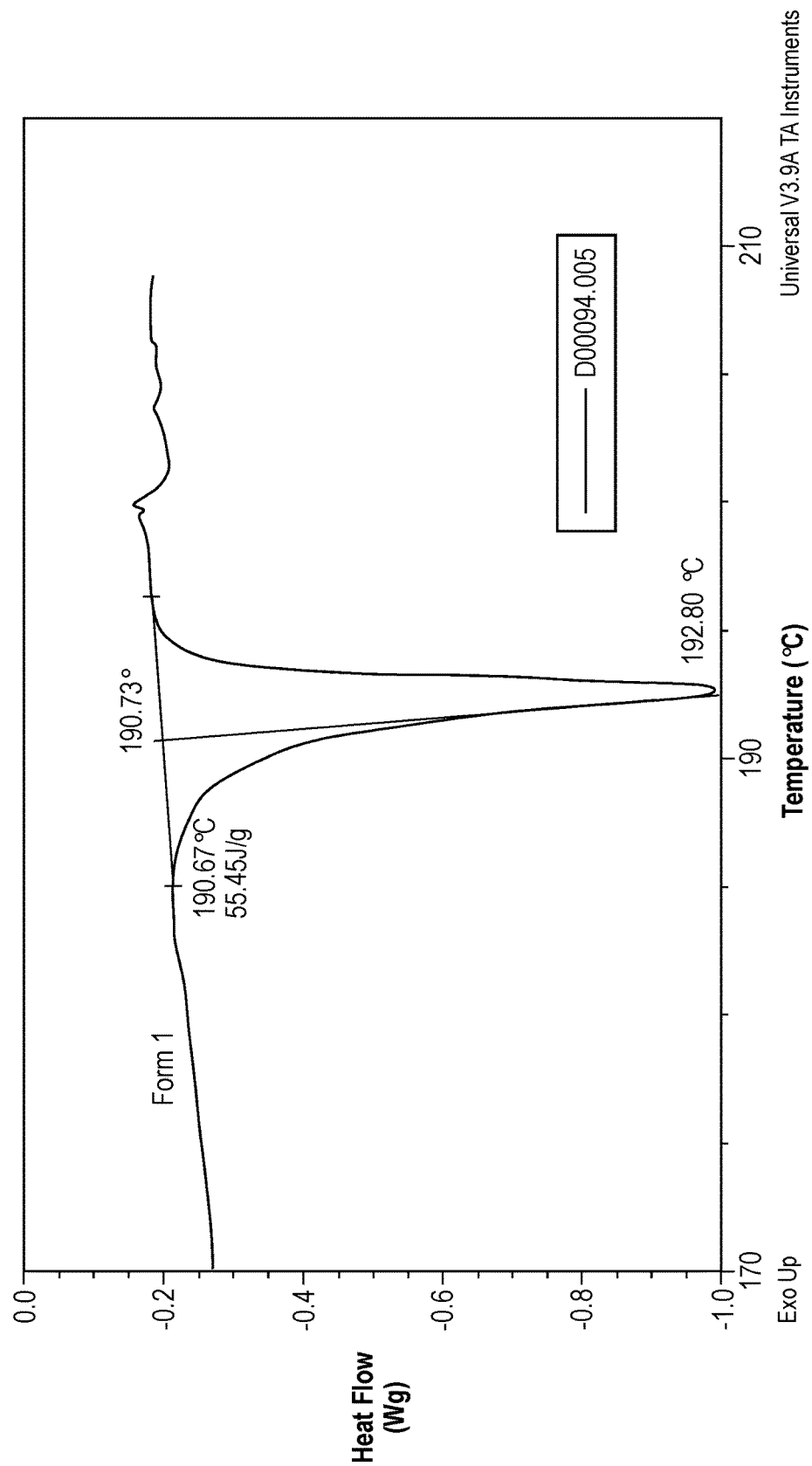
FIG. 2 shows Differential Scanning calorimetry (DSC) of LJC-039-081-1.

1. In Fig. 2, Sheet 2 of 64, delete "(Wg)" and insert -- (W/g) --, therefor.

2. In Fig. 3, Sheet 3 of 64, delete "(Wg)" and insert -- (W/g) --, therefor.

In the Specification

3. In Column 5, Line 8, delete "di methylacetamide/methyl" and insert -- dimethylacetamide/methyl --, therefor.

4. In Column 5, Lines 25-26, delete "ethano/1,2-dichlorobenzene;" and insert -- ethanol/1,2-dichlorobenzene; --, therefor.

5. In Column 10, Lines 5-15, delete "

TABLE 2

Summary of Compound of Formula (I) Appearance Data

| Storage Condition | Timepoint days | Appearance |
|---|---|---|
| RT | initial | Cream to light yellow powder |
| 5 C./AMRH Closed | 34 | Cream to light yellow powder |
| 30 C./60% RH Closed | 34 | Cream to light yellow powder |
| 40 C./75% RH Open | 34 | Deliquesced yellow mass on bottom of vial |
| 60 C./AMRH Closed | 34 | Deliquesced dark yellow to orange mass on bottom of vial |

"

Signed and Sealed this
Sixth Day of November, 2018

Andrei Iancu
*Director of the United States Patent and Trademark Office* and insert --

TABLE 2

Summary of Compound of Formula (I) Appearance Data

| Storage Condition | Timepoint days | Appearance |
|---|---|---|
| RT | initial | Cream to light yellow powder |
| 5° C./AMRH Closed | 34 | Cream to light yellow powder |
| 30° C./60% RH Closed | 34 | Cream to light yellow powder |
| 40° C./75% RH Open | 34 | Deliquesced yellow mass on bottom of vial |
| 60° C./AMRH Closed | 34 | Deliquesced dark yellow to orange mass on bottom of vial |

--, therefor.

6. In Column 10, Lines 42-61, delete "

| 5 C./AMRH Closed#1[1] | 34 | 102.6 | 95.30 | 100.52 |
| 30 C./60% RH Closed #1[1] | 34 | 94.7 | 94.20 | 99.36 |
| 40 C./75% RH Open #1 | 34 | 105.4 | 93.45 | 98.57 |
| 40 C./75% RH Open #2 | 34 | 100.3 | 93.39 | 98.50 |
| 60 C./AMRH Closed #1 | 34 | 93.4 | 87.77 | 92.57 |
| 60 C./AMRH Closed #2 | 34 | 91.1 | 87.77 | 92.57 |

" and insert --

| 5° C./AMRH Closed#1[1] | 34 | 102.6 | 95.30 | 100.52 |
| 30° C./60% RH Closed #1[1] | 34 | 94.7 | 94.20 | 99.36 |
| 40° C./75% RH Open #1 | 34 | 105.4 | 93.45 | 98.57 |
| 40° C./75% RH Open #2 | 34 | 100.3 | 93.39 | 98.50 |
| 60° C./AMRH Closed #1 | 34 | 93.4 | 87.77 | 92.57 |
| 60° C./AMRH Closed #2 | 34 | 91.1 | 87.77 | 92.57 |

--, therefor.

7. In Column 13, Line 60, delete "hostage" and insert -- hotstage --, therefor.

8. In Column 16, Line 16, delete "Hostage" and insert -- Hotstage --, therefor.

9. In Column 21, Line 65, delete "lipophillicity" and insert -- lipophilicity --, therefor.

10. In Column 28, Line 32, delete "(g cm$^3$)" and insert -- (g/cm$^3$) --, therefor.

11. In Column 30, Line 37, delete "(g cm$^3$)" and insert -- (g/cm$^3$) --, therefor.

UNITED STATES PATENT AND TRADEMARK OFFICE
CERTIFICATE OF CORRECTION

PATENT NO. : 9,914,738 B2
APPLICATION NO. : 15/703945
DATED : March 13, 2018
INVENTOR(S) : Gary Stuart Tilbrook et al.

It is certified that error appears in the above-identified patent and that said Letters Patent is hereby corrected as shown below:

In the Drawings

1. Please replace Fig. 5, as set forth on the attached Replacement Sheet.

Signed and Sealed this
First Day of January, 2019

Andrei Iancu
*Director of the United States Patent and Trademark Office*